(12) United States Patent
Donner et al.

(10) Patent No.: US 9,788,961 B2
(45) Date of Patent: Oct. 17, 2017

(54) SACROILIAC JOINT IMPLANT SYSTEM

(75) Inventors: Edward Jeffrey Donner, Fort Collins, CO (US); Christopher Thomas Donner, Fort Collins, CO (US)

(73) Assignee: JCBD, LLC, Fort Collins, CO (US)

( * ) Notice: Subject to any disclaimer, the term of this patent is extended or adjusted under 35 U.S.C. 154(b) by 578 days.

(21) Appl. No.: 14/127,119

(22) PCT Filed: Jun. 15, 2012

(86) PCT No.: PCT/US2012/042823
§ 371 (c)(1),
(2), (4) Date: Dec. 17, 2013

(87) PCT Pub. No.: WO2012/174485
PCT Pub. Date: Dec. 20, 2012

(65) Prior Publication Data
US 2014/0142700 A1    May 22, 2014

Related U.S. Application Data

(63) Continuation-in-part of application No. 13/475,695, filed on May 18, 2012, now Pat. No. 9,381,045,
(Continued)

(51) Int. Cl.
*A61F 2/44* (2006.01)
*A61B 17/70* (2006.01)
*A61F 2/30* (2006.01)

(52) U.S. Cl.
CPC ............ *A61F 2/44* (2013.01); *A61B 17/7055* (2013.01); *A61F 2/30988* (2013.01);
(Continued)

(58) Field of Classification Search
CPC .......... A61F 2/4455; A61F 2002/30622; A61F 2002/30995; A61B 17/7055;
(Continued)

(56) References Cited

U.S. PATENT DOCUMENTS

| 4,488,542 A | 12/1984 | Helland |
| 4,569,338 A | 2/1986 | Edwards |

(Continued)

FOREIGN PATENT DOCUMENTS

| AU | 1753200 | 8/2000 |
| CN | 2265765 | 10/1997 |

(Continued)

OTHER PUBLICATIONS

Medtronic Sofamor Danek. Colorado 2™ Sacro-Iliac Fixation, Surgical Technique. © 2003 Medtronic Sofamor Danek USA, Inc.
(Continued)

*Primary Examiner* — Lynnsy Summitt
(74) *Attorney, Agent, or Firm* — Polsinelli PC; Joshua J. Pranckun; Samuel Wade Johnson

(57) ABSTRACT

Accordingly, a broad object of the invention can be to provide an inventive implant to facilitate stabilization while allowing an amount of motion of a sacroiliac joint. Embodiments of the sacroiliac joint implant can provide an elongate body, which can further include at least one fixation member, or a pair of fixation members which extend a distance outward from the longitudinal axis of the implant body adapted for non-transverse placement between the articular surfaces of the sacroiliac joint, and as to certain embodiments can further provide a third fixation member and additionally a fourth fixation member each adapted to extend a distance outward from the elongate body into the bone of the sacrum or the ilium.

35 Claims, 39 Drawing Sheets

Related U.S. Application Data which is a continuation-in-part of application No. 13/236,411, filed on Sep. 19, 2011, now Pat. No. 9,017,407, which is a continuation-in-part of application No. 12/998,712, filed as application No. PCT/US2011/000070 on Jan. 13, 2011, now Pat. No. 8,979,928.

(60) Provisional application No. 61/335,947, filed on Jan. 13, 2010, provisional application No. 61/520,956, filed on Jun. 17, 2011.

(52) U.S. Cl.
CPC ............... *A61F 2002/30387* (2013.01); *A61F 2002/30622* (2013.01); *A61F 2002/30642* (2013.01); *A61F 2002/30879* (2013.01); *A61F 2002/30883* (2013.01); *A61F 2002/30995* (2013.01)

(58) Field of Classification Search
CPC . A61B 17/1671; A61B 17/68; A61B 17/8685; A61B 17/1664; A61B 17/846; A61B 17/844; A61B 17/8645; A61B 17/1739
See application file for complete search history.

(56) References Cited

U.S. PATENT DOCUMENTS

| | | |
|---|---|---|
| 4,590,928 A | 5/1986 | Hunt et al. |
| 4,622,959 A | 11/1986 | Marcus |
| 4,714,469 A | 12/1987 | Kenna |
| 4,773,402 A | 9/1988 | Asher et al. |
| 4,794,918 A | 1/1989 | Wolter |
| 4,863,476 A | 9/1989 | Shepperd |
| 4,881,535 A | 11/1989 | Sohngen |
| 4,911,153 A | 3/1990 | Border |
| 4,920,958 A | 5/1990 | Walt et al. |
| 4,950,270 A | 8/1990 | Bowman et al. |
| 5,026,373 A | 6/1991 | Ray et al. |
| 5,052,375 A | 10/1991 | Stark et al. |
| 5,108,397 A | 4/1992 | White |
| 5,112,337 A | 5/1992 | Paulos et al. |
| 5,176,681 A | 1/1993 | Lawes et al. |
| 5,192,327 A | 3/1993 | Brantigan |
| 5,242,444 A | 9/1993 | MacMillan |
| 5,282,861 A | 2/1994 | Kaplan |
| 5,334,192 A | 8/1994 | Behrens |
| 5,334,205 A | 8/1994 | Cain |
| 5,336,225 A | 8/1994 | Zang |
| 5,368,546 A | 11/1994 | Stark et al. |
| 5,368,593 A | 11/1994 | Stark |
| 5,437,674 A | 8/1995 | Worcel et al. |
| 5,443,509 A | 8/1995 | Boucher et al. |
| 5,456,267 A | 10/1995 | Stark |
| 5,480,402 A | 1/1996 | Kim |
| 5,484,389 A | 1/1996 | Stark et al. |
| 5,591,235 A | 1/1997 | Kuslich |
| 5,593,407 A | 1/1997 | Reis |
| 5,607,424 A | 3/1997 | Tropiano |
| 5,609,635 A | 3/1997 | Michelson |
| 5,609,636 A | 3/1997 | Kohrs et al. |
| 5,626,434 A | 5/1997 | Cook |
| 5,658,337 A | 8/1997 | Kohrs et al. |
| 5,669,909 A | 9/1997 | Zdeblick et al. |
| 5,688,284 A | 11/1997 | Chervitz et al. |
| 5,743,914 A | 4/1998 | Skiba |
| 5,772,594 A | 6/1998 | Barrick |
| 5,823,975 A | 10/1998 | Stark et al. |
| 5,888,224 A | 3/1999 | Beckers et al. |
| 5,891,150 A | 4/1999 | Chan |
| 5,919,193 A | 7/1999 | Slavitt |
| 5,928,239 A | 7/1999 | Mirza |
| 5,929,782 A | 7/1999 | Stark et al. |
| 5,993,463 A | 11/1999 | Truwit |
| 6,053,916 A | 4/2000 | Moore |
| 6,056,749 A | 5/2000 | Kuslich |
| 6,063,442 A | 5/2000 | Cohen et al. |
| 6,175,758 B1 | 1/2001 | Kambin |
| 6,184,797 B1 | 2/2001 | Stark et al. |
| 6,236,891 B1 | 5/2001 | Ingle et al. |
| 6,241,771 B1 | 6/2001 | Gresser et al. |
| 6,290,724 B1 | 9/2001 | Marino |
| 6,296,595 B1 | 10/2001 | Stark et al. |
| 6,302,885 B1 | 10/2001 | Essiger |
| 6,322,562 B1 | 11/2001 | Wolter |
| 6,371,123 B1 | 4/2002 | Stark et al. |
| 6,413,278 B1 | 7/2002 | Marchosky |
| 6,432,107 B1 | 8/2002 | Ferree |
| 6,432,140 B1 | 8/2002 | Lin |
| 6,515,593 B1 | 2/2003 | Stark et al. |
| 6,520,990 B1 | 2/2003 | Ray |
| 6,540,707 B1 | 4/2003 | Stark et al. |
| 6,547,795 B2 | 4/2003 | Schneiderman |
| 6,547,823 B2 | 4/2003 | Scarborough et al. |
| 6,558,423 B1 | 5/2003 | Michelson |
| 6,565,605 B2 | 5/2003 | Goble et al. |
| 6,572,622 B1 | 6/2003 | Schäfer et al. |
| 6,579,318 B2 | 6/2003 | Varga et al. |
| 6,607,487 B2 | 8/2003 | Chang et al. |
| 6,635,059 B2 | 10/2003 | Randall et al. |
| 6,641,614 B1 | 11/2003 | Wagner |
| 6,660,224 B2 | 12/2003 | Lefebvre et al. |
| 6,663,669 B1 | 12/2003 | Reiley |
| 6,669,698 B1 | 12/2003 | Tromanhauser et al. |
| 6,682,563 B2 | 1/2004 | Scharf |
| 6,682,567 B1 | 1/2004 | Schroeder |
| 6,716,245 B2 | 4/2004 | Pasquet et al. |
| 6,723,099 B1 | 4/2004 | Goshert |
| 6,743,256 B2 | 6/2004 | Mason |
| 6,746,451 B2 | 6/2004 | Middleton et al. |
| 6,824,564 B2 | 11/2004 | Crozet |
| 6,827,670 B1 | 12/2004 | Stark et al. |
| 6,835,208 B2 | 12/2004 | Marchosky |
| 6,855,166 B2 | 2/2005 | Kohrs |
| 6,855,167 B2 | 2/2005 | Shimp et al. |
| 6,860,902 B2 | 3/2005 | Reiley |
| 6,872,187 B1 | 3/2005 | Stark et al. |
| 6,875,236 B2 | 4/2005 | Reiley |
| 6,902,567 B2 | 6/2005 | Del Medico |
| 6,908,465 B2 | 6/2005 | von Hoffmann et al. |
| 6,945,448 B2 | 9/2005 | Medlin et al. |
| 6,972,019 B2 | 12/2005 | Michelson |
| 6,974,461 B1 | 12/2005 | Wolter |
| 7,011,660 B2 | 3/2006 | Sherman et al. |
| 7,087,056 B2 | 8/2006 | Vaughan |
| 7,087,058 B2 | 8/2006 | Cragg |
| 7,108,828 B2 | 9/2006 | Lefebvre et al. |
| 7,144,399 B2 | 12/2006 | Hayes et al. |
| 7,163,560 B2 | 1/2007 | Mason |
| 7,192,447 B2 | 3/2007 | Rhoda |
| 7,201,775 B2 | 4/2007 | Gorensek et al. |
| 7,208,222 B2 | 4/2007 | Rolfe et al. |
| 7,217,291 B2 | 5/2007 | Zucherman et al. |
| 7,229,448 B2 | 6/2007 | Goble et al. |
| 7,235,101 B2 | 6/2007 | Berry et al. |
| 7,235,105 B2 | 6/2007 | Jackson |
| 7,247,157 B2 | 7/2007 | Prager et al. |
| 7,255,712 B1 | 8/2007 | Steinberg |
| 7,303,563 B2 | 12/2007 | Poyner et al. |
| 7,331,995 B2 | 2/2008 | Eisermann et al. |
| 7,396,360 B2 | 7/2008 | Lieberman |
| 7,410,501 B2 | 8/2008 | Michelson |
| 7,416,537 B1 | 8/2008 | Stark et al. |
| 7,458,991 B2 | 12/2008 | Wang et al. |
| 7,465,317 B2 | 12/2008 | Malberg et al. |
| 7,520,898 B2 | 4/2009 | Re et al. |
| 7,537,616 B1 | 5/2009 | Branch et al. |
| 7,575,600 B2 | 8/2009 | Zucherman et al. |
| 7,621,939 B2 | 11/2009 | Zucherman et al. |
| 7,635,447 B2 | 12/2009 | Hamman et al. |
| 7,637,954 B2 | 12/2009 | Michelson |
| 7,641,697 B2 | 1/2010 | Reiley |
| 7,648,509 B2 | 1/2010 | Stark |

(56) References Cited

U.S. PATENT DOCUMENTS

| | | |
|---|---|---|
| 7,666,209 B2 | 2/2010 | Zucherman et al. |
| 7,670,383 B1 | 3/2010 | Brown et al. |
| 7,704,279 B2 | 4/2010 | Moskowitz et al. |
| 7,713,290 B2 | 5/2010 | Vaughan |
| 7,740,795 B2 | 6/2010 | Wang et al. |
| 7,771,441 B2 | 8/2010 | Cerundolo |
| 7,789,895 B2 | 9/2010 | Heinz |
| 7,794,465 B2 | 9/2010 | Marik et al. |
| 7,799,081 B2 | 9/2010 | McKinley |
| 7,819,869 B2 | 10/2010 | Godara et al. |
| 7,824,404 B2 | 11/2010 | Godara et al. |
| 7,837,732 B2 | 11/2010 | Zucherman et al. |
| 7,837,734 B2 | 11/2010 | Zucherman et al. |
| 7,846,162 B2 | 12/2010 | Nelson et al. |
| 7,850,690 B2 | 12/2010 | Frigg et al. |
| 7,850,719 B2 | 12/2010 | Gournay et al. |
| 7,850,732 B2 | 12/2010 | Heinz |
| 7,909,871 B2 | 3/2011 | Abdou |
| 7,918,891 B1 | 4/2011 | Curran et al. |
| 7,922,765 B2 | 4/2011 | Reiley |
| 7,963,970 B2 | 6/2011 | Marino et al. |
| 7,972,363 B2 | 7/2011 | Moskowitz et al. |
| 7,972,382 B2 | 7/2011 | Foley et al. |
| 7,985,255 B2 | 7/2011 | Bray et al. |
| 8,034,114 B2 | 10/2011 | Reiley |
| 8,034,115 B2 | 10/2011 | Reiley |
| 8,048,164 B2 | 11/2011 | Reiley |
| 8,070,782 B2 | 12/2011 | McKay |
| 8,075,561 B2 | 12/2011 | Wolter |
| 8,083,796 B1 | 12/2011 | Raiszadeh et al. |
| 8,088,163 B1 | 1/2012 | Kleiner |
| 8,128,666 B2 | 3/2012 | Falahee |
| 8,162,981 B2 | 4/2012 | Vestgaarden |
| 8,187,332 B2 | 5/2012 | McLuen |
| 8,202,305 B2 | 6/2012 | Reiley |
| 8,221,428 B2 | 7/2012 | Trieu |
| 8,231,661 B2 | 7/2012 | Carls et al. |
| 8,308,779 B2 | 11/2012 | Reiley |
| 8,308,794 B2 | 11/2012 | Martinson et al. |
| 8,317,862 B2 | 11/2012 | Troger et al. |
| 8,343,189 B2 * | 1/2013 | Assell .................. A61F 2/4405 606/246 |
| 8,343,219 B2 | 1/2013 | Allain et al. |
| 8,348,950 B2 | 1/2013 | Assell et al. |
| 8,388,667 B2 | 3/2013 | Reiley |
| 8,414,648 B2 | 4/2013 | Reiley |
| 8,425,570 B2 | 4/2013 | Reiley |
| 8,425,603 B2 | 4/2013 | Reichen et al. |
| 8,439,925 B2 | 5/2013 | Marino et al. |
| 8,444,693 B2 | 5/2013 | Reiley |
| 8,454,618 B2 | 6/2013 | Stark |
| 8,470,004 B2 | 6/2013 | Reiley |
| 8,470,037 B2 | 6/2013 | Re et al. |
| 8,480,755 B2 | 7/2013 | Reiley |
| 8,491,572 B2 | 7/2013 | Martinson et al. |
| 8,491,653 B2 | 7/2013 | Zucherman et al. |
| 8,496,712 B2 | 7/2013 | Reiley |
| 8,501,690 B2 | 8/2013 | Stark |
| 8,518,120 B2 | 8/2013 | Glerum |
| 8,551,171 B2 | 10/2013 | Johnson et al. |
| 8,579,912 B2 | 11/2013 | Isaza et al. |
| 8,585,744 B2 | 11/2013 | Duggal et al. |
| 8,623,062 B2 | 1/2014 | Kondrashov |
| 8,808,305 B2 | 8/2014 | Kleiner |
| 8,808,336 B2 | 8/2014 | Duggal et al. |
| 8,808,377 B2 | 8/2014 | Donner |
| 8,808,380 B2 | 8/2014 | Fox et al. |
| 8,808,389 B2 | 8/2014 | Reiley |
| 8,821,546 B2 | 9/2014 | Vaughan |
| 8,840,651 B2 | 9/2014 | Reiley |
| 8,894,708 B2 | 11/2014 | Thalgott et al. |
| 8,979,928 B2 | 3/2015 | Donner |
| 8,992,579 B1 | 3/2015 | Gustine et al. |
| 9,017,407 B2 | 4/2015 | Donner |
| 9,039,768 B2 | 5/2015 | Voellmicke |
| 9,333,090 B2 | 5/2016 | Donner et al. |
| 2001/0005796 A1 | 6/2001 | Zdeblick et al. |
| 2001/0018616 A1 | 8/2001 | Schwab |
| 2001/0020143 A1 | 9/2001 | Stark et al. |
| 2002/0029784 A1 | 3/2002 | Stark et al. |
| 2002/0032484 A1 | 3/2002 | Hyde, Jr. |
| 2002/0068941 A1 | 6/2002 | Hanson |
| 2002/0068977 A1 | 6/2002 | Jackson |
| 2002/0082701 A1 | 6/2002 | Zdeblick et al. |
| 2002/0087161 A1 | 7/2002 | Randall et al. |
| 2002/0147461 A1 | 10/2002 | Aldrich et al. |
| 2002/0147496 A1 | 10/2002 | Belef et al. |
| 2002/0183846 A1 | 12/2002 | Kuslich et al. |
| 2003/0114931 A1 | 6/2003 | Lee et al. |
| 2003/0124486 A1 | 7/2003 | McDevitt |
| 2003/0181981 A1 | 9/2003 | Lemaire |
| 2003/0208202 A1 | 11/2003 | Falahee |
| 2004/0073216 A1 | 4/2004 | Lieberman |
| 2004/0127988 A1 | 7/2004 | Goble et al. |
| 2004/0162558 A1 | 8/2004 | Hegde et al. |
| 2004/0162616 A1 | 8/2004 | Simonton |
| 2004/0186482 A1 | 9/2004 | Kolb et al. |
| 2004/0199256 A1 | 10/2004 | Wang |
| 2004/0220668 A1 | 11/2004 | Eisermann et al. |
| 2004/0228901 A1 | 11/2004 | Trieu |
| 2004/0249675 A1 | 12/2004 | Stark et al. |
| 2004/0260286 A1 * | 12/2004 | Ferree ...................... A61F 2/28 623/17.11 |
| 2005/0043660 A1 | 2/2005 | Stark et al. |
| 2005/0101887 A1 | 5/2005 | Stark et al. |
| 2005/0113652 A1 | 5/2005 | Stark et al. |
| 2005/0131539 A1 | 6/2005 | Kohrs |
| 2005/0149192 A1 | 7/2005 | Zucherman et al. |
| 2005/0154391 A1 | 7/2005 | Doherty et al. |
| 2005/0203515 A1 | 9/2005 | Doherty et al. |
| 2005/0216088 A1 | 9/2005 | McKinley et al. |
| 2005/0240264 A1 | 10/2005 | Tokish, Jr. et al. |
| 2005/0245925 A1 | 11/2005 | Iki et al. |
| 2005/0267482 A1 | 12/2005 | Hyde, Jr. |
| 2005/0273099 A1 | 12/2005 | Baccelli et al. |
| 2006/0054171 A1 | 3/2006 | Dall |
| 2006/0058876 A1 | 3/2006 | McKinley |
| 2006/0069438 A1 | 3/2006 | Zucherman et al. |
| 2006/0085068 A1 | 4/2006 | Barry |
| 2006/0089716 A1 | 4/2006 | Felix |
| 2006/0095134 A1 | 5/2006 | Trieu et al. |
| 2006/0129244 A1 | 6/2006 | Ensign |
| 2006/0147332 A1 | 7/2006 | Jones et al. |
| 2006/0161154 A1 | 7/2006 | McAfee |
| 2006/0167547 A1 | 7/2006 | Suddaby |
| 2006/0229729 A1 | 10/2006 | Gordon |
| 2007/0027543 A1 | 2/2007 | Gimble et al. |
| 2007/0055374 A1 | 3/2007 | Copf, Jr. et al. |
| 2007/0155588 A1 | 7/2007 | Stark et al. |
| 2007/0156241 A1 | 7/2007 | Reiley et al. |
| 2007/0162134 A1 | 7/2007 | Marnay et al. |
| 2007/0179621 A1 | 8/2007 | McClellan, III et al. |
| 2007/0198093 A1 | 8/2007 | Brodke et al. |
| 2007/0225714 A1 | 9/2007 | Gradl |
| 2007/0239164 A1 | 10/2007 | Prager et al. |
| 2007/0265621 A1 | 11/2007 | Matthis et al. |
| 2007/0270879 A1 | 11/2007 | Isaza et al. |
| 2007/0270968 A1 | 11/2007 | Baynham |
| 2007/0276501 A1 | 11/2007 | Betz et al. |
| 2007/0293949 A1 | 12/2007 | Salerni et al. |
| 2007/0299525 A1 | 12/2007 | Binotto |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0039843 A1 | 2/2008 | Abdou |
| 2008/0045968 A1 | 2/2008 | Yu et al. |
| 2008/0065215 A1 | 3/2008 | Reiley |
| 2008/0140082 A1 | 6/2008 | Erdem et al. |
| 2008/0140207 A1 | 6/2008 | Olmos |
| 2008/0154314 A1 | 6/2008 | McDevitt |
| 2008/0183293 A1 | 7/2008 | Parry et al. |
| 2008/0228276 A1 | 9/2008 | Mathews et al. |
| 2008/0262621 A1 | 10/2008 | Gorek |
| 2008/0281425 A1 | 11/2008 | Thalgott et al. |

(56) References Cited

U.S. PATENT DOCUMENTS

| | | |
|---|---|---|
| 2008/0288081 A1 | 11/2008 | Scrafton et al. |
| 2008/0300685 A1 | 12/2008 | Carls et al. |
| 2009/0018660 A1 | 1/2009 | Roush |
| 2009/0024174 A1 | 1/2009 | Stark |
| 2009/0024217 A1 | 1/2009 | Levy |
| 2009/0043394 A1 | 2/2009 | Zdeblick et al. |
| 2009/0076553 A1 | 3/2009 | Wolter |
| 2009/0088849 A1 | 4/2009 | Armstrong et al. |
| 2009/0105833 A1 | 4/2009 | Hovda et al. |
| 2009/0105834 A1 | 4/2009 | Hovda et al. |
| 2009/0131986 A1 | 5/2009 | Lee et al. |
| 2009/0132035 A1 | 5/2009 | Roth et al. |
| 2009/0138053 A1* | 5/2009 | Assell .................. A61F 2/4405 606/301 |
| 2009/0149957 A1 | 6/2009 | Burd et al. |
| 2009/0192621 A1 | 7/2009 | Winslow et al. |
| 2009/0216238 A1 | 8/2009 | Stark |
| 2009/0216276 A1 | 8/2009 | Pasquet |
| 2009/0248163 A1 | 10/2009 | King et al. |
| 2009/0259261 A1 | 10/2009 | Reiley |
| 2009/0259316 A1 | 10/2009 | Ginn et al. |
| 2009/0287254 A1 | 11/2009 | Nayet et al. |
| 2009/0306671 A1 | 12/2009 | McCormack et al. |
| 2010/0057204 A1 | 3/2010 | Kadaba |
| 2010/0094290 A1 | 4/2010 | Vaidya |
| 2010/0100135 A1 | 4/2010 | Phan |
| 2010/0106200 A1 | 4/2010 | Stark |
| 2010/0121160 A1 | 5/2010 | Stark et al. |
| 2010/0137910 A1 | 6/2010 | Cawley et al. |
| 2010/0137919 A1 | 6/2010 | Wolter |
| 2010/0152785 A1 | 6/2010 | Forton et al. |
| 2010/0179552 A1 | 7/2010 | Wolter |
| 2010/0185292 A1* | 7/2010 | Hochschuler ......... A61F 2/4455 623/17.16 |
| 2010/0204795 A1 | 8/2010 | Greenhalgh |
| 2010/0211176 A1 | 8/2010 | Greenhalgh |
| 2010/0268228 A1 | 10/2010 | Petersen |
| 2010/0286779 A1 | 11/2010 | Thibodeau |
| 2010/0286785 A1 | 11/2010 | Grayson |
| 2010/0292796 A1 | 11/2010 | Greenhalgh |
| 2010/0292800 A1 | 11/2010 | Zubok |
| 2010/0305702 A1 | 12/2010 | Michelson |
| 2010/0305704 A1 | 12/2010 | Messerli |
| 2010/0324607 A1 | 12/2010 | Davis |
| 2010/0331981 A1 | 12/2010 | Mohammed |
| 2011/0034957 A1 | 2/2011 | Biedermann |
| 2011/0046737 A1 | 2/2011 | Teisen |
| 2011/0071568 A1 | 3/2011 | Ginn et al. |
| 2011/0071635 A1 | 3/2011 | Zhang et al. |
| 2011/0087294 A1 | 4/2011 | Reiley |
| 2011/0093074 A1 | 4/2011 | Glerum |
| 2011/0098816 A1 | 4/2011 | Jacob et al. |
| 2011/0098817 A1* | 4/2011 | Eckhardt ............ A61B 17/7055 623/17.11 |
| 2011/0118796 A1 | 5/2011 | Reiley |
| 2011/0172774 A1 | 7/2011 | Varela |
| 2011/0184518 A1 | 7/2011 | Trieu |
| 2011/0184519 A1 | 7/2011 | Trieu |
| 2011/0184520 A1 | 7/2011 | Trieu |
| 2011/0185961 A1 | 7/2011 | Aravamudan |
| 2011/0230966 A1 | 9/2011 | Trieu |
| 2011/0238181 A1 | 9/2011 | Trieu |
| 2011/0264229 A1 | 10/2011 | Donner |
| 2011/0264233 A1 | 10/2011 | Song |
| 2011/0295272 A1 | 12/2011 | Assell et al. |
| 2012/0010714 A1 | 1/2012 | Moskowitz et al. |
| 2012/0022535 A1 | 1/2012 | Mayer et al. |
| 2012/0022595 A1 | 1/2012 | Pham et al. |
| 2012/0029641 A1 | 2/2012 | Curran et al. |
| 2012/0035729 A1 | 2/2012 | Glerum |
| 2012/0083883 A1 | 4/2012 | Ginn |
| 2012/0095560 A1 | 4/2012 | Donner |
| 2012/0116454 A1 | 5/2012 | Edidin et al. |
| 2012/0116806 A1 | 5/2012 | Stark et al. |
| 2012/0150300 A1 | 6/2012 | Nihalani |
| 2012/0185049 A1 | 7/2012 | Varela |
| 2012/0209388 A1 | 8/2012 | Curran et al. |
| 2012/0253398 A1 | 10/2012 | Metcalf et al. |
| 2012/0259370 A1 | 10/2012 | Vaidya |
| 2012/0271200 A1 | 10/2012 | Martinson et al. |
| 2012/0271424 A1 | 10/2012 | Crawford |
| 2012/0296428 A1 | 11/2012 | Donner |
| 2012/0316565 A1 | 12/2012 | Stark |
| 2012/0323285 A1 | 12/2012 | Assell et al. |
| 2013/0006361 A1 | 1/2013 | Glerum |
| 2013/0018427 A1 | 1/2013 | Pham et al. |
| 2013/0023994 A1 | 1/2013 | Glerum |
| 2013/0030456 A1 | 1/2013 | Assell et al. |
| 2013/0035723 A1 | 2/2013 | Donner |
| 2013/0035727 A1 | 2/2013 | Datta |
| 2013/0053854 A1 | 2/2013 | Schoenefeld et al. |
| 2013/0053902 A1 | 2/2013 | Trudeau |
| 2013/0053964 A1 | 2/2013 | Talwar |
| 2013/0060337 A1 | 3/2013 | Petersheim et al. |
| 2013/0066426 A1 | 3/2013 | Martinson et al. |
| 2013/0085535 A1 | 4/2013 | Greenhalgh et al. |
| 2013/0090735 A1 | 4/2013 | Mermuys et al. |
| 2013/0116790 A1 | 5/2013 | Seifert |
| 2013/0123923 A1 | 5/2013 | Pavlov et al. |
| 2013/0144343 A1 | 6/2013 | Arnett et al. |
| 2013/0158669 A1 | 6/2013 | Sungarian |
| 2013/0197590 A1 | 8/2013 | Assell et al. |
| 2013/0218215 A1 | 8/2013 | Ginn et al. |
| 2013/0226181 A1 | 8/2013 | Assell et al. |
| 2013/0231746 A1 | 9/2013 | Ginn et al. |
| 2013/0245764 A1* | 9/2013 | Mauldin ............. A61F 2/30988 623/17.11 |
| 2013/0253650 A1 | 9/2013 | Ashley |
| 2013/0282012 A1 | 10/2013 | Stark |
| 2013/0295202 A1 | 11/2013 | Stark |
| 2013/0297035 A1 | 11/2013 | Reiley |
| 2014/0012330 A1 | 1/2014 | Johnson, II et al. |
| 2014/0039628 A1 | 2/2014 | DeLurio et al. |
| 2014/0088707 A1 | 3/2014 | Donner et al. |
| 2014/0135850 A1 | 5/2014 | Parent et al. |
| 2014/0200618 A1 | 7/2014 | Donner et al. |
| 2014/0249581 A1 | 9/2014 | Stachniak |
| 2014/0336775 A1 | 11/2014 | Reiley |
| 2015/0039037 A1 | 2/2015 | Donner et al. |
| 2015/0094765 A1 | 4/2015 | Donner et al. |
| 2015/0150683 A1 | 6/2015 | Donner et al. |
| 2015/0182268 A1 | 7/2015 | Donner et al. |
| 2015/0209087 A1 | 7/2015 | Donner et al. |
| 2015/0342753 A1 | 12/2015 | Donner et al. |
| 2016/0184105 A1 | 6/2016 | Donner et al. |
| 2016/0278818 A1 | 9/2016 | Donner et al. |
| 2016/0324643 A1 | 11/2016 | Donner et al. |

FOREIGN PATENT DOCUMENTS

| | | |
|---|---|---|
| CN | 201073333 Y | 6/2008 |
| CN | 201139628 | 10/2008 |
| CN | 201275132 | 7/2009 |
| CN | 201275133 | 7/2009 |
| CN | 201275134 | 7/2009 |
| CN | 202235633 U | 5/2012 |
| EP | 1663037 B1 | 6/2006 |
| JP | 2007-275592 | 10/2007 |
| KR | 10-1037206 | 5/2011 |
| RU | 2364359 C1 | 8/2009 |
| WO | WO 93/08745 A1 | 5/1993 |
| WO | WO 95/23559 | 9/1995 |
| WO | WO 95/31947 | 11/1995 |
| WO | WO 98/48717 | 11/1998 |
| WO | WO 01/30264 A2 | 5/2001 |
| WO | WO 01/95823 A1 | 12/2001 |
| WO | WO 02/067759 A2 | 9/2002 |
| WO | WO 02/085182 A2 | 10/2002 |
| WO | WO 2006/020463 A1 | 2/2006 |
| WO | WO 2006/099270 | 9/2006 |
| WO | WO 2007/022790 A1 | 3/2007 |
| WO | WO 2007/115295 A2 | 10/2007 |
| WO | WO 2008/011410 A2 | 1/2008 |
| WO | WO 2008/088685 A2 | 7/2008 |

(56) References Cited

FOREIGN PATENT DOCUMENTS

| | | |
|---|---|---|
| WO | WO 2008/089537 A1 | 7/2008 |
| WO | WO 2009/011774 A2 | 1/2009 |
| WO | WO 2009/029074 A1 | 3/2009 |
| WO | WO 2009/108318 A2 | 9/2009 |
| WO | WO 2010/045749 A1 | 4/2010 |
| WO | WO 2010/065015 A1 | 6/2010 |
| WO | WO 2010/108166 A1 | 9/2010 |
| WO | WO 2011014135 A2 | 2/2011 |
| WO | WO 2011/056690 A2 | 5/2011 |
| WO | WO 2011/066053 A2 | 6/2011 |
| WO | WO 2011/087912 A1 | 7/2011 |
| WO | WO 2011/091349 A2 | 7/2011 |
| WO | WO 2012/015976 A1 | 2/2012 |
| WO | WO 2013/020123 A2 | 2/2013 |
| WO | WO 2013/043584 A1 | 3/2013 |

OTHER PUBLICATIONS

Medtronic Sofamor Danek. Colorado 2™ The New Revolution, Surgical Technique. © 2000 Medtronic Sofamor Danek, Inc.
Synthes GmbH. Sacral Bars. Fixation of the posterior pelvis in cases of fractures or sacroiliac joint dislocations. © Apr. 2009 Synthes, Inc.
Tenon Medical, *Catamaran SI Joint Implant*, http://tctig.com/projects (last visited Nov. 19, 2014).
Amendment Under 1.312, U.S. Appl. No. 13/475,695, dated Mar. 25, 2016.
Amendment Under 1.312, U.S. Appl. No. 13/945,053, dated May 19, 2016.
Amendment Under 1.312, U.S. Appl. No. 13/946,790, dated Dec. 14, 2015.
Australian Examination Report, AU2014204494, dated May 15, 2015.
Chinese Office Action, CN201180001537.4, dated Mar. 19, 2015.
EP Examination Report, EP11733183.5, dated Sep. 9, 2015.
European Search Report, EP Appl. No. 12799773.2, dated Oct. 29, 2014.
European Search Report, EP12834000.7, dated Jul. 13, 2015.
Examination Report, SG Application No. 201205104-1, dated Jul. 17, 2014, Intellectual Property Office of Singapore.
Final Rejection, U.S. Appl. No. 13/236,411, dated Jan. 2, 2015.
Final Rejection, U.S. Appl. No. 13/945,053, dated Dec. 22, 2015.
International Search Report and Written Opinion, PCT/US2014/048990, dated Nov. 18, 2014.
Japanese Office Action, JP2012-548960, dated Oct. 7, 2014.
Japanese Office Action, JP2015-042238, dated Dec. 22, 2015.
Non-Final Office Action, U.S. Appl. No. 13/945,053, dated Apr. 3, 2015.
Non-Final Office Action, U.S. Appl. No. 13/475,695, dated Jul. 30, 2015.
Non-Final Office Action, U.S. Appl. No. 14/413,318, dated May 3, 2016.
Non-Final Office Action, U.S. Appl. No. 14/567,956, dated Feb. 12, 2016.
Notice of Allowance, U.S. Appl. No. 13/236,411, dated Mar. 16, 2015.
Notice of Allowance, U.S. Appl. No. 12/998,712, dated Dec. 23, 2014.
Notice of Allowance, U.S. Appl. No. 13/475,695, dated Feb. 18, 2016.
Notice of Allowance, U.S. Appl. No. 13/945,053, dated Mar. 28, 2016.
Notice of Allowance, U.S. Appl. No. 13/946,790, dated Nov. 20, 2015.
Notice of Allowance, U.S. Appl. No. 13/946,790, dated Feb. 16, 2016.
Response to Final Office Action, U.S. Appl. No. 13/236,411, dated Mar. 4, 2015.
Response to Non-Final Office Action, U.S. Appl. No. 13/475,695, dated Oct. 30, 2015.
Response to Non-Final Office Action, U.S. Appl. No. 13/945,053, dated Aug. 31, 2015.
Response to Non-Final Office Action, U.S. Appl. No. 14/567,956, dated May 10, 2016.
Response to Restriction, U.S. Appl. No. 13/946,790, dated Sep. 14, 2015.
Response to Restriction, U.S. Appl. No. 13/945,053, dated Nov. 19, 2014.
Response to Restriction, U.S. Appl. No. 13/475,695, dated Jun. 30, 2015.
Response to Restriction, U.S. Appl. No. 14/216,975, dated Jan. 22, 2016.
Response to Restriction, U.S. Appl. No. 14/413,318, dated Apr. 19, 2016.
Response to Restriction, U.S. Appl. No. 14/567,956, dated Jan. 19, 2016.
Restriction Requirement, U.S. Appl. No. 13/475,695, dated Mar. 30, 2015.
Restriction Requirement, U.S. Appl. No. 13/946,790, dated Jul. 14, 2015.
Restriction Requirement, U.S. Appl. No. 13/945,053, dated Sep. 25, 2014.
Restriction Requirement, U.S. Appl. No. 14/216,975, dated Oct. 23, 2015.
Restriction Requirement, U.S. Appl. No. 14/413,318, dated Feb. 19, 2016.
Restriction Requirement, U.S. Appl. No. 14/567,956, dated Nov. 20, 2015.
Taiwan Examination Report, TW100114376, dated Oct. 5, 2015.
U.S. Appl. No. 14/447,612, filed Jul. 31, 2014, JCBD, LLC.
International Search Report and Written Opinion, PCT Application No. PCT/US2012/042823, dated Nov. 5, 2012, 16 pages.
Arman et al. The Human Sacrum and Safe Approaches for Screw Placement. *Journal of Clinical Neuroscience* 2008 Elsevier Inc.;16(2009):1046-1049.
Atlihan et al. Anatomy of the Posterior Illiac Crest as a Reference to Sacral Bar Insertion. *Clin Orthop* 2004;418:141-145.
Baria, Dinah, "Sacroiliac Joint Biomechanics and Effects of Fusion" (2010). Open Access Dissertations. Paper 466. http://scholarlyrepository.miami.edu/oa_dissertations, 179 pages.
Belanger, et al. "Sacroiliac Arthrodesis Using a Posterior Midline Fascial Splitting Approach and Pedicle Screw Instrumentation: A New Technique." Journal of Spinal Disorders, vol. 14 No. 2, pp. 118-124, 2001.
Buchowski, et al. "Functional and Radiographic Outcome of Sacroiliac Arthrodesis for the Disorders of the Sacroiliac Joint." The Spine Journal, 5, 2005, pp. 520-528.
Cecil et al. Projection of the S2 Pedicle Onto the Posterolateral Surface of the Ilium: A Technique for Lag Screw Fixation, Sacral Fractures or Sacroiliac Joint Dislocations. *Spine* 1996;21(7):875-878.
Chang et al. Low Profile Pelvic Fixation. *Spine* 2009;34(5):436-440.
Dayer R. et al. Pelvic fixation for neuromuscular scoliosis deformity correction. *Curr Rev Musculoskelet Med* (2012) 5:91-101.
DePuy Spine. ISOLA® Spinopelvic System, Surgical Technique. c. 2003 DePuy Spine, Inc., 28 pages.
Ebraheim, et al. "A Posterior Approach for Inspection of Reduction of Sacroiliac Joint Disruption." Surg. Radiol. Anat., 1999, 21(5), pp. 305-307.
Ebraheim, et al. "Anatomic considerations for Posterior Approach to the Sacroiliac Joint." Spine, 21(23), Dec. 1, 1996, pp. 2709-2712.
Garrido B.J. et al. Navigated placement of iliac bolts: description of a new technique. *The Spine Journal* 11 (2011) 331-335.
Giannikas, et al. "Sacroiliac Joint Fusion for Chronic Pain: A Simple Technique Avoiding the Use of Metalwork." Eur. Spine J, 13, 2004, pp. 253-256.
Globus Medical. REVERE® ADDITION® Sacroiliac Components, Surgical Technique. c. 2012 Globus Medical, 64 pages.
Globus Medical. SI-LOK™ Sacroiliac Joint Fixation System, Surgical Technique. c. 2011 Globus Medical, 44 pages.

(56) References Cited

OTHER PUBLICATIONS

Guner, et al. "Anterior Sacroiliac Fusion. A New Video-Assisted Endoscopic Technique." Surgical Laparoscopy & Endoscopy, 8(3), pp. 233-236.
LDR. Avenue® L Lateral Lumbar Cage. Sep. 2011, 3 pages.
LDR. ROI-A™ Anterior Approach Implant. Apr. 2008, 2 pages.
LDR. Surgical Technique ROI-C™ Anterior Cervical Cage. Apr. 2010, 15 pages.
Lee et al. Trajectory of Transsacral Iliac Screw for Lumbopelvic Fixation. *J Spinal Disord Tech* 2011;24(3):151-156.
Lehman, Jr. et al. Advantage of Pedicle Screw Fixation Directed Into the Apex of the Sacral Promontory Over Bicortical Fixation. *Spine* 2002;27(8):806-811.
Liebergall, Meir (Iri) M.D., *Lumbosacral and Spinopelvic Fixation*, Lippincott-Raven, Philadelphia, PA, 1996, Chap. 48, "Sacroiliac Joint Fusion," pp. 611-618.
Luk et al. A Stronger Bicortical Sacral Pedicle Screw Fixation Through the S1 Endplate. *Spine* 2005;30(5):525-529.
Margulies, J.Y. et al., *Movement, Stability & Low Back Pain, The essential role of the pelvis*, Churchill Livingstone, London, 1997, Chapters 44-47, "Surgical Fusion of the Spine to the Sacrum, etc.," pp. 555-593.
Marotta N. et al. A novel minimally invasive presacral approach and instrumentation technique for anterior L5-S1 intervertebral disectomy and fusion. *Neurosurg Focus*, vol. 20, Jan. 2006, 8 pages.
Martin et al. Sacropelvic Fixation: Two Case Reports of a New Percutaneous Technique. *Spine* 2011;36(9):E618-21.
McLauchlan, et al. "Sacral and Iliac Articular Cartilage Thickness and Cellularity: Relationship to Subchrondral Bone End-Plate Thickness and Cancellous Bone Density." Rheumatology 2002; 41:375-380.
Mendel et al. The Lateral Sacral Triangle—A Decision Support for Secure Transverse Sacroiliac Screw Insertion. *Injury J. Care Injured* 2010;42(2011):1164-1170.
Moshirfar et al. Pelvic Fixation in Spine Surgery. *The Journal of Bone & Joint Surgery* 2005;87-A(2 Suppl):89-106.
O'Brien et al. An Anatomic Study of the S2 Iliac Technique for Lumbopelvic Screw Placement. *Spine* 2009;34(12):E439-E442.
O'Brien et al. Feasibility of Minimally Invasive Sacropelvic Fixation. *Spine* 2010;35(4):460-464.
O'Brien et al. Sacropelvic Instrumentation: Anatomic and Biomechanical Zones of Fixation. *Seminars in Spine Surgery* 2004;16(2):76-90.
Ouellet et al. Surgical Anatomy of the Pelvis, Sacrum, and Lumbar Spine Relevant to Spinal Surgery. *Seminars in Spine Surgery* 2004 Elsevier Inc.;16:91-100.
Pan W. et al. The invention of an iliosacral screw fixation guide and its preliminary clinical application. *Orthopaedic Surgery* (2012), vol. 4, No. 1, pp. 55-59.
Puhakka, et al. "MR Imaging of the Normal Sacroiliac Joint with Correlation to Histology." Skeletal Radiol., 33, 2004, pp. 15-28.
SI-BONE iFuse Implant System, Surgical Technique Manual. c. 2011 SI-BONE, Inc., 35 pages.
SI-BONE iFuse Implant System™. SI-BONE, Inc. 2010, 4 pages.
Signus Medizintechnik GmbH. DIANA Operationstechnik. Rev. May 1, 2010, 20 pages.
Sponseller P.D. et al. Low profile pelvic fixation with the sacral alar iliac technique in the pediatric population improves results at two-year mninimum follow-up. *Spine* vol. 35, No. 20, pp. 1887-1892.
Stark J. G. et al. The history of sacroiliac joint arthrodesis: a critical review and introduction of a new technique. *Current Orthopaedic Practice*, vol. 22, No. 6, Nov./Dec. 2011, pp. 545-557.
Stark. "The Diagnosis and Treatment of Sacroiliac Joint Abnormalities." Current Orthopedic Practice, 21(4), Jul./Aug. 2010, pp. 336-347.
Synthes Spine. ProDisc-C Total Disc Replacement. Product Information. © 2008 Synthes, Inc., 14 pages.
Synthes Spine. SynFix-LR System. Instruments and implants for stand-alone anterior lumbar interbody fusion (ALIF). Technique Guide. © 2008 Synthes, Inc., 45 pages.
Synthes Spine. Universal Spinal System (USS) Polyaxial and Iliosacral Spine Fixation. A versatile system for posterior stabilization of spinal segments. Technique Guide, c. 2009 Synthes, Inc., 61 pages.
Szadek, et al. "Possible Nociceptive Structures in the Sacroiliac Joint Cartilage: An Immunohistochemical Study." Clinical Anatomy, 23, 2010, pp. 192-198.
tifix® Technology Pressure Plate. Technology: Multidirectional Locking Technology Titanium Plate and Screw Systems, General & Specific Instructions. litos/GmbH & Co. KG, Rev: Sep. 9, 2008.
Tobler W.D. et al. The presacral retroperitoneal approach for axial lumbar interbody fusion. *J Bone Joint Surg [Br]*, vol. 93-B, No. 7, Jul. 2011, pp. 955-960.
Ugur, et al. "New Needle Holder Facilitates Percutaneous Fluoroscopy-Guided Sacroiliac Puncture." Acta Radiologica, 2006, 47(5), pp. 481-483.
Vanelderen, et al. "Evidence-Based Medicine. Evidence-Based Interventional Pain Medicine According to Clinical Diagnoses. 13. Sacroiliac Joint Pain." Pain Practice, 10(5), 2010, pp. 470-478.
Waisbrod, et al. "Sacroiliac Joint Arthrodesis for Chronic Lower Back Pain." Arch. Orthop. Trauma Surg., 106, 1987, pp. 238-240.
Wise, et al. "Minimally Invasive Sacroiliac Arthrodesis. Outcomes of a New Technique." Spinal Disord. Tech., 21(8), Dec. 2008, pp. 579-584.
Yin, et al. "Sensory Stimulation-Guided Sacroiliac Joint Radiofrequency Neurotomy: Technique Based on Neuroanatomy of the Dorsal Sacral Plexus." Spine, 28(20), pp. 2419-2425.
Zyga Technology, Inc. Slmmetry Sacroiliac Joint Fusion System, Surgeon Didactic, c. 2012 Zyga Technology, Inc., 45 pages.
Zyga Technology, Inc. Slmmetry Sacroiliac Joint Fusion System, Technique Guide, known at least as early as Mar. 1, 2013, 20 pages.
Advisory Action, U.S. Appl. No. 12/998,712, dated Jan. 28, 2014, 4 pages.
Advisory Action, U.S. Appl. No. 13/135,381, mailed Jul. 23, 2013, 3 pages.
Appeal Brief, U.S. Appl. No. 13/135,381, dated Dec. 23, 2013, 20 pages.
European Search Report, EP Appl. No. 11733183.5, dated Dec. 18, 2013, 4 pages.
Final Rejection, U.S. Appl. No. 12/998,712, mailed Nov. 7, 2013, 24 pages.
Final Rejection, U.S. Appl. No. 13/135,381, mailed May 9, 2013, 14 pages.
International Search Report and Written Opinion, PCT Application No. PCT/US2012/055892, dated Mar. 25, 2013, 22 pages.
International Search Report and Written Opinion, PCT application No. PCT/US2011/000070, dated Mar. 21, 2011, 13 pages.
International Search Report and Written Opinion, PCT Application No. PCT/US2013/051381, dated Nov. 4, 2013, 16 pages.
International Search Report and Written Opinion, PCT/US2014/030889, dated Jul. 16, 2014.
Non-Final Office Action, U.S. Appl. No. 12/998,712, mailed May 31, 2013, 44 pages.
Non-Final Office Action, U.S. Appl. No. 12/998,712, dated Aug. 1, 2014.
Non-Final Office Action, U.S. Appl. No. 13/135,381, mailed Nov. 5, 2012, 19 pages.
Non-Final Office Action, U.S. Appl. No. 13/236,411, dated Apr. 11, 2014.
Notice of Allowance, U.S. Appl. No. 13/135,381, dated Apr. 17, 2014.
Response to Advisory Action, U.S. Appl. No. 13/135,381, filed Aug. 20, 2013, 12 pages.
Response to Final Office Action, U.S. Appl. No. 12/998,712, dated Jan. 7, 2014, 16 pages.
Response to Final Office Action, U.S. Appl. No. 13/135,381, filed Jul. 9, 2013, 11 pages.
Response to Non-Final Office Action, U.S. Appl. No. 13/135,381, filed Feb. 4, 2013, 7 pages.

(56) References Cited

OTHER PUBLICATIONS

Response to Non-Final Office Action, U.S. Appl. No. 12/998,712, filed Aug. 28, 2013, 17 pages.
Response to Non-Final Office Action, U.S. Appl. No. 12/998,712, dated Sep. 4, 2014.
Response to Non-Final Office Action, U.S. Appl. No. 13/236,411, dated Sep. 11, 2014.
Response to Restriction, U.S. Appl. No. 13/236,411, filed Jun. 10, 2013,13 pages.
Response to Restriction, U.S. Appl. No. 13/236,411, filed Nov. 12, 2013, 14 pages.
Restriction Requirement, U.S. Appl. No. 13/236,411, mailed May 10, 2013, 5 pages.
Restriction Requirement, U.S. Appl. No. 13/236,411, mailed Oct. 16, 2013, 7 pages.
Singapore Search Report and Written Opinion, SG Appl. No. 201205104-1, dated Oct. 31, 2013, 29 pages.
Supplemental Amendment, U.S. Appl. No. 12/998,712, dated Apr. 14, 2014, 14 pages.
Amendment and Response to Restriction, U.S. Appl. No. 14/447,612, dated Sep. 2, 2016.
AU Patent Examination Report No. 1, AU2012312658, dated Jul. 18, 2016.
Non-Final Office Action, U.S. Appl. No. 14/216,975, dated Jun. 20, 2016.
Non-Final Office Action, U.S. Appl. No. 14/344,876, dated Dec. 1, 2016.
Non-Final Office Action, U.S. Appl. No. 14/447,612, dated Dec. 15, 2016.
Non-Final Office Action, U.S. Appl. No. 14/681,882, dated Oct. 6, 2016.
Notice of Allowance, U.S. Appl. No. 13/945,053, dated Jul. 5, 2016.
Notice of Allowance, U.S. Appl. No. 14/413,318, dated Aug. 31, 2016.
Notice of Allowance, U.S. Appl. No. 14/567,956, dated Sep. 13, 2016.
Response to Non-Final Office Action, U.S. Appl. No. 14/413,318, dated Aug. 3, 2016.
Response to Restriction, U.S. Appl. No. 14/344,876, dated Aug. 29, 2016.
Response to Restriction, U.S. Appl. No. 14/514,221, dated Oct. 24, 2016.
Restriction Requirement, U.S. Appl. No. 14/447,612, dated Jul. 6, 2016.
Restriction Requirement, U.S. Appl. No. 14/514,221, dated Aug. 25, 2016.
Amendment with RCE, U.S. Appl. No. 14/567,956, dated Dec. 9, 2016.
Canadian Office Action, CA2787152, dated Jan. 25, 2017.
Chinese Office Action, CN201510622898.0, dated Dec. 23, 2016.
EP Extended Search Report, EP16191003.9, dated Feb. 6, 2017.
Final Office Action, U.S. Appl. No. 14/216,975, dated Dec. 30, 2016.
Notice of Allowance, U.S. Appl. No. 14/447,612, dated Feb. 28, 2017.
Notice of Allowance, U.S. Appl. No. 14/514,221, dated Feb. 21, 2017.
Notice of Allowance, U.S. Appl. No. 14/567,956, dated Mar. 13, 2017.
Response to Final Office Action, U.S. Appl. No. 14/216,975, dated Feb. 27, 2017.
Response to Non-Final Office Action, U.S. Appl. No. 14/344,876, dated Mar. 1, 2017.
Response to Non-Final Office Action, U.S. Appl. No. 14/447,612, dated Jan. 25, 2017.
Response to Non-Final Office Action, U.S. Appl. No. 14/681,882, dated Jan. 5, 2017.
Response to Restriction, U.S. Appl. No. 14/723,384, dated Feb. 24, 2017.
Restriction Requirement, U.S. Appl. No. 14/723,384, dated Dec. 29, 2016.

* cited by examiner

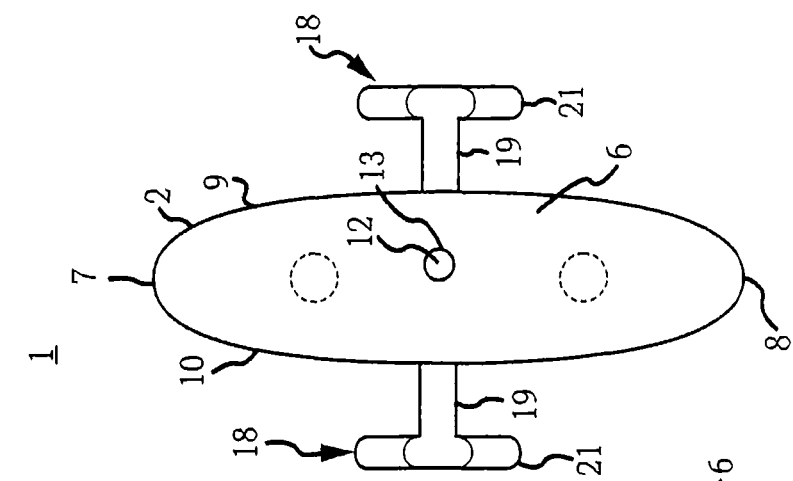
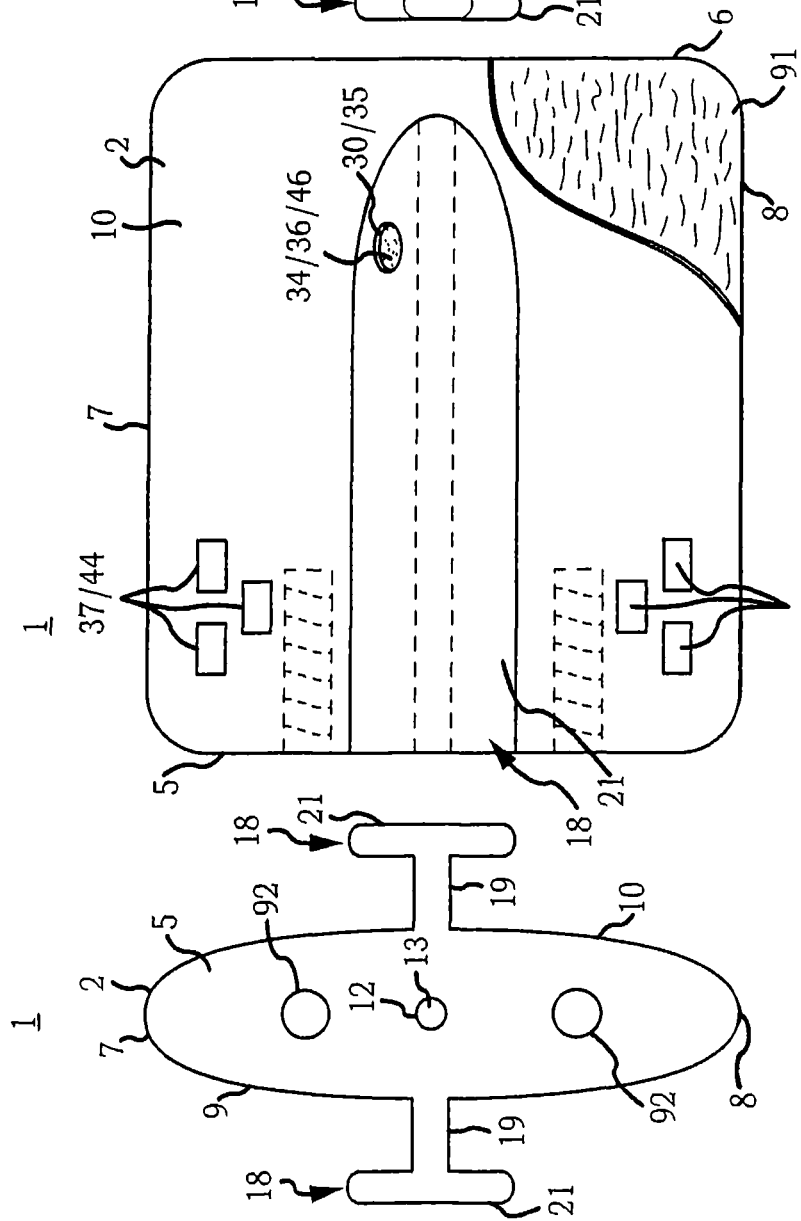
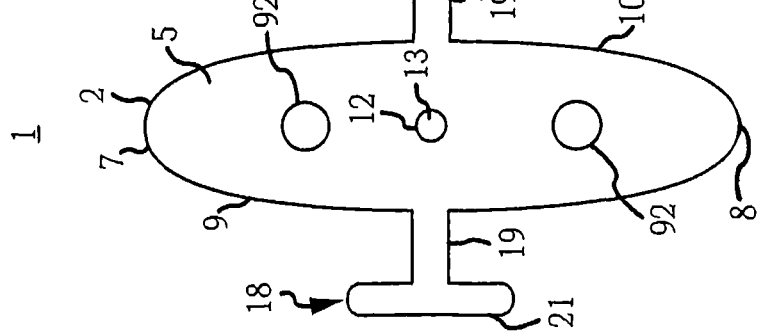

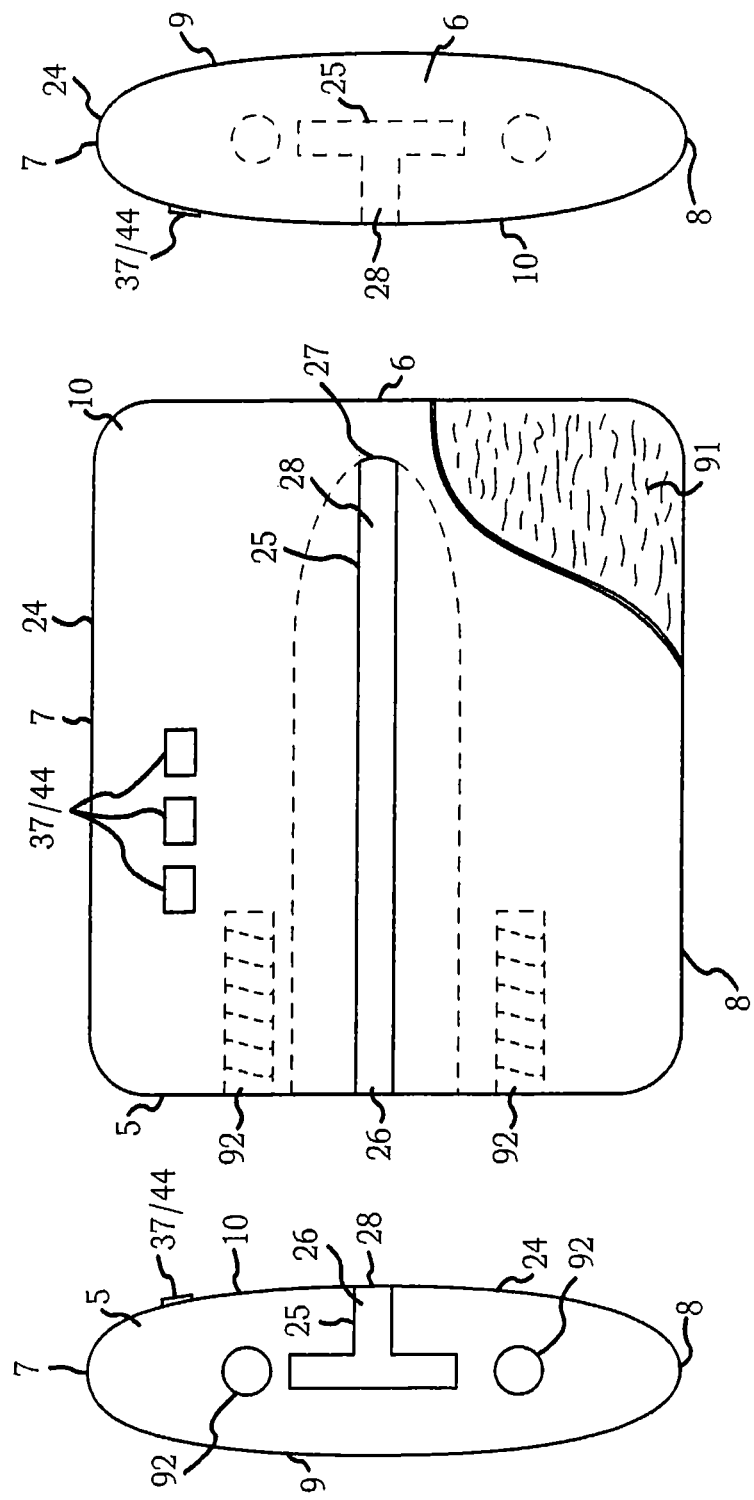

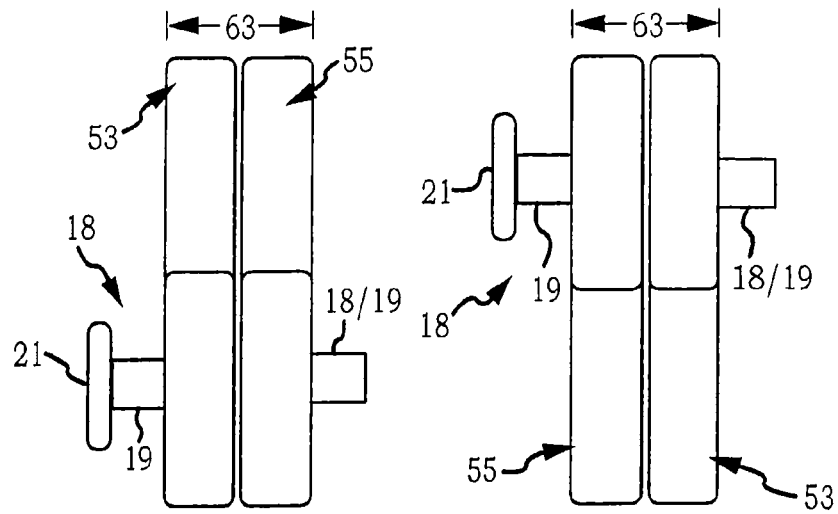
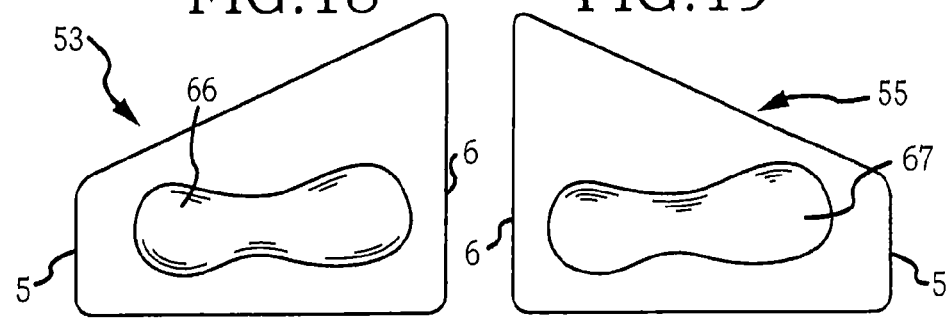
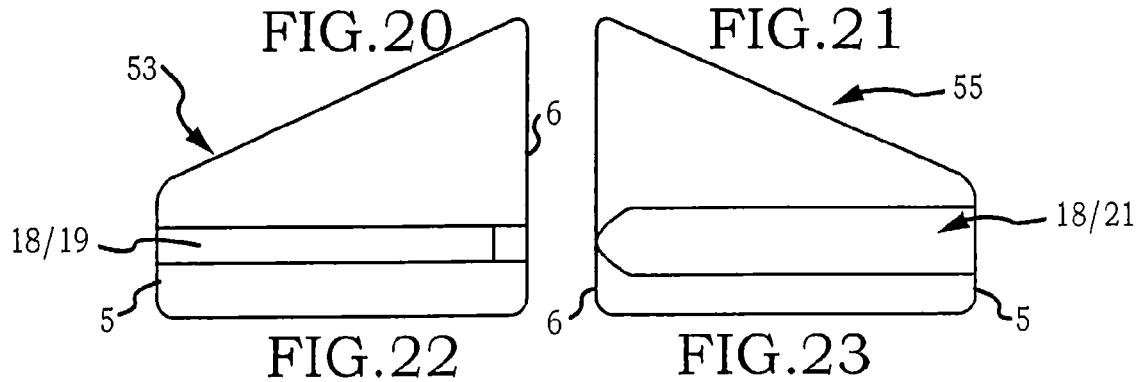
FIG. 18  FIG. 19  FIG. 20  FIG. 21  FIG. 22  FIG. 23

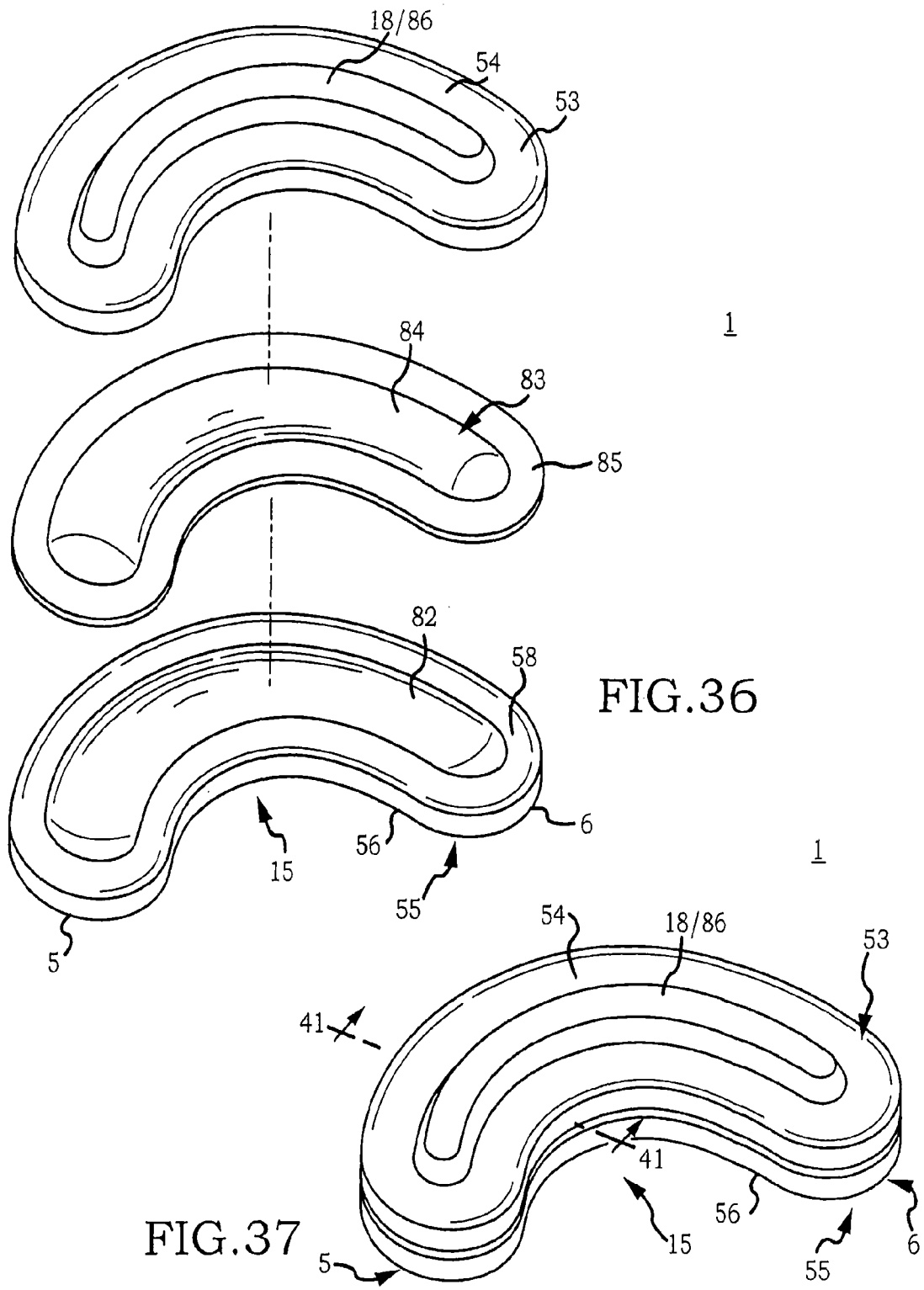

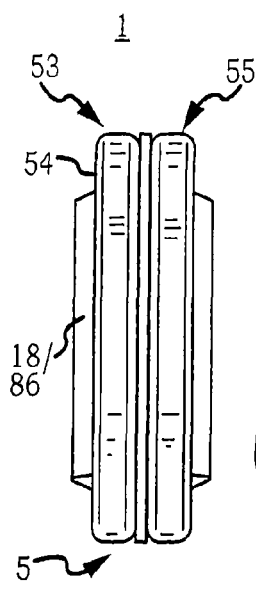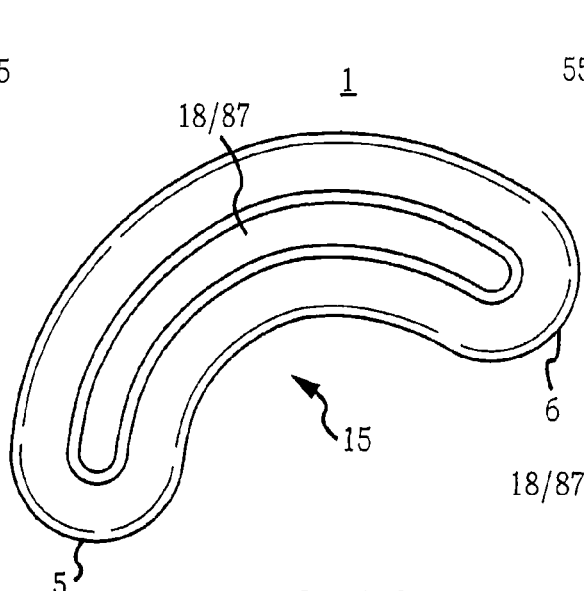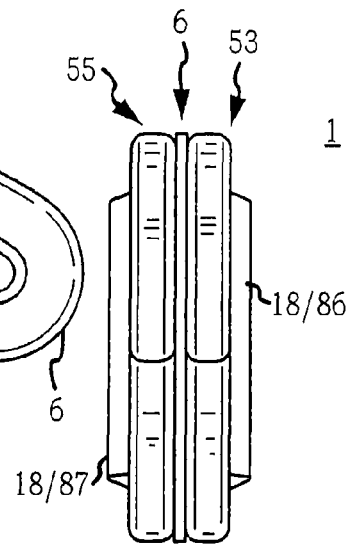
FIG.38  FIG.39  FIG.40
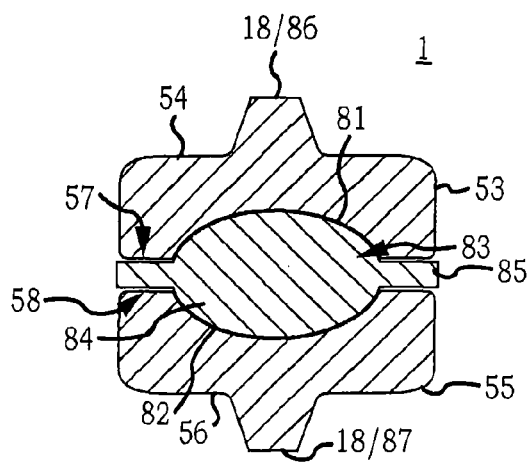
FIG.41

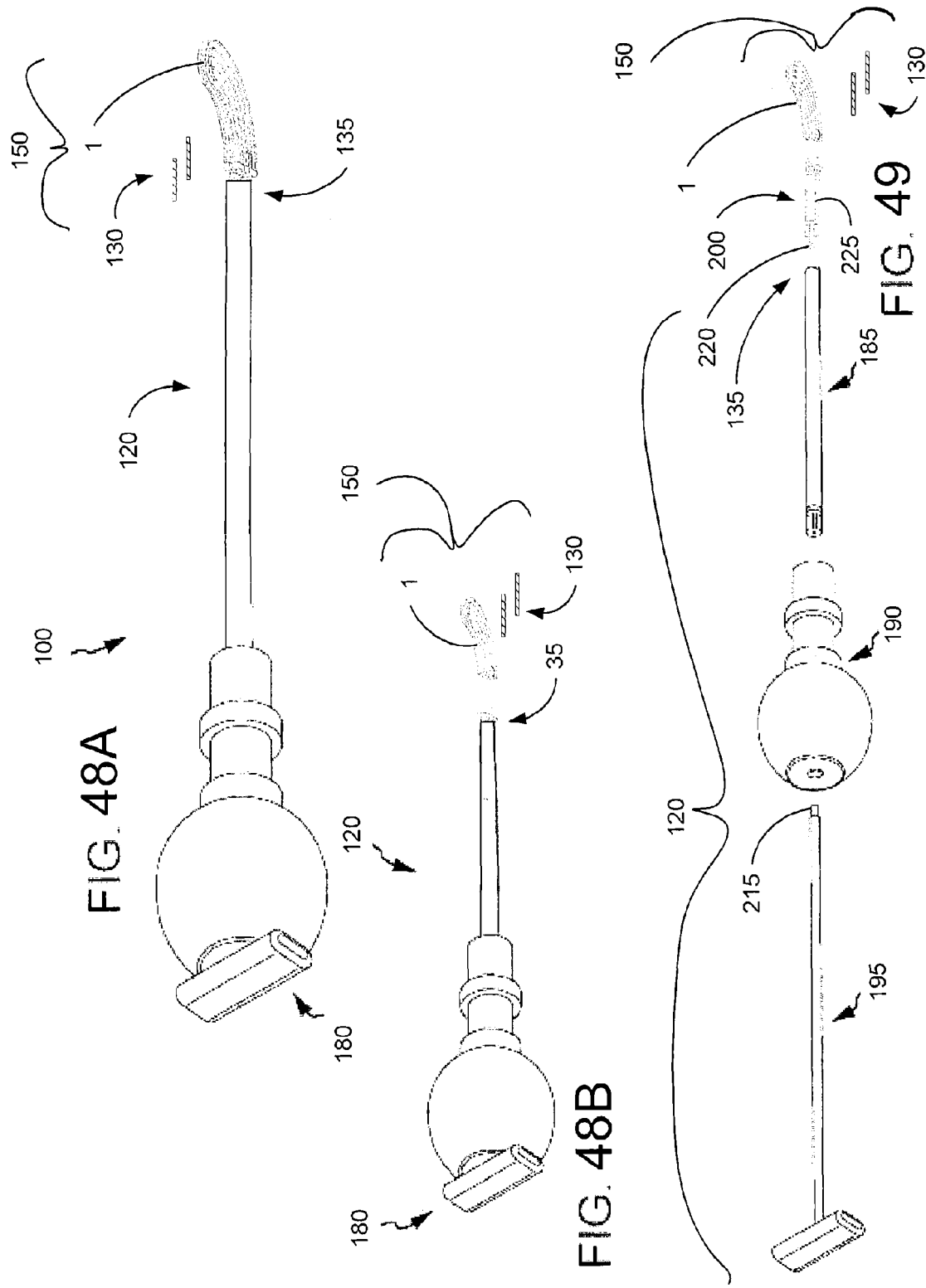

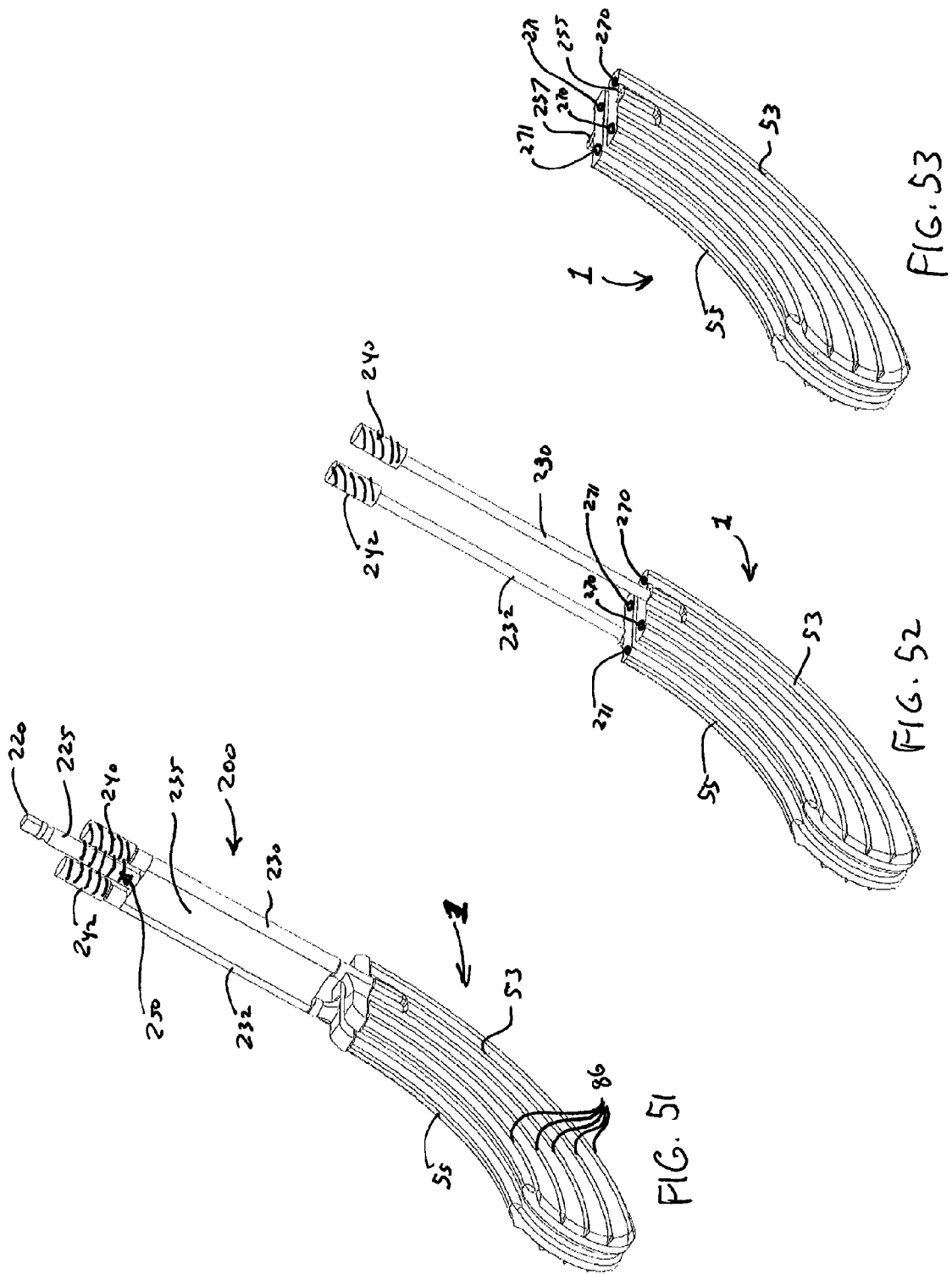

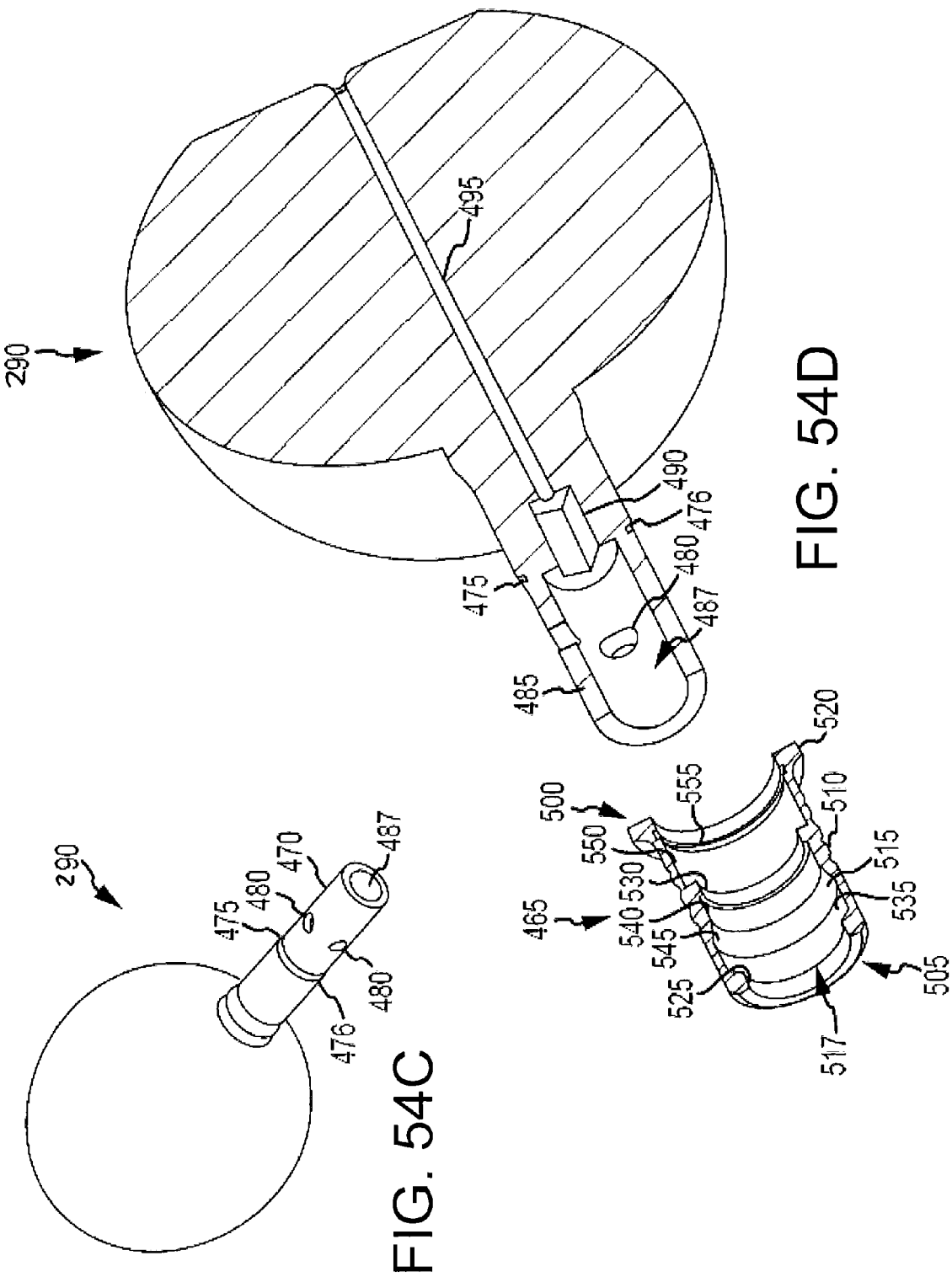

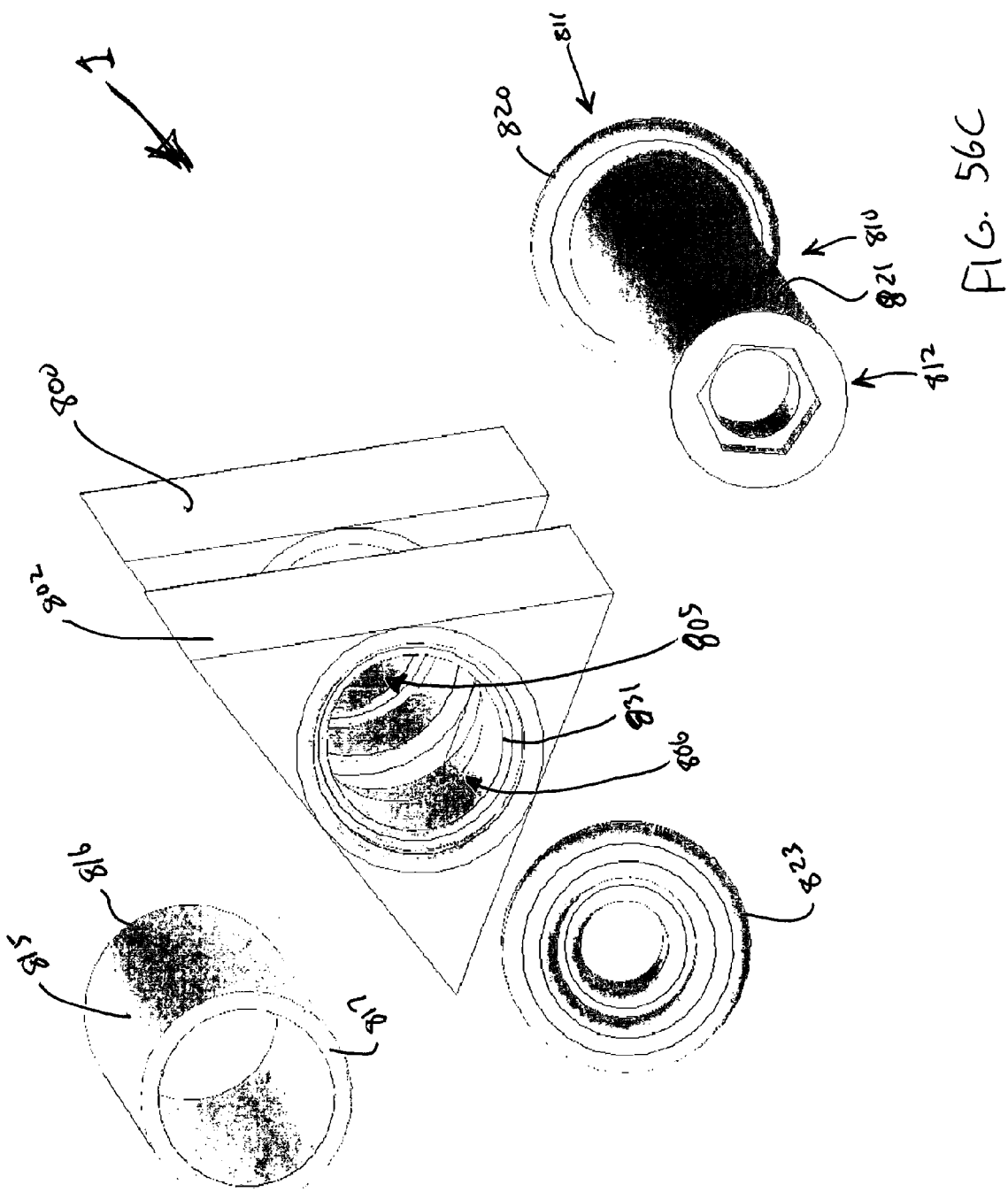

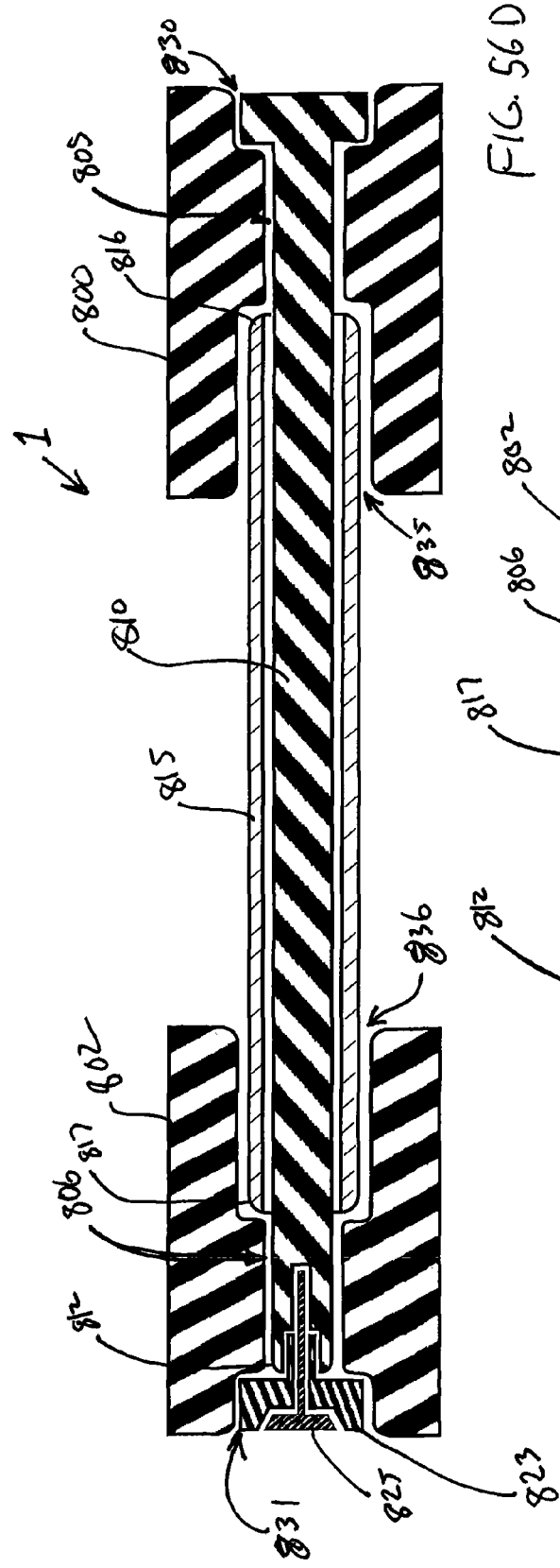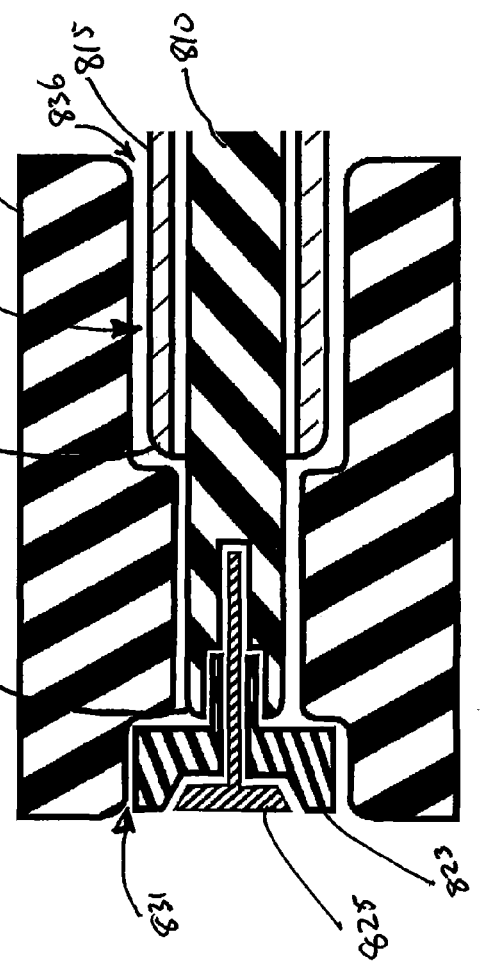

SACROILIAC JOINT IMPLANT SYSTEM

CROSS REFERENCE TO RELATED APPLICATIONS

This Patent Cooperation Treaty (PCT) patent application claims priority to and the benefit of U.S. Provisional Patent Application 61/520,956, which is entitled "Sacroiliac Joint Implant System" and was filed Jun. 17, 2011.

This PCT application is also a continuation-in-part (CIP) application of U.S. patent application Ser. No. 13/475,695 ("the '695 application"), which was filed May 18, 2012. The '695 application is a continuation-in-part (CIP) application of U.S. patent application Ser. No. 12/998,712 ("the '712 application"), which was filed May 23, 2011. The '712 application is the National Stage of International Patent Cooperation Treaty Patent Application PCT/US2011/000070 ("the '070 application"), which was filed Jan. 13, 2011. The '070 application claims the benefit of U.S. Provisional Patent Application 61/335,947, which was filed Jan. 13, 2010.

The present application is also a continuation-in-part (CIP) application of U.S. patent application Ser. No. 13/236,411, which is entitled "Systems for and Methods of Fusing a Sacroiliac Joint" and was filed Sep. 19, 2011.

All of the aforementioned applications are hereby incorporated by reference in their entireties into the present application.

FIELD OF THE INVENTION

A sacroiliac joint implant system that provides a sacroiliac joint implant and methods of placement of such implants in relation to a sacroiliac joint to facilitate stability while providing an amount of motion of the sacroiliac joint.

BACKGROUND

The sacroiliac joint is the joint between the sacrum and the ilium of the pelvis, which are joined by ligaments. In humans, the sacrum supports the spine and is supported in turn by an ilium on each side. The sacroiliac joint is a synovial joint with articular cartilage and irregular elevations and depressions that produce interlocking of the two bones.

Pain associated with the sacroiliac joint can be caused by traumatic fracture dislocation of the pelvis, degenerative arthritis, sacroiliitis, an inflammation or degenerative condition of the sacroiliac joint, osteitis condensans ilii, or other degenerative conditions of the sacroiliac joint. Currently, sacroiliac joint fusion is most commonly advocated as a surgical treatment for these conditions. Fusion of the sacroiliac joint can be accomplished by several different conventional methods. However, while each of these methods have been utilized for fixation and fusion of the sacroiliac joint over the past several decades, the methods to remove the painful degenerative aspects and to provide stability of the joint while allowing a degree of motion remains unresolved.

The sacroiliac joints are multi-planar, simultaneously rotating and translating along three axis of motion and can have six degrees of freedom secondary to the three angular and three linear motions occurring at each joint. Generally, rotation can range between about 0 to about 8 degrees. Generally, translation can range between about 0 and about 8 millimeters ("mm").

The inventive sacroiliac joint implant system described herein provides apparatuses and methods of placement of the apparatuses in relation to the sacroiliac joint which facilitate stability while allowing an amount of motion of the sacroiliac joint.

SUMMARY OF THE INVENTION

Accordingly, a broad object of the invention can be to provide an inventive implant to facilitate stabilization while allowing an amount of motion of a sacroiliac joint. Embodiments of the sacroiliac joint implant can provide an elongate body, which can further include at least one fixation member, or a pair of fixation members which extend a distance outward from the longitudinal axis of the implant body adapted for non-transverse placement between the articular surfaces of the sacroiliac joint, and as to certain embodiments can further provide a third fixation member and additionally a fourth fixation member each adapted to extend a distance outward from the elongate body into the bone of the sacrum or the ilium.

Another broad object of the invention can be to provide an inventive method to facilitate stabilization of the sacroiliac joint while allowing an amount of motion utilizing particular embodiments of the inventive sacroiliac implant. Particular embodiments of the inventive method can include the steps of performing a minimally invasive posterior surgery that allows access to the posterior aspect of the sacroiliac joint. A sufficient portion of the articular cartilage or tissue between the articular surfaces of the sacroiliac joint can be removed to allow placement of particular embodiments of the inventive sacroiliac implant between surfaces of the sacroiliac joint. As to particular embodiments, a portion of the subcondral bone of the sacroiliac joint can be removed to provide an implant receiving space in the plane of the sacroiliac joint configured to allow interference fitting of the elongate member, or the elongate member with at least a first radial member between the opposed surfaces of the implant receiving space. The inventive method can further include the step of providing the implant receiving space with one or more radial member receiving channels cut into the bone (including one or more of the subchondral, cortical, or cancellous) and thereby locating one or more radial members in the bone of the sacrum or the bone of the ilium.

Another broad object of the invention can be to provide a surface capable of osseointegration having a configuration which allows the bone of the sacrum or ilium to grow into the implant to facilitate fixation of the implant to the sacrum or the ilium.

Another broad object of the invention can be to provide particular embodiments of the inventive sacroiliac implant with an amount of curvature along the length of the implant which allows placement of embodiments of the sacroiliac implant which have an increased surface area which remain within or substantially within the articular portion of the sacroiliac joint.

Another broad object of the invention can be to provide particular embodiments of the inventive sacroiliac implant configured to allow placement of embodiments of the implant which have an increased surface area which remain within or substantially within the sacral fossa and iliac tuberosity portion of the sacroiliac joint.

Another broad object of the invention can be to provide particular embodiments of the inventive sacroiliac implant with a compressible element or elements which can receive, control or dissipate truncal loads.

Disclosed herein is a sacroiliac joint implant system for implantation in a sacroiliac joint space defined between an ilium and a sacrum. In one embodiment, the system includes an iliac member and a sacrum member. The iliac member includes an interface surface and a fixation surface generally opposite the interface surface. The fixation surface is configured to engage the ilium when the iliac member is implanted in the sacroiliac joint space. The sacrum member includes an interface surface and a fixation surface generally opposite the interface surface. The fixation surface is configured to engage the sacrum when the sacrum member is implanted in the sacroiliac joint space. When the iliac member and sacrum member are both implanted in the sacroiliac joint space such that the fixation surface of the ilium member engages the ilium, the fixation surface of the sacrum member engages the sacrum, and the iliac member and the sacrum member are located in the sacroiliac joint space immediately adjacent each other in an opposed fashion, the interface surface of the iliac member and the interface surface of the sacrum member are each configured so as to contact each other.

The interface surface of the iliac member and interface surface of the sacrum member may be both substantially planar and result in a sliding mating contact. At least one of the interface surface of the iliac member or the interface surface of the sacrum member may include a surface material that has at least one of high abrasion resistance or low coefficient of friction. For example, the surface material may include at least one of a ceramic, a polymer, Polyether ether ketone (PEEK), Polytetrafluoroethylene (PTFE), High-density polyethylene (HDPE), or Ultra High-density polyethylene (UHDPE).

The iliac member may further include at least one magnet at the interface surface of the iliac member and the sacrum member may further include at least one magnet at the interface surface of the sacrum member. At least one of the magnet of the iliac member and the at least one magnet of the sacrum member are arranged so as to draw the respective interface surfaces together. Alternatively, at least one of the magnet of the iliac member and the at least one magnet of the may be arranged to repel the respective interface surfaces away from each other.

The interface surface of the iliac member may include a first feature and interface surface of the sacrum member may include a second feature that engages the first feature to partially limit sliding of the sliding mating contact. Alternatively, the interface surface of the iliac member may include a first feature and interface surface of the sacrum member may include a second feature that engages the first feature so as to substantially, but not completely, limit movement between the iliac member and the sacrum member.

The sacrum member may be formed of a polymeric material and the second feature may have rigidity greater than a body portion of the sacrum member. The first feature may include a protrusion and the second feature may include a recess in which the protrusion is received, or the second feature may include a protrusion and the first feature may include a recess in which the protrusion is received. The protrusion may include a cylindrical element and the recess a channel element. The protrusion may include a guide element generally in the form of an elongated ridge and the recess an elongated channel element. The protrusion may include a convex surface and the recess a concave feature. The protrusion may include a generally T-shaped cross section transverse to a length of the protrusion, and the recess a generally T-shaped cross section transverse to a length of the recess.

The iliac member may have a curved length, and the sacrum member may have a curved length. At least one of the protrusion or recess may extend along the curved length of the iliac member, and at least one of the protrusion or recess may extend along the curved length of the sacrum member.

At least one of the fixation surface of the iliac member or the fixation surface of the sacrum member may include an outwardly projecting fixation member. The fixation member may include at least one of a longitudinally extending rib or a longitudinally extending member having a T-shaped transverse cross section.

Disclosed herein is another sacroiliac joint implant system for implantation in a sacroiliac joint space defined between an ilium and a sacrum. In one embodiment, the system includes a body and a fixation member. The body includes a longitudinal length extending between opposed extreme ends, opposed faces extending between the opposed extreme ends, and opposed sides separating the opposed faces and extending between the opposed extreme ends. The opposed faces are substantially wider than the opposed sides. The fixation member projects outwardly from each of the opposed faces and extends along the longitudinal length of the body.

The body may include a generally oval transverse cross section. At least one of the fixation members may have a transverse T-shaped cross section.

At least one of the fixation members may be separately formed from the body and mechanically coupled to the body via at least one of a grooved arrangement, an adhesive, or a weld. The separately formed fixation member may include a transverse I-shaped cross section and the grooved arrangement a slot defined in the body and including a transverse T-shaped cross section. One end of the transverse I-shaped cross section may be matingly received in the transverse T-shaped cross section.

The body may include a guide pin orifice extending longitudinally through the body to daylight at each of the opposed ends. The body and fixation members may curve along their respective longitudinal lengths. The body as defined by the opposed ends and opposed sides when viewed generally perpendicular to one of the opposed faces may have a generally rectangular shape. One of the opposed ends of the body may be tapered and the other of the opposed ends of the body may be configured to be coupled to a delivery device.

Each of the fixation members may include opposed ends, and one of the opposed ends may be tapered as compared to the other of the opposed ends. The implant may be segmented along its length into multiple distinct sections that can be assembled together in the sacroiliac joint space to form the implant.

Disclosed herein is yet another sacroiliac joint implant system for implantation in a sacroiliac joint space defined between an ilium and a sacrum. In one embodiment, the system includes an iliac member, a sacrum member, and a core element. The iliac member includes an interface surface and a fixation surface generally opposite the interface surface. The fixation surface is configured to engage the ilium when the iliac member is implanted in the sacroiliac joint space. The interface surface includes a recess. The sacrum member includes an interface surface and a fixation surface generally opposite the interface surface. The fixation surface is configured to engage the sacrum when the sacrum member is implanted in the sacroiliac joint space. The interface surface includes a recess. The core element includes a first interface surface and a second interface surface opposite the first interface surface. The first interface surface includes a feature extending outwardly from the first interface surface. The second interface surface includes a feature extending outwardly from the second interface surface. When the system is assembled, the core element is sandwiched between the iliac member and sacrum member and the feature of the first interface surface of the core element is received in the recess of the interface surface of the iliac member and the feature of the second interface surface of the core element is received in the recess of the interface surface of the sacrum member.

When the system is assembled, the interface surface of the iliac member may be maintained in a spaced-apart relationship with the interface surface of the sacrum member. The interface surface of the iliac member may be generally a surface negative of the first interface surface of the core element such that a surface contour of the interface surface of the iliac member generally matingly engages and generally matches a surface contour of the first interface surface of the core element. The interface surface of the sacrum member may be generally a surface negative of the second interface surface of the core element such that a surface contour of the interface surface of the sacrum member generally matingly engages and generally matches a surface contour of the second interface surface of the core element.

The feature of the first interface surface may include a raised ridge, and the recess of the interface surface of the iliac member includes a channel that has a complementary shape to a shape of the feature of the first interface surface. The iliac member, sacrum member and core element may curve along their respective lengths. Each of the fixation surfaces may include a fixation member projecting outwardly and extending along the longitudinal length of the respective sacrum member or iliac member. The fixation member may include a ridge.

Disclosed herein is a method of treating a sacroiliac joint via implantation of an implant into a space of the sacroiliac joint. In one embodiment, the method includes: providing an iliac member including an interface surface and a fixation surface generally opposite the interface surface; providing a sacrum member including an interface surface and a fixation surface generally opposite the interface surface; delivering the iliac member into the sacroiliac joint space such that the fixation surface of the iliac member engages the ilium and the interface surface of the iliac member faces in the direction of the sacrum; delivering the sacrum member into the sacroiliac joint space such that the fixation surface of the sacrum member engages the sacrum and the interface surface of the sacrum member faces in the direction of the ilium; and engaging the interface surface of the iliac member with the interface surface of the sacrum member such that substantially restricted movement of the iliac member relative to the sacrum member is possible when both the iliac member and sacrum member are implanted in the sacroiliac joint space and the interface surfaces are engaged with each other.

The method may further include sandwiching a core element between the interface surface of the iliac member and the interface surface of the sacrum member, such a sandwiched arrangement being a mechanism for engaging the interface surface of the iliac member with the interface surface of the sacrum member. The interface surface of the iliac member may be maintained in a spaced-apart arrangement from the interface surface of the sacrum member when the core element is sandwiched between the interface surfaces and the interface surfaces are engaged with each other. The sandwiched arrangement may be established before the iliac member and sacrum member are delivered into the sacroiliac joint space. The sandwiched arrangement may be established after the iliac member and sacrum member are delivered into the sacroiliac joint space.

In engaging the interface surface of the iliac member with the interface surface of the sacrum member, the interfaces surfaces may make direct physical contact and a feature of one of the interface surfaces may be received in a feature of the other of the interface surfaces. The interface surface of the iliac member and interface surface of the sacrum member may be both substantially planar and result in a sliding mating contact. The interface surface of the iliac member may include a first feature, and interface surface of the sacrum member may include a second feature that engages the first feature to partially limit sliding of the sliding mating contact. Alternatively, the interface surface of the iliac member may include a first feature and interface surface of the sacrum member may include a second feature that engages the first feature so as to substantially, but not completely, limit movement between the iliac member and the sacrum member.

The first feature may include a protrusion and the second feature a recess in which the protrusion is received, or the second feature may include a protrusion and the first feature a recess in which the protrusion is received. The protrusion may include a cylindrical element and the recess a channel element. The protrusion may include a guide element generally in the form of an elongated ridge and the recess an elongated channel element. The protrusion may include a convex surface and the recess a concave feature. The protrusion may include a generally T-shaped cross section transverse to a length of the protrusion, and the recess a generally T-shaped cross section transverse to a length of the recess. The iliac member may have a curved length, and the sacrum member a curved length. At least one of the protrusion or recess may extend along the curved length of the iliac member, and at least one of the protrusion or recess along the curved length of the sacrum member.

At least one of the fixation surface of the iliac member or the fixation surface of the sacrum member may include an outwardly projecting fixation member. The fixation member may include at least one of a longitudinally extending rib or a longitudinally extending member having a T-shaped transverse cross section.

The engagement of the interface surface of the iliac member with the interface surface of the sacrum member may be established before the iliac member and sacrum member are delivered into the sacroiliac joint space. Alternatively, the engagement of the interface surface of the iliac member with the interface surface of the sacrum member may be established after the iliac member and sacrum member are delivered into the sacroiliac joint space. The limited movement between the iliac member and the sacrum member may allow for at least one of a rocking or sliding between the iliac member and the sacrum member.

Disclosed herein is a method of treating a sacroiliac joint via implantation of an implant into a space of the sacroiliac joint. In one embodiment, the method includes: positioning a generally empty balloon in the sacroiliac joint space; filling the positioned balloon with a curable biomaterial such that the balloon expands to fill at least a portion of the sacroiliac joint space to substantially restore a desired anatomy of the sacroiliac joint space; and allowing the biomaterial to cure. The cured biomaterial may exhibit elastic properties when submitted to forces present in the sacroiliac joint space.

The balloon may be constructed in two layers. For example, an outer of the two layers may be configured to facilitate tissue ingrowth into the outer of the two layers.

The outer layer of the balloon may include a sacrum face, an ilium face and intermediate regions extending between the sacrum face and the ilium face. The sacrum face and ilium face may be configured to facilitate tissue ingrowth and the intermediate regions configured to inhibit tissue ingrowth.

Disclosed herein is yet another sacroiliac joint implant system for implantation in a sacroiliac joint space defined between an ilium and a sacrum. In one embodiment, the system includes an iliac member, a sacrum member, and a delivery tool. The iliac member includes an interface surface, a fixation surface generally opposite the interface surface, and a threaded bore near a proximal end of the iliac member. The fixation is configured to engage the ilium when the iliac member is implanted in the sacroiliac joint space. The sacrum member includes an interface surface, a fixation surface generally opposite the interface surface, and a threaded bore near a proximal end of the sacrum member. The fixation surface is configured to engage the sacrum when the sacrum member is implanted in the sacroiliac joint space. The interface surface of the sacrum member is configured to engage the interface surface of the iliac member. The delivery tool includes an implant retainer having a drive shaft, a first shaft distally terminating in a first threaded distal end, and a second shaft distally terminating in a second threaded distal end. Rotation of the drive shaft causes the first and second shafts to rotate oppositely from each other. Rotation of the drive shaft in a first direction causes the first and second threaded distal ends to respectively threadably engage with the threaded bore of the sacrum member and threaded bore of the ilium member.

Naturally, further objects of the invention are disclosed throughout other areas of the specification, drawings, photographs, and claims.

BRIEF DESCRIPTION OF THE DRAWINGS

FIG. 2 is a first end view of the particular embodiment of the sacroiliac joint implant shown in FIG. 1.

FIG. 3 is a side view of the particular embodiment of the sacroiliac joint implant shown in FIG. 1.

FIG. 4 is a second end view of the particular embodiment of the sacroiliac joint implant shown in FIG. 1.

FIG. 5 is a first end view of a particular embodiment of the sacroiliac joint implant.

FIG. 6 is a side view of the particular embodiment of the sacroiliac joint implant shown in FIG. 5.

FIG. 7 is a second end view of the particular embodiment of the sacroiliac joint implant shown in FIG. 5.

FIG. 18 is a first end view of the particular embodiment of a sacroiliac joint implant shown in FIG. 17 having the sacral member matably engaged to the iliac member.

FIG. 19 is a second end view of the particular embodiment of a sacroiliac joint implant shown in FIG. 17 having the sacral member matably engaged to the iliac member.

FIG. 20 is a first side view of the sacral member showing a sacral member interface surface.

FIG. 21 is a first side view of the iliac member showing an iliac member interface surface.

FIG. 22 is a second side view of the sacral member showing sacral member fixation surface.

FIG. 23 is a second side view of the iliac member showing iliac member fixation surface.

FIG. 36 is an exploded perspective view of a particular embodiment of a sacroiliac joint implant having a sacral member which matably engages an iliac member.

FIG. 37 is a perspective view of the particular embodiment of a sacroiliac joint implant shown in FIG. 36 having the sacral member matably engaged to the iliac member.

FIG. 38 is a first end view of the particular embodiment of a sacroiliac joint implant shown in FIG. 36 having the sacral member matably engaged to the iliac member.

FIG. 39 is a side view of the particular embodiment of a sacroiliac joint implant shown in FIG. 36 having the sacral member matably engaged to the iliac member.

FIG. 40 is a second end view of the particular embodiment of a sacroiliac joint implant shown in FIG. 36 having the sacral member matably engaged to the iliac member.

FIG. 41 is a cross section 41-41 of the particular embodiment of a sacroiliac joint shown in FIG. 37 having the sacral member engaged to the iliac member having a core element disposed between.

FIG. 48A is an isometric view of an embodiment of a system for treating a sacroiliac joint.

FIG. 48B is the same view as FIG. 48A, except the delivery tool and implant assembly are decoupled from each other.

FIG. 49 is the same view as FIG. 48A, except the system is exploded to better illustrate its components.

FIG. 51 is an isometric view of the implant retainer coupled to a proximal end of the implant.

FIG. 52 is the same view as FIG. 51, except the frame and drive shaft of the implant retainer are hidden for clarity purposes.

FIG. 53 is the same view as FIG. 51, except the implant retainer is hidden for clarity purposes.

FIG. 54C is an isometric view of the handle.

FIG. 54D is an exploded isometric view of the retaining collar and handle shown in longitudinal cross section.

FIGS. 56B and 56C are exploded isometric views of the implant of FIG. 56A.

FIG. 56D is a longitudinal cross sectional elevation of the implant as taken along section line 56D-56D in FIG. 56A.

FIG. 56E is an enlarged view of one end of the cross section of FIG. 56D.

DETAILED DESCRIPTION OF THE PREFERRED EMBODIMENTS

Figure 1:
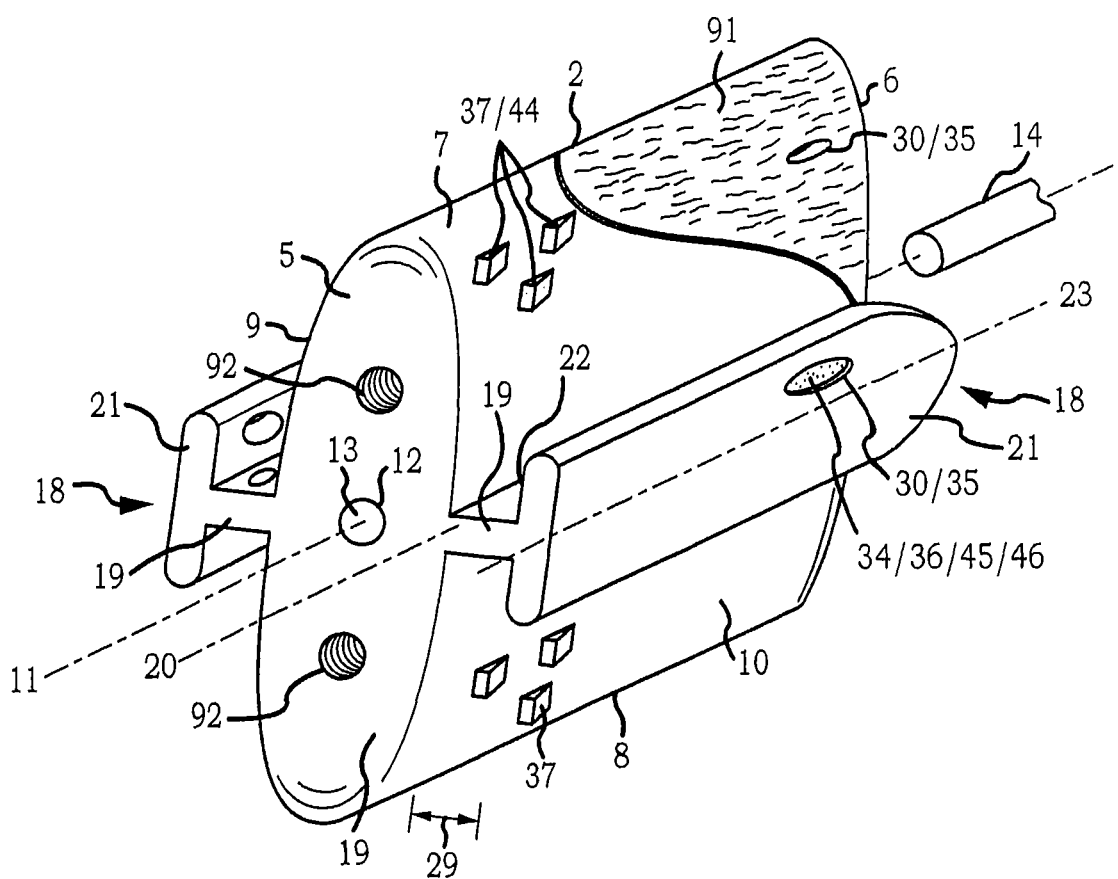
FIG. 1 is a perspective view of a particular embodiment of the sacroiliac joint implant.

Generally, a sacroiliac joint implant system that provides embodiments of a sacroiliac joint implant and methods of placing the sacroiliac joint implant in relation to a sacroiliac joint to facilitate stabilization and allow an amount of motion of the sacroiliac joint.

Now referring primarily to FIGS. 1-16, a non-limiting embodiment of an inventive sacroiliac joint implant (1) is shown which in part can include a first implant body (2). The first implant body (2) can have a generally rectangular configuration in plan view (see as a non-limiting example FIG. 3) and can have a generally oval or ellipsoidal configuration in end view (see as a non-limiting example FIGS. 42A-C). The first implant body (2) can have a configuration of sufficient dimensional relations to allow non-traverse placement between the surfaces of an ilium (3) and a sacrum (4) (see as non-limiting examples FIGS. 42A through 42C) and which avoid deformation under the normal forces of surgical placement and stabilization of the ilium (3) in relation to the sacrum (4). A particular non-limiting embodiment of the first implant body (2) shown in FIGS. 1-4 can, depending on the application, have a length disposed between a first implant end (5) and a second implant end (6) in the range of about 3 cm and about 6 cm and a width disposed between a first implant side (7) and a second implant side (8) in the range of about 2 cm and about 4 cm and a height disposed between a first implant face (9) and a second implant face (10) in the middle of the first implant body (2) of about 0.75 cm and about 1.5 cm. Additionally, while the embodiment of the implant body (2) of the sacroiliac joint implant (1) shown in FIGS. 1-4 can be generally oval or ellipsoidal in end view or cross section; the invention is not so limited, and the first implant body (2) can have any of a numerous and varied configurations in cross section across the longitudinal axis (11) consistent with the method herein after described such as oval, triangular, rectangular, square, diamond, or the like.

Now referring primarily to FIGS. 11-16 and 45, particular embodiments of the first implant body (2) can further provide an amount of curvature (15) between the first implant end (5) and the second implant end (6). The amount of curvature (15) sufficient to allow placement of the first implant body (2) non-transversely between the articular surfaces (16) (see for example FIG. 45) of the sacrum (4) and the ilium (3), as further described below.

Embodiments of the first implant body (2) can further include an axial bore (12) that bounds an axial pathway (13) which communicates between a first implant end (5) and a second implant end (6). The axial bore (12) can allow sliding engagement of a guide pin (14) (or other guide member) within the axial pathway (13) to facilitate insertion and placement of the sacroiliac joint implant (1) between the surfaces of the ilium (3) and the sacrum (4), as further described below.

Figure 16:
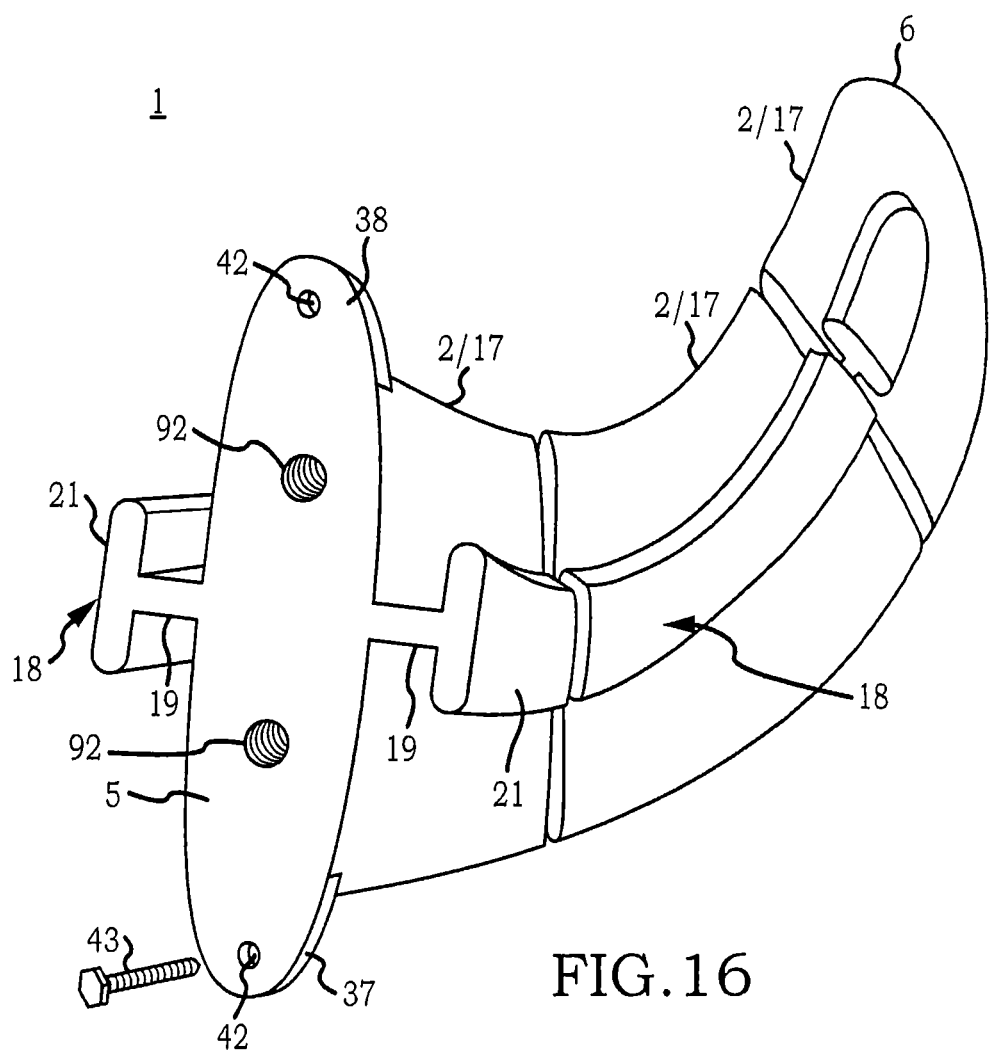
FIG. 16 is a perspective view of a particular embodiment of a sacroiliac joint implants disposed in a plurality of segments.
Figure 17:
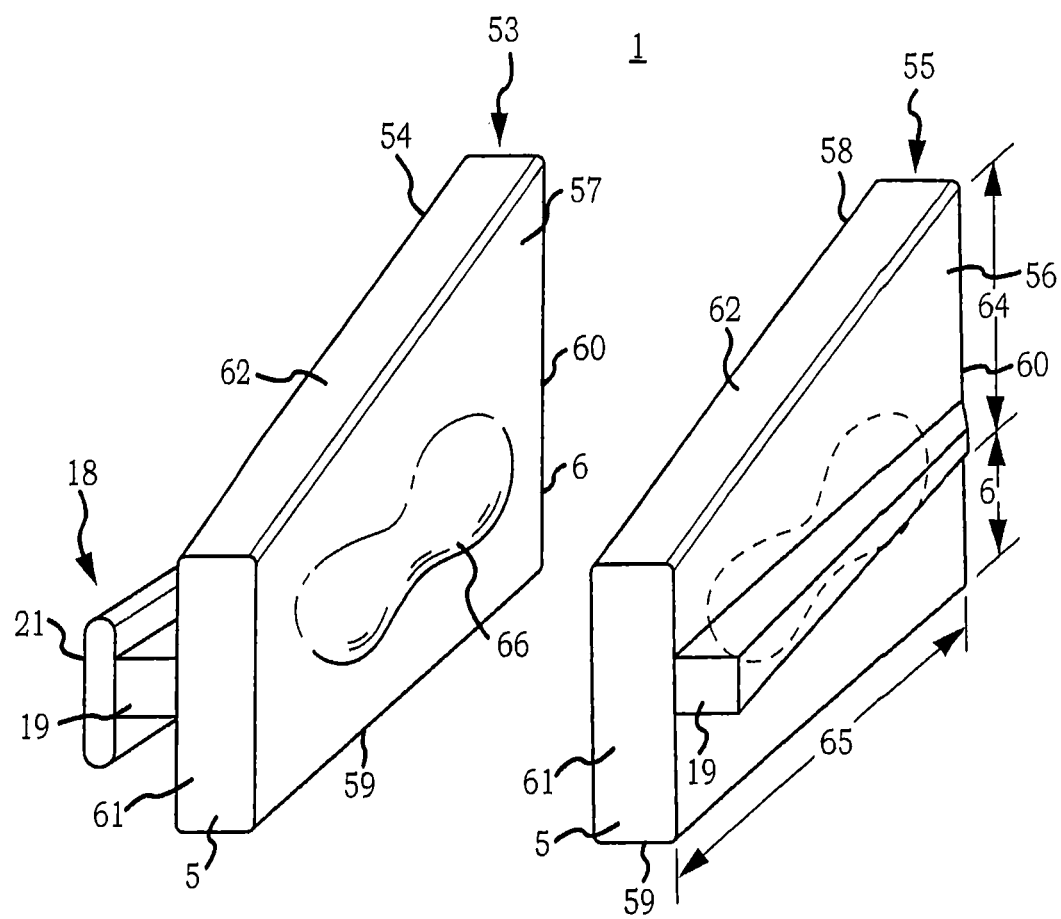
FIG. 17 is a perspective view of a particular embodiment of a sacroiliac joint implant having a sacral member which matably engages an iliac member.
Figure 24:
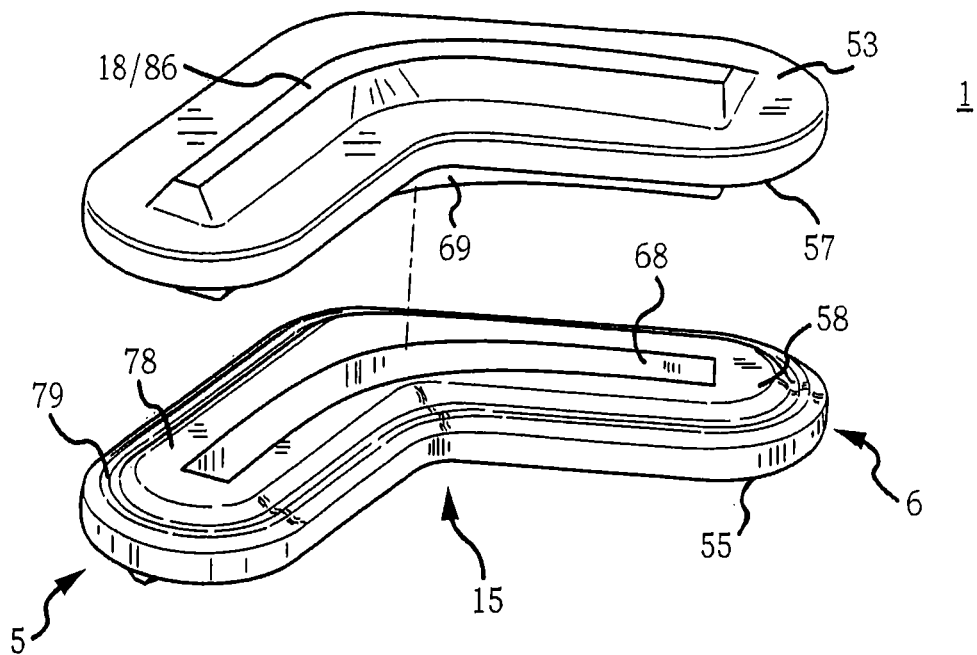
FIG. 24 is a perspective view of a particular embodiment of a sacroiliac joint implant having a sacral member which matably engages an iliac member.
Figure 25:
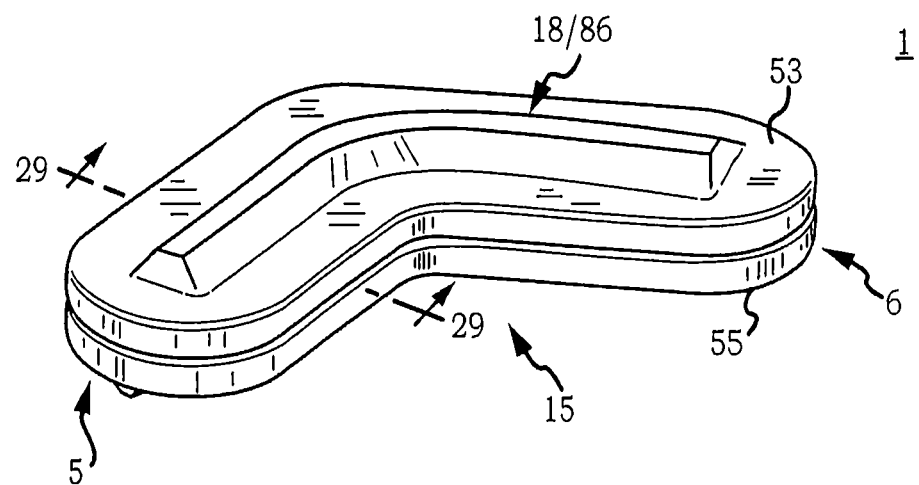
FIG. 25 is a perspective view of the particular embodiment of a sacroiliac joint implant shown in FIG. 24 having the sacral member matably engaged to the iliac member.
Figure 26:
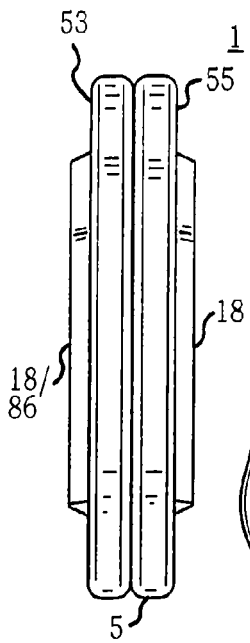
FIG. 26 is a first end view of the particular embodiment of a sacroiliac joint implant shown in FIG. 24 having the sacral member matably engaged to the iliac member.
Figure 27:
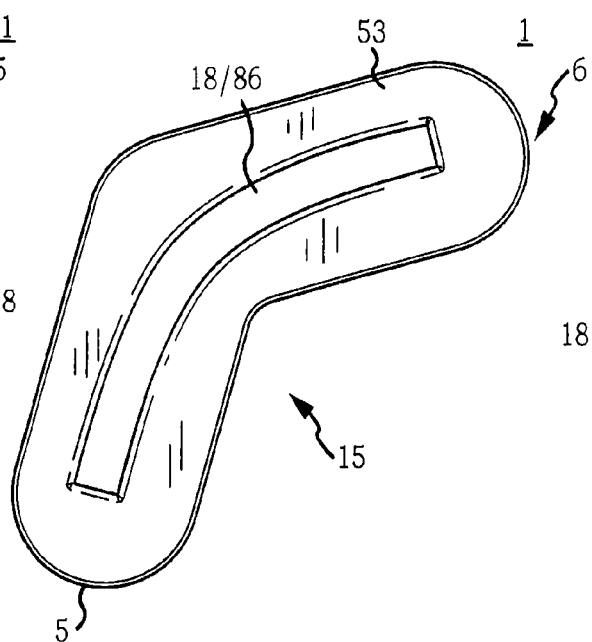
FIG. 27 is a side view of the particular embodiment of a sacroiliac joint implant shown in FIG. 24 having the sacral member matably engaged to the iliac member.
Figure 28:
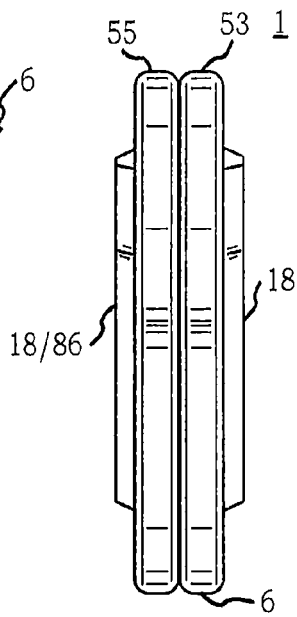
FIG. 28 is a second end view of the particular embodiment of a sacroiliac joint implant shown in FIG. 24 having the sacral member matably engaged to the iliac member.
Figure 29:
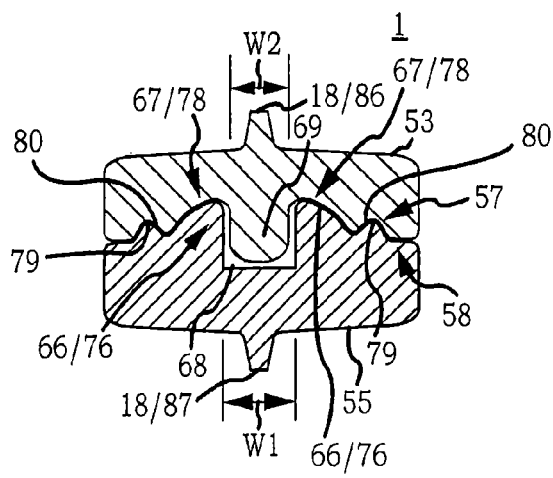
FIG. 29 is a cross section 29-29 shown in FIG. 25 of the particular embodiment of a sacroiliac joint implant shown in FIG. 24 having the sacral member matably engaged to the iliac member.
Figure 30:
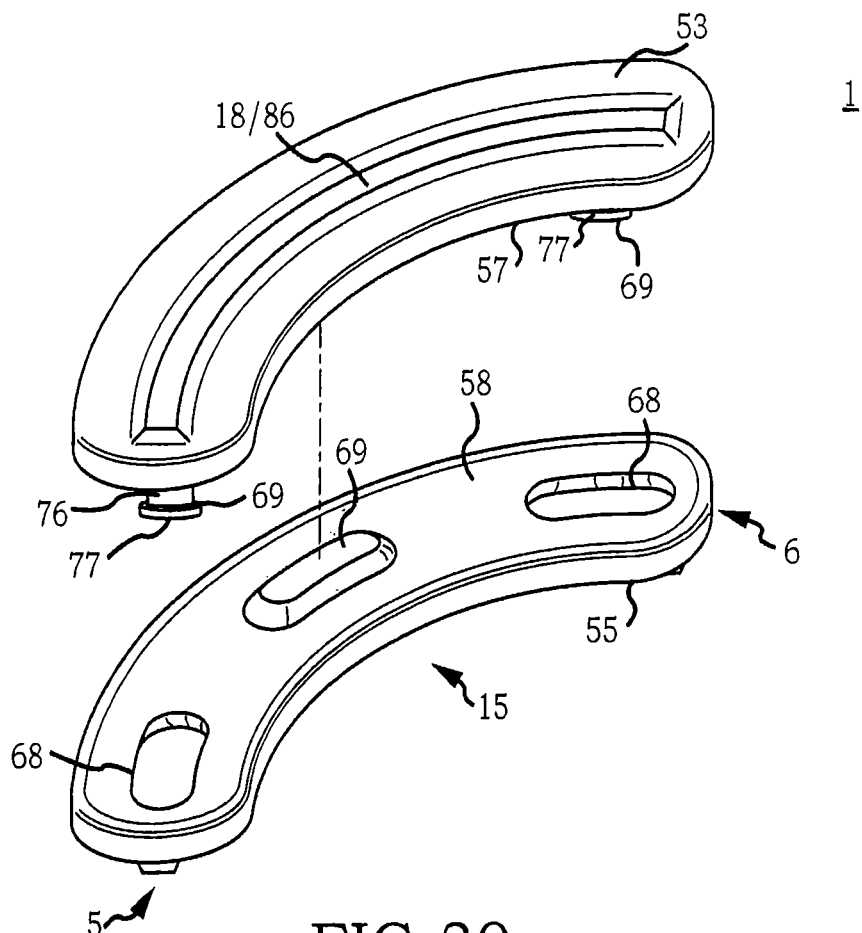
FIG. 30 is a perspective view of a particular embodiment of a sacroiliac joint implant having a sacral member which matably engages an iliac member.
Figure 31:
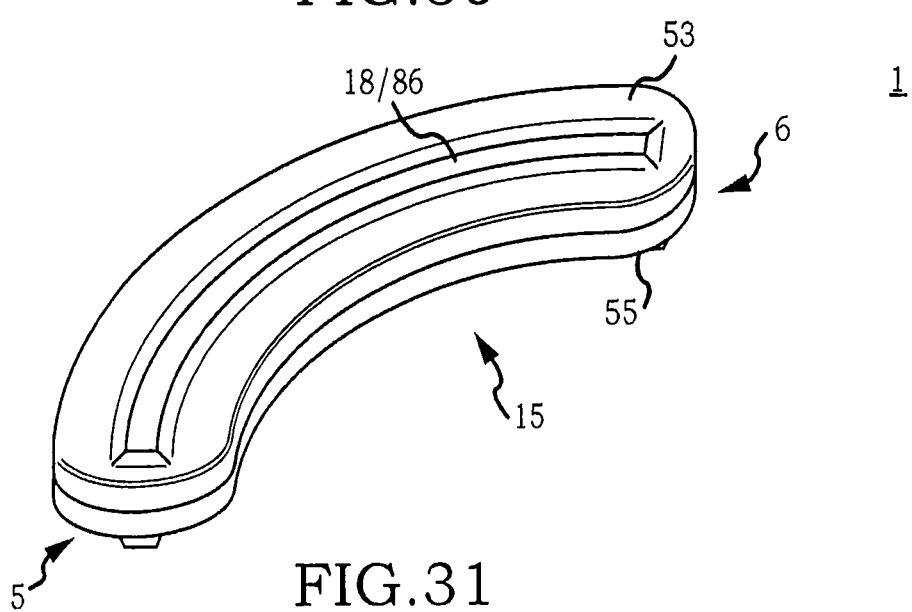
FIG. 31 is a perspective view of the particular embodiment of a sacroiliac joint implant shown in FIG. 30 having the sacral member matably engaged to the iliac member.
Figures 32, 33, 34:
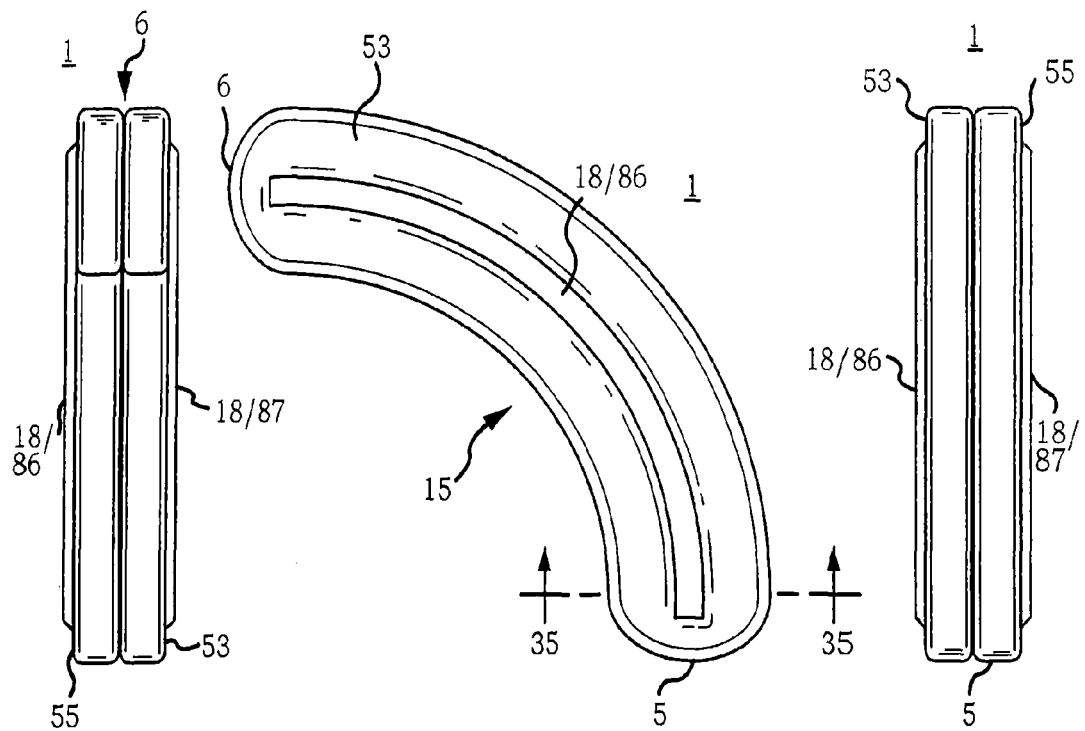
FIG. 32 is a second end view of the particular embodiment of a sacroiliac joint implant shown in FIG. 30 having the sacral member matably engaged to the iliac member.
FIG. 33 is a side view of the particular embodiment of a sacroiliac joint implant shown in FIG. 30 having the sacral member matably engaged to the iliac member.
FIG. 34 is a first end view of the particular embodiment of a sacroiliac joint implant shown in FIG. 30 having the sacral member matably engaged to the iliac member.
Figure 35:
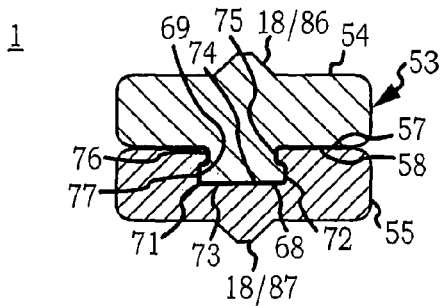
FIG. 35 is a cross section 35-35 shown in FIG. 33 of the particular embodiment of a sacroiliac joint implant shown in FIG. 30 having the sacral member matably engaged to the iliac member.

Again referring primarily to FIG. 16, particular embodiments of the first implant body (1) can be provided as two or more implant body segments (17), each of the implant body segments implanted separately between the sacrum (4) and the ilium (3) to collectively stabilize the sacrum (4) in relation to the ilium (3).

Again referring primarily to FIGS. 1-4 and 11-16, embodiments of the sacroiliac joint implant (1) can further include one or more fixation members (18) coupled to the external surface of the implant body (2). As to certain embodiments of the first implant body (2), the one or more fixation members (18) can include a corresponding one or more projection elements (19) which can extend along a part of or substantially along the entire length of the implant body (2) substantially aligned with the longitudinal axis (11) (as shown for example in FIGS. 1 through 7) or generally along the implant body mid-line (20) corresponding to the amount of curvature (15) of the implant body (2), (as shown in FIGS. 11 through 16). As to other embodiments of the implant body (2), the projection elements (19) can extend outward from the external surface of implant body (2) and terminate in an enlarged terminal member (21). The terminal element (21), as shown in FIGS. 1 through 4, can be configured as a generally rectangular volume to which the projection element (19) couples to a first side (22) substantially along the terminal element longitudinal midline (23); however, the invention is not so limited and the terminal element (21) can be configured in cross section generally perpendicular to the terminal element midline (23) as a circle, rectangle, dovetail, oval, or the like.

Again referring to FIGS. 1-4 and FIGS. 42A through 42 C, a particular embodiment of the first implant body (2) can have a pair of fixation members (18) which can function to correspondingly engage the bone of the sacrum (4) and the ilium (3), as further described below. Understandably, particular embodiments of the first body (2) can have one fixation member (18) which can correspondingly engage only the bone of the sacrum (4) or the ilium (3). Certain embodiments of the first implant body (2), do not have any fixation members (18) and can be non-transversely placed between surfaces of the ilium (3) and sacrum (4).

Now referring primarily to FIGS. 5 through 7, certain embodiments of the sacroiliac joint implant (1) provide a second implant body (24) which can be but is not necessarily similar in configuration to the first implant body (2). The second implant body (24) can provide a fixation member receiving channel (25) disposed in the external surface thereof, typically either in the first implant face (9) or in the second implant face (10). The fixation member receiving channel (25) can be configured to slidably matingly engage a fixation member (18) of the first implant body (2). In accordance with the example of FIGS. 1 through 7, the fixation member (18) extending from the external surface of the first implant body (2) has a projection element (19) and a terminal member (20) configured in a T shape. The fixation member receiving channel (25) of the second implant body (24) can correspondingly provide a T shape channel which communicates with the external surface of the second implant body (24) to provide a slot (28) in which the projection element (19) of the fixation member (18) of the first implant body passes through in sliding engagement with the second implant body (24) to dispose the first or second face (9)(10) of the first implant body (2) and the first or second face (9)(10) of the second implant body (24) in opposed adjacent relation. A greater or lesser distance between the faces (9)(10) of the first and second implant bodies (2)(24) can be established by a correspondingly varying the projection member height (29). The fixation member receiving channel (25) can be open at a first channel end (26) and closed at a second channel end (27) such that the fixation member (18) advances a limited distance within fixation member receiving channel (25).

The amount of movement whether in a first, second, or third axis between the first implant body (2) and the second implant body (24) can be adjusted by alteration of the configuration of the fixation member (18) and the fixation member receiving channel (25). Accordingly, upon placement of the coupled first implant body (2) and the second implant body (24) between the sacrum (4) and ilium (3), the first implant body (2) and the second implant body (24) as constrained by placement between the sacrum (4) and the ilium (3) can have an amount of movement in relation to each other. Alternatively, movement can be permitted by configuring the first implant body (2) and the second implant body (24) by selecting a material which exhibits elastic properties under the normal forces present at the sacroiliac joint. Furthermore, fixation member (18) may also be constructed of a similar material or alternatively a metal may be selected which can be more readily adapted for osseointegration with either the sacrum (4) or ilium (3).

Figure 8:
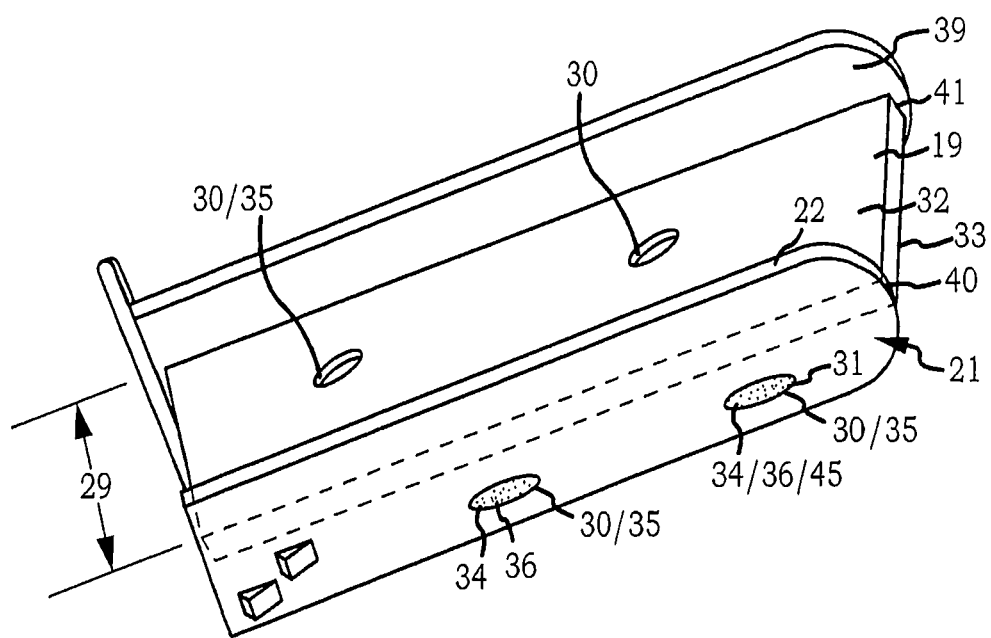
FIG. 8 is a perspective view of a fixation member removably insertable into the embodiment of the sacroiliac joint implant shown in FIG. 5.
Figure 9:
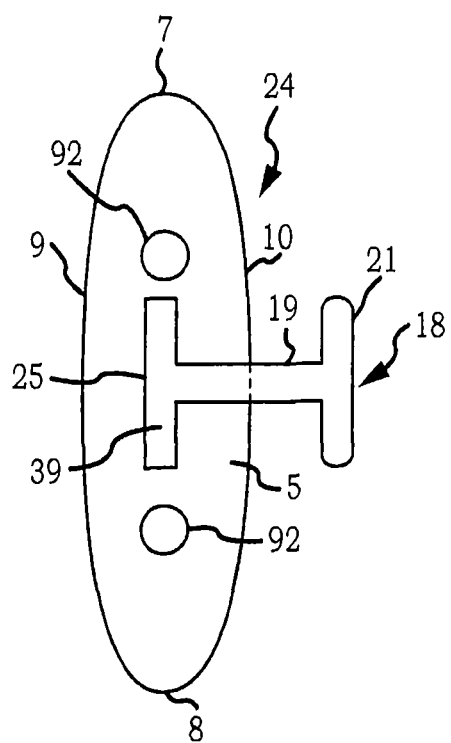
FIG. 9 is a first end view of the particular embodiment of the sacroiliac joint implant shown in FIGS. 5-7 coupled to the fixation member shown in FIG. 8.
Figure 10:
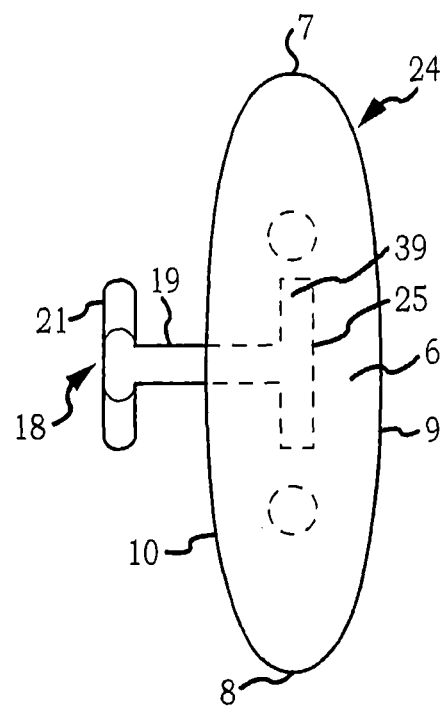
FIG. 10 is a second end view of the particular embodiment of the sacroiliac joint implant shown in FIGS. 5-7 coupled to the fixation member shown in FIG. 8.
Figure 11:
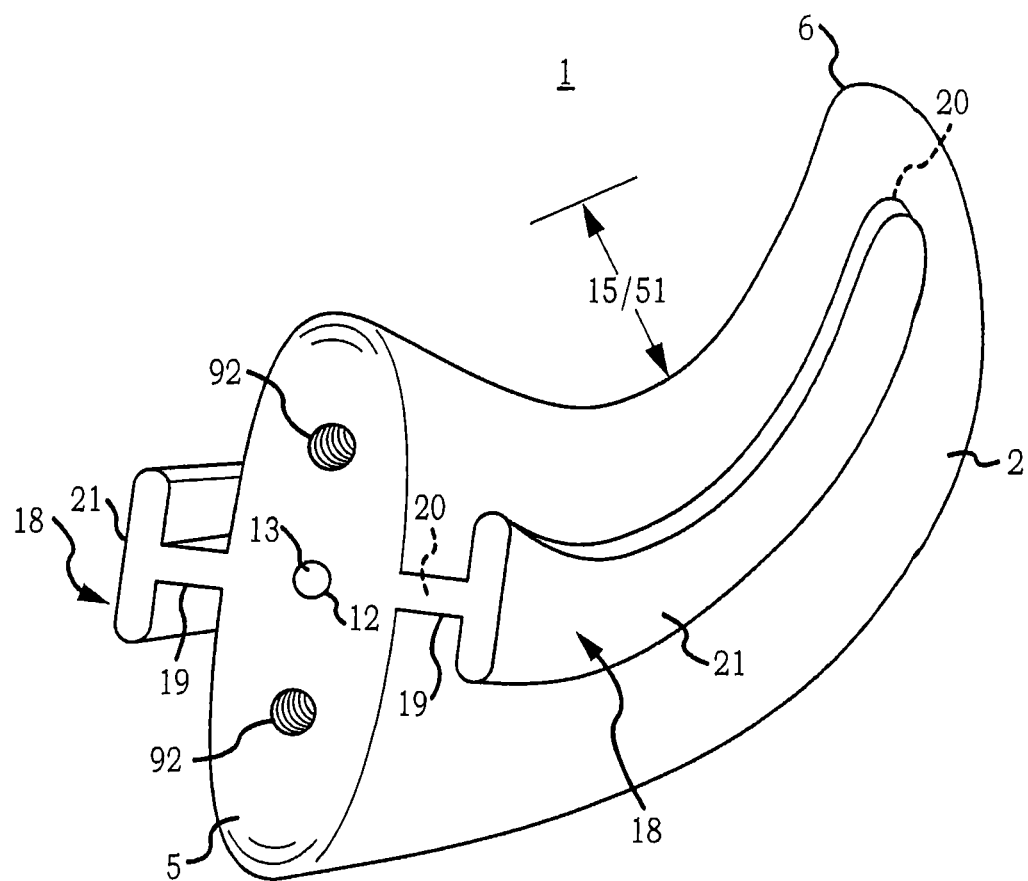
FIG. 11 is a perspective view of another particular embodiment of the sacroiliac joint implant.
Figure 12:
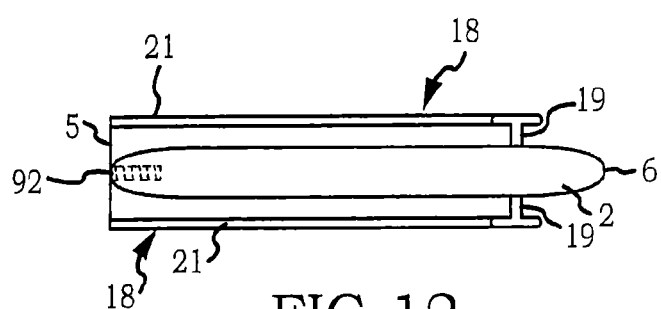
FIG. 12 is a top view of the particular embodiment of the sacroiliac joint implant shown in FIG. 11.
Figures 13, 14:
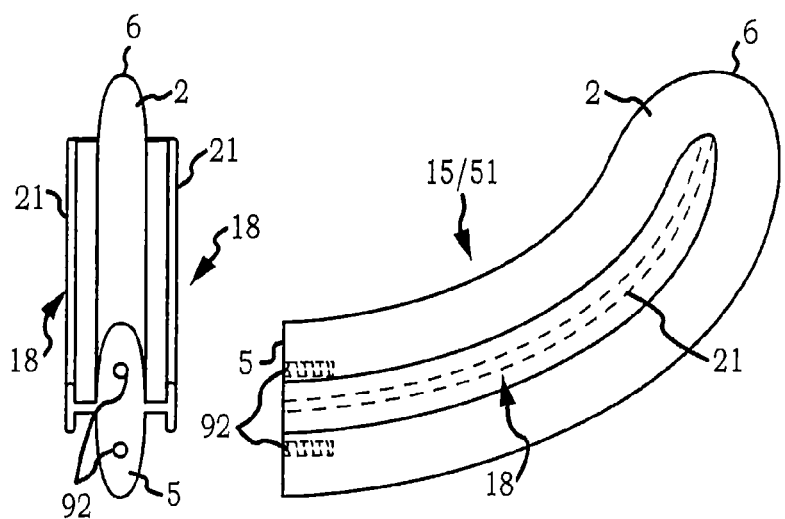
FIG. 13 is a first end view of the particular embodiment of the sacroiliac joint implant shown in FIG. 11.
FIG. 14 is a side view of the particular embodiment of the sacroiliac joint implant shown in FIG. 11.
Figure 15:
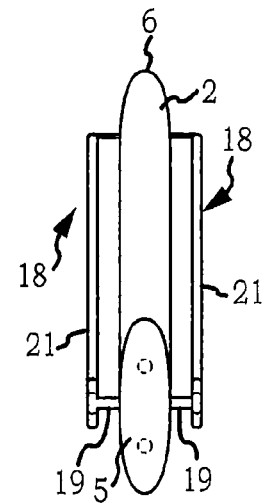
FIG. 15 is a second end view of the particular embodiment of the sacroiliac joint implant shown in FIG. 11.

Now referring primarily to FIGS. 8-10, particular embodiments of the second implant body (24) can further provide a fixation member (18) which can be inserted, whether removably, nonremovably, slidably, stepwise or forced inward against resisting elements, into the fixation member receiving channel (25). The fixation member (18) can provide the projection element (19) having the terminal element (21) coupled to a first edge (40) as above described and can further provide a channel insertion element (39) which couples to the second edge (41) of the projection element (19). The channel insertion element (39) can be configured to engage the fixation member receiving channel (25) as above described to provide a second implant body (24) having a fixation member (18) extending outward from the external surface of the second implant body (24) which can upon placement between the sacrum (4) and the ilium (3) correspondingly engage the bone of the sacrum (4) or the ilium (3). Alternately, the second implant body (24) having the fixation member (18) coupled can function as the first implant body (2) and the extending fixation element (18) can be coupled within the fixation member receiving channel (25) of a second implant body (24), thereby each of the first implant body (2) and the second implant body (24) can move in relation to one another.

As a non-limiting example, the first implant body (2) and the second implant body (24) and the fixation member (18) can be fabricated, formed or molded from a material such as HYDRAFLEX available from Raymedica Inc., 9401 James Avenue South, Suite 120, Minneapolis, Minn. 55431.

As another non-limiting example, the first implant body (2) and the second implant body (24) and the fixation member (18) can be configured as a material which exhibits controlled and consistent bulk and surface properties such as polymeric material CADISC or similar material by using proprietary precision polyurethane manufacturing technology available from Ranier Technology Limited, Greenhouse Park Innovation Centre, Newmarket Road, Teversham, Cambridge, CB5 8AA, U.K.

As another non-limiting example, the first implant body (2) and the second implant body (24) and the fixation member (18) can be fabricated, formed or molded from a material with biomimetic three-dimensional fabric with multiaxial fiber alignment such as FABRICUBE® by Takiron Co., Ltd., 3-13, Azuchimachi 2-chome, Chuo-ku, Osaka, 541-0052, Japan.

As another non-limiting example, the first implant body (2) and the second implant body (24) can be configured to have a surface, or a portion thereof, with a low coefficient of friction, on which a sacrum or ilium can articulate, and can be fabricated, formed or molded from a material such as PEEK, polyethylene, a ceramic or the like. Additionally, the first implant body (2) and the second implant body (24) can be configured to have a surface, or a portion thereof, coated in a chemical or biological substance or a combination thereof, which promotes the development of cartilage in order to provide a surface on a portion of a sacrum (4) or an ilium (3) with a low coefficient of friction on which the implant body may articulate, such as NUQU, which is composed of culture-expanded juvenile cartilage cells in a protein-based carrier, available from Isto Technologies, Inc., 1155 Olivette Executive Parkway, Suite 200, St. Louis, Mo. 63132, USA.

As another non-limiting example, the first implant body (2) and the fixation member (18) can be fabricated, formed or molded from a material by a method including the steps of providing, inserting, and positioning a device that includes an inflatable balloon which can be configured or adapted to non-transversely locate between the articular surfaces (16) or extra-articular surfaces (52) of the sacroiliac joint (47) or within an implant receiving space (50) surgically produced as further described below. Once positioned, the balloon can be filled with a curable biomaterial until the balloon expands to the desired size and dimensions, thereby transforming or already in the form of the first implant body (2) and the fixation member (18), whereupon the biomaterial is then permitted to fully cure in situ to form a final prosthesis having the aforementioned desired geometry and dimensions to substantially provide or restore the desired anatomy and function of the sacroiliac joint. The balloon can be fabricated as one layer or as two-layers and can be constructed as disclosed in WO/2002/017825. Likewise, a desirable curable biomaterial is also disclosed in the aforementioned reference. The desirable curable biomaterial selected exhibits elastic properties when submitted to the forces present in the joint. In embodiments where the balloon is constructed in two layers, the outer layer, or a portion thereof, may be configured for tissue ingrowth to fixate a first implant face (9) and a second implant face (10) to the sacrum (4) and ilium (3) while configuring the outer layer of a first implant side (7) and a second implant side (8) to inhibit bone ingrowth or ongrowth to prohibit potentially motion inhibiting bone bridging between the sacrum (4) and ilium (3). The inner layer of the balloon can be configured to contain the curable biomaterial. Consequently, the balloon and cured biomaterial selected can permit motion at the joint.

The various embodiments of the invention as exemplified by FIGS. 1 through 16, can provide a sufficient amount of surface area engageable with the corresponding surfaces of the bone of the sacrum (4) and ilium (5) upon implantation to substantially immobilize the sacrum (4) in relation to the ilium (5) or stabilize the sacrum (4) in relation to the ilium (3) while providing limited movement between mated parts of the implant embodiments to provide a corresponding limited movement of the sacrum (4) in relation to the ilium (3).

Again referring primarily to FIGS. 1 through 16, particular embodiments of the sacroiliac joint implant (1) can further include one or more aperture elements (30) which communicate between the opposed sides (22)(31) of the terminal member (21) or communicate between opposed sides (32)(33) of the projection member (19) or both. The amount of open space (34) of an aperture element (30) can be defined by an aperture perimeter (35) which can be of numerous and varied configurations of sufficient dimension to allow the bone of the ilium (3) or sacrum (4)(or both) to grow a distance into or through or fuse within or fuse to an amount of material (36) located within one or more of the aperture elements (30). The amount of material (36) can include: osseointegratable, osteoinductive, osteoconductive, osteogenic materials or biologically active agents, or combinations and permutation thereof.

As a non-limiting example, the aperture perimeter (35) can be of generally oval configuration resulting in an oval aperture element (30) located in the projection member (19) or terminal member (21). The length of the oval aperture element (30) can be aligned with the length of the projection member (19) or terminal member (21) and can for example be about one quarter to about two thirds the length of the fixation member (18). Additionally, the either or both of the first implant body (2) and the second implant body (24) can further include one or more aperture elements (30) which communicate between the external surfaces of the implant body (2)(24).

Again referring primarily to FIGS. 1 through 16, embodiments of the sacroiliac joint implant (1) can further include an anti-migration element (37) coupled to the external surface of to the first implant body (2) or the second implant body (24), or both. The anti-migration element (37) can take the form of an enlarged terminal portion of the second implant end (6) of the first implant body (2) or the second implant body (24), an increase in the projection member (19) (such as flaring outward) proximate the second implant end (6). As one non-limiting example, the anti-migration element (37) can take the form of an end cap (38) having a generally oval configuration coupled to the end of the terminal member (21) (see FIG. 16) which extends outward a sufficient distance to prevent advancement of the second implant end (6) of the sacroiliac joint implant (1) further into the joint between the sacrum (4) and the ilium (3) subsequent to implantation. As to embodiments which the fixation member (18) removably couples to the first implant body (2) or the second implant body (24) the end cap (38) can be configured to prevent the fixation member (18) from separating from first or second implant body (2)(24). While the end cap (38) shown in FIG. 16, is generally oval in configuration, the end cap (38) can have end cap perimeter (35) which defines an oval, square, rectangle, or other configuration useful in fixing the location of the sacroiliac joint implant (1) between the sacrum (4) and the ilium (3). Additionally, the end cap (38) can have sufficient dimensional relations to further include one or more bores (42) which communicate between opposed surfaces and dimensioned to receive mechanical fasteners (43)(such as threaded members, barbed members, locking members or the like) which can be driven or rotated to engage a portion of the sacrum (4) or the ilium (3), or in embodiments which the fixation member (18) removably couples to the first implant body (2) or second implant body (24) a portion of the mechanical fastener (43) can engage with the first or second implant body (2) (24), the bones of the sacrum (4) or ilium (3), or all of them (see for example FIG. 16). Now referring primarily to FIGS. 1 and 3, the anti-migration element (37) can also take the form of tapered elements (44) on a part or the entirety of the external surface which taper outward from the external surface of the sacroiliac joint implant (1) allowing insertion of embodiments between the sacrum (4) and the ilium (3) but opposes backward travel of the sacroiliac joint implant (1).

Embodiments of the sacroiliac joint implant (1) described herein can be fabricated or formed from a plurality of pieces or as a single piece of biocompatible material or a combination of biocompatible and biodegradable materials of suitably dimensioned particles, sheets, or other constructional forms machineable or formable or moldable materials suitably bound or formed or molded to provide configurations in accordance with the invention.

Again referring primarily to FIGS. 1-16, embodiments of the sacroiliac joint implant (1) can further include a coat (91) coupled, generated or integral to all or a part of the external surface of the sacroiliac joint implant (1). The coat (91) can be of any composition that can be coupled to the sacroiliac joint implant (1) capable of biocompatible osseointegration with the bone of the ilium (3) and sacrum (4), such as pure alumina, titanium-dioxide, hydroxyapatite, calcium triphosphate, or the like. As a non-limiting example, the coat (91) can be applied by plasma spraying with a plasma torch, a plasmatron or a plasma gun. Alternately, the coat (91) can be achieved by producing a surface roughness, porosity, or irregularity of the sacroiliac joint implant (1) by sand blasting, bead blasting, molding, or the like. The coat (91) can have a thickness in the range of about 40 μm and about 100 μm. Again, embodiments of the sacroiliac joint implant (1) can be configured as a material having interconnecting pores throughout such as TRABECULAR METAL available from Zimmer, P.O. Box 708, 1800 West Center Street, Warsaw, Ind. 46581-0708 or a metallic foam such as a titanium foam available from the National Research Council Canada, 1200 Montreal Road, Bldg. M-58, Ottawa, Ontario, Canada or fully-engineered, porous, titanium structures such as TRABECULITE available from Tecomet, 115 Eames Street, Wilmington, Mass. 01887.

Again referring primarily to FIGS. 1-15, embodiments of the invention can further include one or more bores (92) which communicate inwardly from a first implant end (5) useful for attachment of coupling elements (not shown) which may extend from embodiments of the sacroiliac joint implant (1) to join other portions of the skeleton or to other implants assist stabilizing the sacroiliac joint (47).

Again referring primarily to FIGS. 1-16, embodiments of the invention can further include one or more biologically active agent(s)(45) which can be applied directly to the external surface of the sacroiliac joint implant (1) or can be mixed with an amount of material (36) such as biocompatible material or biocompatible biodegradable material or biocompatible osseointegratable material which can be applied to the external surface of the sacroiliac joint implant (1) or otherwise made a part of the sacroiliac joint implant (1). As to particular embodiments of the sacroiliac joint implant (1), the biologically active agent(s)(45) can be mixed with the amount of material (36) and located within one or more of the aperture elements (30).

"Biocompatible" for the purposes of this invention means the ability of any material to perform the intended function of an embodiment of the invention without eliciting any undesirable local or systemic effects on the recipient and can include non-biodegradable materials such as: ceramic; metals or steels such as titanium alloys or rigid polymeric materials or rigid laminate materials or composites which include suitably dimensioned particles of metals or steels dispersed within rigid laminate materials, or suitably sized particles of biocompatible materials suitably bound or formed to provide configurations, polyurethanes, polyisobutylene, ethylene-alpha-olefin copolymers, acrylic polymers and copolymers, vinyl halide polymers and copolymers, polyvinyl esters, polyvinylidene chloride, polyacrylonitrile, polyvinyl ketones, polyvinyl aromatics such as polystyrene, copolymers of vinyl monomers and olefins such as ethylene-methyl methacrylate copolymers, acrylonitrile-styrene copolymers, ABS resins, ethylene-vinyl acetate copolymers, polyamides such as Nylon 66 and polycaprolactone, alkyd resins, polycarbonates, polyoxyethylenes, polyimides, polyesters, epoxy resins, rayon-triacetate, cellophane, polyether ether ketone (PEEK), polyetherketoneketone (PEKK), bone-from-wood available from the Istituto di Scienza e Tecnologia dei Mareriali Ceramici, Faenza, Italy, or the like, or biodegradable materials, as herein described.

"Biodegradable" for the purposes of this invention means the ability of any biocompatible material to breakdown within the physiological environment of the sacroiliac joint by one or more physical, chemical, or cellular processes at a rate consistent with providing treatment of a condition of the sacroiliac joint at a therapeutic level controllable by selection of a polymer or mixture of polymers (also referred to as polymeric materials), including, but not limited to: polylactide polymers (PLA), copolymers of lactic and glycolic acids (PLGA), polylactic acid-polyethylene oxide copolymers, poly(ε-caprolactone-co-L-lactic acid (PCL-LA), glycine/PLA copolymers, PLA copolymers involving polyethylene oxides (PEO), acetylated polyvinyl alcohol (PVA)/polycaprolactone copolymers, hydroxybutyrate-hydroxyvalerate copolymers, polyesters such as, but not limited to, aspartic acid and different aliphatic diols, poly (alkylene tartrates) and their copolymers with polyurethanes, polyglutamates with various ester contents and with chemically or enzymatically degradable bonds, other biodegradable nonpeptidic polyamides, amino acid polymers, polyanhydride drug carriers such as, but not limited to, poly(sebacic acid) (PSA), aliphatic-aromatic homopolymers, and poly(anhydride-co-imides), poly(phosphoesters) by matrix or pendant delivery systems, poly (phosphazenes), poly(iminocarbonate), crosslinked poly(ortho ester), hydroxylated polyester-urethanes, or the like.

"Biologically active agents" for the purposes of this invention means those agents or mixture of agents which can be varied in kind or amount to provide a therapeutic level effective to mediate the formation or healing of bone, cartilage, tendon, or to reduce, inhibit, or prevent a symptom of a condition of the sacroiliac joint subsequent to placement of an embodiment of the implant within the sacroiliac joint (1) such as infection or pain and without limitation can include agents that influence the growth of bone, demineralized bone matrix, stem cells, alleografts, bone forming protein, bone morphogenetic protein 2, bone morphogenic protein 7, analgesics, anesthetics, anti-inflammatory agents, antibacterials, antivirals, antifungals, antiprotozoals, anti-infectives, antibiotics such as aminoglycosides such as gentamicin, kanamycin, neomycin, and vancomycin; amphenicols such as chloramphenicol; cephalosporins, such as cefazolin HCl; penicillins such as ampicillin, penicillin, carbenicillin, oxycillin, methicillin; lincosamides such as lincomycin; polypeptide antibiotics such as polymixin and bacitracin; tetracyclines such as tetracycline, minocycline, and doxycycline; quinolones such as ciprofloxacin, moxifloxacin, gatifloxacin, and levofloxacin; anti-viral drugs such as acyclovir, gancyclovir, vidarabine, azidothymidine, dideoxyinosine, dideoxycytosine; analgesics, such as codeine, morphine, ketorolac, naproxen, an anesthetic, lidocaine; cannabinoids; antifungal agents such as amphotericin; anti-angiogenesis compounds such as anecortave acetate; retinoids such as tazarotene, steroidal anti-inflammatory agents such as 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide; or allograft cellular matrix containing viable mesenchymal stem cells such as OSTEOCEL PLUS available from NuVasive, Inc., 7475 Lusk Blvd., San Diego, Calif. 92121 USA, and any of their derivatives, whether separately or in combinations thereof.

As to particular embodiments of the inventive implant (1) the biologically active agent(s)(45) can be dispersed throughout the amount of material (36) whether a biocompatible or biocompatible biodegradable material (or mixture of biocompatible materials or mixture of biocompatible biodegradable materials) by mixing biologically active agent(s)(45) into a melted biocompatible or biodegradable polymer and then solidifying the resulting material (36) by cooling, to substantially uniformly disperse the biologically active agent(s)(45) substantially throughout the material (36). The biodegradable material or biocompatible material or mixture thereof can be selected to have a melting point that is below the temperature at which the biologically active agent(s)(45) becomes reactive or degrades. Alternatively, the biologically active agent(s)(45) can be dispersed throughout the biocompatible or biodegradable material by solvent casting, in which the biocompatible or biodegradable material is dissolved in a solvent, and the biologically active agent(s)(45) dissolved or dispersed in the solution. The solvent can then be evaporated, leaving the biologically active agent(s)(45) in the matrix of the material (36). Solvent casting requires that the biocompatible or biodegradable material be soluble in organic solvents. Alternatively, the sacroiliac joint implant (1) can be placed in a solvent having a concentration of the biologically active agent(s)(45) dissolved and in which the sacroiliac joint implant (1) or the biocompatible or biocompatible biodegradable material (36) located in one or more of the aperture elements (30), or applied to the external surface, swells. Swelling of the sacroiliac joint implant (1) or portions thereof can draw in an amount of the biologically active agent(s)(45). The solvent can then be evaporated leaving the biologically active agent(s)(45) within the biocompatible or biocompatible biodegradable material (36). As to each method of dispersing the biologically active agent(s)(45) throughout the biocompatible or biodegradable biocompatible material (36) of or coupled to the sacroiliac implant (1), therapeutic levels of biologically active agent(s)(45) can be included in biocompatible biodegradable material (36) to provide therapeutically effective levels of the biologically active agent(s)(45) to the sacroiliac joint to treat a particular sacroiliac joint condition.

Other non-active agents (46) may be included in the biocompatible biodegradable material for a variety of purposes. For example, buffering agents and preservatives may be employed. Preservatives which may be used include, but are not limited to, sodium bisulfate, sodium bisulfate, sodium thiosulfate, benzalkonium chloride, chlorobutanol, thimerosal, phenylmercuric acetate, phenylmercuric nitrate, methylparaben, polyvinyl alcohol and phenylethyl alcohol. Examples of buffering agents that may be employed include, but are not limited to, sodium carbonate, sodium borate, sodium phosphate, sodium acetate, sodium bicarbonate, and the like, as approved by the FDA or other appropriate agencies in the United States or foreign countries, for the desired route of administration. Electrolytes such as sodium chloride and potassium chloride may also be included in the formulation.

A non-limiting example, embodiments of the sacroiliac joint implant (1) having a biocompatible biodegradable portion with biologically active agent(s)(45) for treating the sacroiliac joint (47)(also referred to as the "implant") can be made by dispersing a biologically active agent(s)(45) in a biocompatible biodegradable material (36) as above described to provide biologically active agent(s)(45) release characteristics at a therapeutic level. Upon implantation of the sacroiliac joint implant (1), as described below, the biocompatible biodegradable portion of the sacroiliac joint implant (1) can substantially continuously release biologically active agent(s)(45) to provide a localized amount of bone morphogenetic protein 2 at therapeutic levels of about 1 milligram to about 4 milligrams to facilitate bone regrowth. It is to be understood that this specific example of providing an embodiment of the sacroiliac joint implant (1) which delivers an amount of bone morphogenetic protein 2 to facilitate bone regrowth, is not intended to be limiting, and embodiments of the implant (1) can be utilized to deliver numerous and varied active agent(s)(45) individually or in combination to treat a wide range of conditions of the sacroiliac joint (47) subsequent to implantation of embodiments of the implant (1).

Again referring primarily to FIG. 11-16, particular embodiments of the invention can further include an amount of curvature (15) between the first implant end (5) and the second implant end (6) of the inventive implant (1). The amount of curvature (15) can vary from embodiment to embodiment of the inventive implant (1) depending on the application, between a substantially linear body as above described and shown in FIGS. 1-7 to including an amount of curvature (15) which defines a radius (51) to facilitate placement in the cranial portion (48) and caudal portion (49) between the articular surfaces (16) of the sacroiliac joint (47) or in the corresponding implant receiving space (50), as further described below. As one non-limiting embodiment the radius (51) can be within a range of about 2 cm and about 6 cm.

Now referring primarily to FIG. 16, certain embodiments of the invention having an amount of curvature (15) can be provided in a plurality of implant segments (17) which can be individually implanted within the articular region (16). Understandably, embodiments of the inventive sacroiliac joint implant (1) whether separately or in joined relation, whether the same or different embodiments, can be utilized with conventional or the inventive methods of implantation herein described for stabilization and to permit movement of the sacroiliac joint (47).

Now referring primarily to FIGS. 17-41, particular embodiments of sacroiliac joint implant (1) can be configured to provide a sacral member (53) having a sacral fixation surface (54) which can engage the sacrum (4) and a iliac member (55) having a iliac fixation surface (56) which can engage the ilium (3). The sacral fixation surface (54) and the iliac fixation surface (56) can be configured or adapted to non-transversely locate between the articular surfaces (16) or extra-articular surfaces (52) of the sacroiliac joint (47) or within an implant receiving space (50) surgically produced as further described below by removal of a portion the articular cartilage or bone of the ilium (3) or the sacrum (4)(or both) to correspondingly engage a portion of the sacrum (4) and the ilium (3). The sacral member (53) and the iliac member (55) can further correspondingly provide a sacral member interface surface (57) and an iliac member interface surface (58) which can disposed in opposed slidable mated relation. Upon implantation of such embodiments between the articular surfaces (16) or between the extra-articular surfaces (52) opposed slidable mated engagement of the sacral member interface surface (57) and the ilium member interface surface (58) can afford a limited amount of travel between the sacral member (53) and the iliac member (55) of the implant (1).

For the purposes of this invention, the term "non-transversely" as used herein means not lying or extended across the joint between the sacrum (4) and the ilium (5) and in particular does not include trans-iliac placement of a sacroiliac joint implant (1). The term "articular surfaces" includes the two paired L-shaped surfaces formed between the surfaces of the sacrum (4) and the ilium (3) having a cranial portion (48) and a caudal portion (49) as shown for example in FIGS. 43-47 (within the broken line). The term "extra-articular surfaces" includes structures or regions of the sacrum (4) or the ilium (3) outside of the articular surfaces (16), such as, the paired iliac tuberosity and sacral fossa.

Referring primarily to FIGS. 17-23, a particular embodiment of implant (1) is shown which includes a sacral member (53) and an iliac member (55) each having separately and in mated relation sufficient dimensions to avoid deformation under the normal forces of surgical placement and stabilization of the ilium (3) in relation to the sacrum (4). Accordingly, while the embodiment of the sacroiliac joint implant (1) shown in FIGS. 17-23 provides the sacral member (53) and the iliac member (55) as a pair of mirror image quadrilateral polygons each having a first side (59) and a second side (60) disposed in substantially perpendicular relation and a third side (61) of lesser length than said first or second sides (59)(60). A fourth side (62) connects the second and third sides (60)(61) in angled relation. Each of the iliac member (55) and the sacral member (53) dispose the corresponding fixation surface (54)(56) and interface surfaces (57)(58) in substantially parallel opposed relation a distance apart affording sides (59)(60)(61)(62) each having a general rectangular configuration. The quadrilateral polygon as described can have dimensional relations which allow implantation between the extra-articular surfaces (52) of the sacrum (4) and the ilium (3) as shown in the non-limiting example of FIG. 47. As one non-limiting example, the implant (1) having the quadrilateral form above described with the sacral member (53) and the ilium member (55) interface surfaces (57)(58) in mated engagement as shown in FIGS. 18 and 19 can have a width (63)(see FIG. 18) in the range of about 0.5 cm centimeters ("cm") and about 2 cm and a height (64)(see FIG. 17) in the range of about 1 cm to 5 cm and a length (65) (see FIG. 17) disposed between a first implant end (5) and a second end (6) in the range of about 3 cm and about 6 cm. The sacral member interface surface (57) and the ilium member interface surface (58) can be substantially flat; however the invention is not so limited and interface surfaces (57)(58) can further include a matable convex surface element (66) or concave surface elements (67) which limits travel of the sacral member (53) in relation to the iliac member (54).

Now referring primarily to FIGS. 24-35, embodiments of the sacroiliac joint implant (1) providing a sacral member (53) having a sacral fixation surface (54) which can engage the sacrum (4) and an iliac member (55) having a ilium fixation surface (56) which can engage the ilium (3). The sacral member (53) and the iliac member (55) can have an amount of curvature (15) between a first implant end (5) and a second implant end (6). The implant can have dimensional relations and curvature to allow implantation between the articular surfaces (16) of the sacrum (4) and the ilium (3) as shown in the non-limiting example of FIG. 45. The sacral member interface surface (57) and the iliac member interface surface (58) can correspondingly provide a channel element (68) and a guide element (69), the guide element (69) configured to be received within the channel element (68). Depending upon the configuration of the guide element (69) and the channel element (68), the guide element (69) can travel within the channel element (68) to provide a corresponding amount of movement of the sacral member (53) in relation to the iliac member (55).

While the embodiment of the implant (1) shown in FIG. 24 through FIG. 29 shows a continuous channel element (68) which receives a correspondingly continuous guide element (69); the invention is not so limited and embodiments of the implant (1) a plurality of channel elements (68) discontinuous from each other and correspondingly receiving a plurality of guide elements (69) as shown for example in FIGS. 30-35.

Again referring to FIGS. 30-35, certain configurations of the channel element (68) can be configured to slidely mate in an interlocked configuration which upon implantation does not afford disengagement of the guide element (69) from the channel element (68). Now referring primarily to FIG. 35, a non-limiting embodiment of the channel element (68) can have channel walls (71)(72) which are disposed a lesser distance apart proximate the interface surface (57) or (58) and a greater distance apart proximate the channel bottom (73) a correspondingly configured guide element (69) can have greater dimension proximate the guide end terminal (74) and a lesser dimension at the guide base (75). As one example the guide element (69) can provide a first cylindrical member (76) (see FIGS. 30 and 35) which projects outwardly a first distance from the interface surface (57) or (58) and terminates in a second cylindrical member (77) of greater diameter which extends a second distance from the interface surface (57) or (58). The channel walls (71)(72) proximate the channel bottom (73) can be disposed a sufficient distance apart to receive between the second cylinder member (77) and the channel walls (71)(72) can step inwardly proximate the interface surface (57) or (58) to dispose the channel walls (71)(72) a sufficient distance apart to receive between the first cylindrical member (76) but sufficiently close together to prevent the first cylindrical member (76) to pass between, thereby interlocking the guide element (69) within the channel element (68). As another non-limiting example the channel element (68) can be configured as a dovetail slide and the guide element as a dovetail. As shown in FIGS. 30 through 35, the corresponding sacral member interface element (57) and iliac member interface element (58) can each provide generally flat interface surfaces disposed in opposed parallel relation external to the channel (68) and guide element (69).

Again referring primarily to FIGS. 24 through 29, particular embodiments of iliac member interface surface (58) can further provide a convex element (66) having a generally circular configuration in cross section disposed generally along the midline of the iliac member interface surface (58). The channel element (68) can be disposed to generally bisect the convex element (66) providing a generally curved convex interface surface (76) on either side of the channel element (68). The curved convex interface surface (76) can matably engage a corresponding concave element (66) disposed generally along the midline of the sacral member interface surface (58). The guide element (69) can generally bisect the concave element (66) to provide a curved concave interface surface (78) on either side of the guide element (69). Upon engagement of the sacral member interface surface (57) with the iliac member interface surface (58) the curved concave interface surface (78) can have limited rotation in relation to the curved convex interface surface (76) to correspondingly afford movement of the sacral member (53) in relation to the iliac member (55). The iliac member interface surface (58) can further include a ridge element (79) disposed along the perimeter of the curved convex interface surface (76). The sacral member interface surface (57) can further include a ridge receiving element (80) which receives the ridge element (79) upon mated engagement of the sacral member interface surface (57) with the iliac member interface surface (58).

As to embodiments as shown in FIGS. 24-29, the channel element (68) can have a width $W_1$ and the guide element (69) can have a lesser width $W_2$. The widths $W_1$ and $W_2$ can be adjusted in relation to each other provide an amount of longitudinal movement of the guide element (69) in the channel element (68) and an amount of rotation of the curved concave interface surface (78) over the curved convex interface surface (76). The ridge element (79) and the ridge receiving element (80) can be configured to further adjust the direction and amount of movement between the sacral member (53) and the iliac member (55).

Now referring primarily to FIGS. 36-41, an embodiment of an inventive sacroiliac joint implant (1) is shown which in part can include a sacral member (53) and an iliac member (55). The sacral member (53) and the iliac member (55) can have an amount of curvature (15) between a first implant end (5) and a second implant end (6). The implant (1) can have dimensional relations and curvature to allow implantation between the articular surfaces (16) of the sacrum (4) and the ilium (3) as shown in the non-limiting example of FIG. 45 (broken line). The sacral member interface surface (57) and the iliac member interface surface (58) can correspondingly provide a sacral member core receiving element (81) and an iliac member core receiving element (82) each configured as an elongate curved recess which as to particular embodiments can be configured as an elongate curved semi-cylinder or elongate curved semi-oval recess. The implant (1) can further include a core element (83) having a core body (84) received in part by the sacral member core receiving element (81) and in part by the iliac member core receiving element (82) upon mated engagement of the sacral member interface surface (57) and the iliac member interface surface (58). The core body (84) can be correspondingly configured to provide an elongate curved cylinder or oval which can have sufficient dimensions when received within the iliac member core receiving element (82) and the sacral member core receiving element (81) to dispose the interface surfaces (57)(58) outside of the perimeter of the core receiving elements (81)(82) a distance apart.

The core body (84) can further include a continuous or discontinuous circumferential radially extending fin (85). The core fin (85) can have a thickness which maintains the interface surfaces (57)(58) outside of the core receiving elements (81)(82) a distance apart. The core body (84) and the core fin (85) can be configured from the same or similar material as the sacral member (53) and the iliac member (55) but can also be made from a material which affords the core body (84) and the core fin (85) an amount of flexure or an amount of compression in response to movement of the sacral member (53) and the iliac member (55). As a non-limiting example, the core body (84) and the core fin (85) can be fabricated, formed or molded from materials such as polyethylene.

Again referring primarily to FIGS. 17 through 41, embodiments of the sacroiliac joint implant (1) can further include a sacral member fixation element (86) coupled to the sacral member fixation surface (54) or a iliac member fixation element (87) coupled to the iliac member fixation surface (56). The sacral member fixation element (86) can extend outwardly a sufficient distance to be disposed within the bone of the sacrum (4). The iliac member fixation element (87) can extend outwardly a sufficient distance to be disposed within the bone of the ilium (3). As to certain embodiments of the sacroiliac joint implant (1) as shown in FIGS. 17-23, the sacral or iliac fixation element (86)(87) can take the form of a projection member (19) and can further include a terminal member (21) as above described.

Now referring primarily to FIGS. 42A-C and 43-45, and incorporating by reference U.S. patent application Ser. No. 12/998,712, placement of various embodiments of the sacroiliac joint implant (1), above described, can be achieved by accessing an articular region (88) between the articular surfaces (16) (shown in broken line) of FIGS. 43-47 of the sacroiliac joint (47). The various embodiments of the, a sacroiliac joint implant (1) can be implanted non-transversely between the articular surfaces (16) within the articular region (88) of the sacroiliac joint (47) to dispose the sacrum (4) and the ilium (3) in substantially immobilized relation by corresponding engagement of the sacroiliac joint implant (1) by the articular surfaces (16) of the sacroiliac joint (47). The particular example of the method described is sufficient to enable a person of ordinary skill in the art to utilize embodiments of the sacroiliac joint implant (1) and is not intended to be limiting with respect to the order of steps or the use of all or any of the steps or combination of one or more steps into one steps or performing any one step as substeps, or other similar, equivalent, or conventional steps to implant embodiments of the sacroiliac joint implant (1) within the sacroiliac joint (47).

Now referring primarily to FIGS. 42A-C and 43-47, an embodiment of the method of implanting the various embodiments of the sacroiliac joint implant (1) can include the step of placing a patient under sedation prone on a translucent operating table (or other suitable surface). The sacroiliac joint (47) can be locally anesthetized to allow for injecting a radiographic contrast (as a non-limiting example, Isoview 300 radiographic contrast) under fluoroscopic guidance into the inferior aspect of the sacroiliac joint (47) to outline the articular surfaces (16) of the sacroiliac joint (47). Injection of the radiographic contrast within the sacroiliac joint (47) can be accomplished utilizing a tubular member (such as a syringe needle) having first tubular member end which can be advanced between the articular surfaces (16) of the sacroiliac joint (47) and having a second tubular member end which removably couples to a hub. The hub can be configured to removably couple to a syringe barrel (or other device to contain and deliver an amount of radiographic contrast). In the example of a syringe barrel, the syringe barrel can have an internal volume capable of receiving an amount of the radiographic contrast sufficient for outlining the lateral articular surfaces of the sacroiliac joint. A plunger can be slidingly received within the barrel to deliver the radiographic contrast through the tubular member into the sacroiliac joint. The tubular member can have a gauge in the range of about 16 gauge and about 20 gauge and can further be incrementally marked on the external surface to allow determination of the depth at which the first needle end has advanced within the sacroiliac joint (47). As the first needle end advances into the sacroiliac joint (47) the radiographic dye can be delivered from within the syringe barrel into the sacroiliac joint to allow visualization of the sacroiliac joint (47) and location of the tubular needle within the sacroiliac joint (47).

Once the first tubular member end has been sufficiently advanced into the sacroiliac joint and the articular surfaces (16) of the sacroiliac joint (47) have been sufficiently visualized, the hub can be removed from the tubular member leaving the tubular member fixed within the sacroiliac joint (47) as a initial guide for tools subsequently used to locate or place the sacroiliac joint implant (1) non-transversely between the articular surfaces (16) of the sacroiliac joint (47) or in removal of a portion of the sacroiliac joint (47) within the region defined by the articular surfaces (16) to generate an implant receiving space (50). Alternately, one or more guide pins (14) can be inserted along substantially the same path of the tubular member for fixed engagement within the sacroiliac joint (47) and used in subsequent steps as a guide(s).

A small incision can be made in the skin at the posterior superior (or as to certain embodiments inferior) aspect of the sacroiliac joint (47), extending proximal and distal to the tubular member along the line of the sacroiliac joint to provide a passage to access the interarticular space between the articular surfaces (16) of the sacroiliac joint (47). A cannulated probe can be slidingly engaged with the tubular member (or guide pin (14)) extending outwardly from the sacroiliac joint (while the sacroiliac joint (47) may be shown in the figures as being substantially linear for illustrative purposes, it is to be understood that the normal irregular features of the sacroiliac joint (47) have not been removed). The cannulated probe can have a probe body of generally cylindrical shape terminating in a spatulate tip at the end advanced into the sacroiliac joint. A removable cannulated probe handle couples to the opposed end of the probe body. The spatulate tip can be guided along the tubular needle (or guide wire) into the posterior portion of the sacroiliac joint and advanced to the anterior portion of the sacroiliac joint under lateral fluoroscopic visualization. The cannulated probe handle can then be removed providing the generally cylindrical probe body extending outwardly from the sacroiliac joint (47) through the incision made in the skin.

A passage from the incision to the sacroiliac joint (47) can be generated by inserting a cannula into the incision. A soft tissue dilator having a blunt end can be advanced over the probe body, or a plurality of soft tissue dilators of increasing size, until the blunt end of the soft tissue dilator and the corresponding cannula end contact the posterior aspect of the sacroiliac joint. The soft tissue dilator can be removed from within the cannula. The external surface of the cannula can be sufficiently engaged with the surrounding tissue to avoid having the tissue locate with in the hollow inside of the cannula. A non-limiting embodiment of the cannula provides a tubular body having substantially parallel opposed side walls which terminate in a radius at both ends (lozenge shape) into which a plurality of different jigs can be inserted.

A cannula alignment jig can be advanced over the probe body (or guide pins (14)) and received within the cannula. Substantially, identical cross hairs can be disposed on the upper jig surface and the lower jig surface. Alignment of the cross hairs under x-ray with the corresponding anterior and posterior joint lines of the sacroiliac joint can confirm that the cannula has proper orientation in relation to the paired articular surfaces of the sacroiliac joint (47). The cannula properly oriented with the paired articular surfaces (16) can then be disposed in fixed relation to the sacroiliac joint (47) by placement of fasteners through the cannula into the sacrum (4) or the ilium (3).

A first drill jig can be advanced over the probe body (or guide pins (14)) and received within the cannula. The probe body (or guide pins (14)) extending outwardly from the sacroiliac joint (47) passes through a drill guide hole of the first drill jig (or a plurality of guide pins (14)) can extend through a corresponding plurality of guide pin holes. The drill guide hole can take the form of a circular hole, a slot, or other configuration to restrict the movement of the drill bit within the drill jig and provide a guide for a drill bit in relation to the sacroiliac joint (47).

A cannulated drill bit can be advanced over the probe body and within a drill guide hole of the first drill jig. The cannulated drill bit under fluoroscopic guidance can be advanced into the interarticular region (88) between the articular surfaces (16) of the sacroiliac joint (47) to produce a first bore to a determined depth. As to certain embodiments of the method, an amount of articular cartilage or other tissues from between the articular surfaces (16) of the sacroiliac joint (47) can be removed sufficient to allow embodiments of the sacroiliac joint implant (1) to be implanted in replacement of the removed articular cartilage or tissue. Because the method removes the degenerative articular cartilage or tissue between the articular surfaces (16) of the sacroiliac joint (47), the articular surfaces (16) of the sacroiliac joint (47) can remain intact or substantially intact allowing the sacroiliac joint implant (1) to be non-transverely located between the articular surfaces (16) of the sacroiliac joint (47). Understandably, other instruments can be utilized separately or in combination with a cannulated drill bit for the removal of articular cartilage or tissue between articular surfaces (16) such as: box chisels, burs, hole saws, curettes, lasers (such as CO2, Neodymium/YAG (yttrium-aluminum-garnet), argon, and ruby), electrosurgical equipment employing electromagnetic energy (the cutting electrode can be a fine micro-needle, a lancet, a knife, a wire or band loop, a snare, an energized scalpel, or the like) where the energy transmitted can be either monopolar or bipolar and operate with high frequency currents, for example, in the range of about 300 kHz and about 1000 kHz whether as pure sinusoidal current waveform where the "crest factor" can be constant at about 1.4 for every sinus waveform, and a voltage peak of approximately 300 V to enable a "pure" cutting effect with the smallest possible coagulation effect or as amplitude modulated current waveforms where the crest factor varies between 1.5 and 8, with decreasing crest factors providing less of a coagulation effect. Electrosurgical waveforms may be set to promote two types of tissue effects, namely coagulation (temperature rises within cells, which then dehydrate and shrink) or cut (heating of cellular water occurs so rapidly that cells burst). The proportion of cells coagulated to those cut can be varied, resulting in a "blended" or "mixed" effect. Additionally, a fully rectified current, or a partially rectified current, or a fulguration current where a greater amount or lateral heat is produced can be employed to find the articular surfaces (16) of the sacroiliac joint (47) and aid in advancing a probe or guide wire into a position in between the articular surfaces (16). These currents can effectively degrade the cartilage and allow advance into the joint without grossly penetrating much beyond the cartilage.

As to certain embodiments of the invention, the first drill jig can be removed from within the cannula and a second drill jig can be advanced over the probe body and received within the cannula; however, the invention is not limited to any particular number of drill jigs and as to certain embodiments of the method the first drill jig can include all the required drill guide hole(s)(or slots or other configurations of the drill guide) and as to other embodiments of the method a plurality of drill jigs can be utilized in serial order to provide all the drill guide holes.

The first drill jig can provide one or more additional drill guide holes which guide in relation to the first bore a second or more cannulated drills of the same or different configuration to be inserted within and advanced into the sacroiliac joint (47) to produce a second bore or a plurality of bores within the sacroiliac joint (47) spaced apart in predetermined pattern to allow removal of sufficient articular cartilage or other tissue from the interarticular space (89) of sacroiliac joint (47) for placement of embodiments of the sacroiliac joint implant (1) within the region defined by and between the paired articular surfaces (16) of the sacroiliac joint (47). As to certain methods of the invention, the first drill jig or the second drill jig or a plurality of drill jigs can be utilized in serial order to remove a portion of the sacroiliac joint (47) for generation of an implant receiving space (50).

As these embodiments of the method, articular cartilage or other tissues and sufficient subchondral bone can be removed from between the articular surfaces (16) of the sacroiliac joint (47) sufficient to allow placement of certain embodiments of the sacroiliac joint implant (1) and one or more fixation member receiving channels (90) can be cut into at least one of the articular surfaces (16) of said sacroiliac joint (47) sufficient to receive other embodiments of the sacroiliac implant (1). The one or more fixation member receiving channels (90) can be cut a depth into the subchondral, cortical bone or cancellous bone of the sacrum (4) or ilium (3).

In a subsequent step, the last in the serial presentation of drill jigs can be removed from within the cannula and a broach jig can be advanced over the probe body to locate within the cannula. The broach jig can include a broach guide hole which receives a first broach end of a cannulated broach advanced over the probe body. The first broach end can have a configuration which can be advanced into the sacroiliac joint (47). As to certain embodiments of the method, the first broach end can be adapted to remove an amount of articular cartilage and other tissue from the between the articular surfaces (16) within the articular region (88) of the sacroiliac joint (47) for non-transverse placement of a sacroiliac joint implant (1) between the articular surfaces (16) of the sacroiliac joint (47). As to other embodiments of the method, the cannulated broach can remove a sufficient a portion of the sacroiliac joint (47) to generate an implant receiving space (50) to receive embodiments of the sacroiliac joint implant (1) between the articular surfaces (16). The broach can be configured to remove a portion of the sacroiliac joint (47) to produce a implant receiving space (50) to receive embodiments of the sacroiliac joint implant (1) having a sacral member fixation element (86) and a iliac member fixation element (87) adapted to locate between the articular surfaces (16) of the sacroiliac joint (47).

Figure 42A:
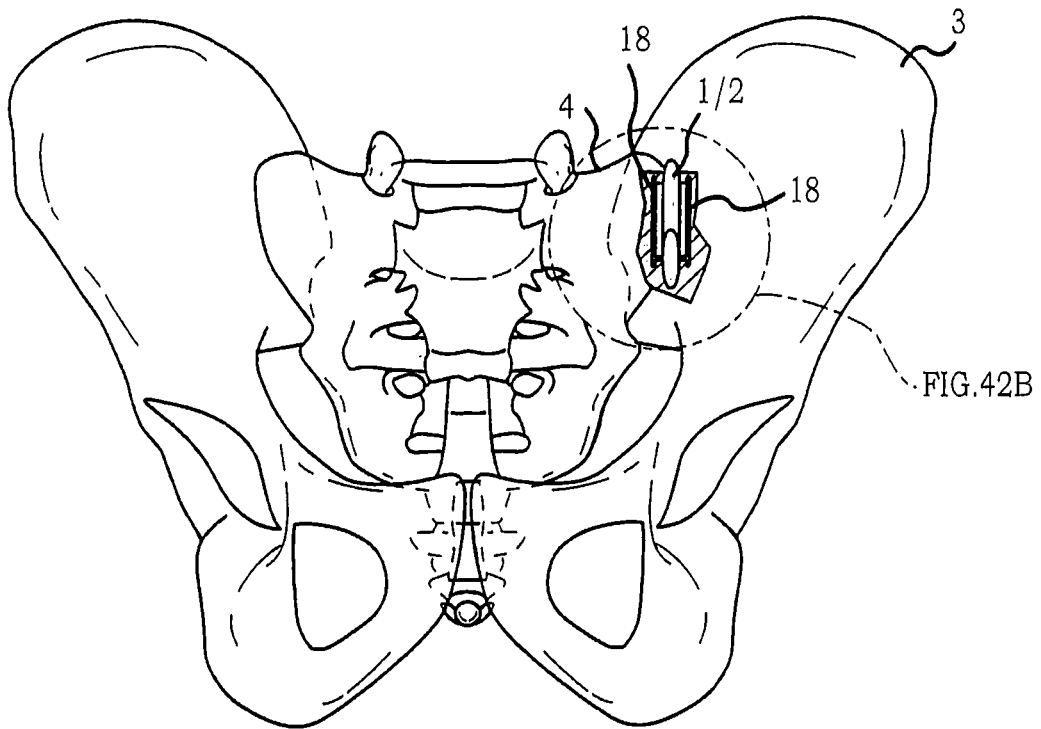
FIG. 42A is a cutaway view of the sacroiliac joint showing placement of a particular embodiment of the sacroiliac joint implant implanted between the articular surfaces of the sacroiliac joint.
Figure 42B:
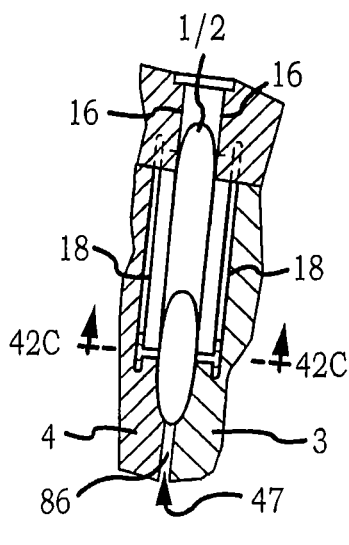
FIG. 42B is an enlarged cutaway view of FIG. 42A showing placement of a particular embodiment of the sacroiliac joint implant implanted between the articular surfaces of the sacroiliac joint.
Figure 42C:
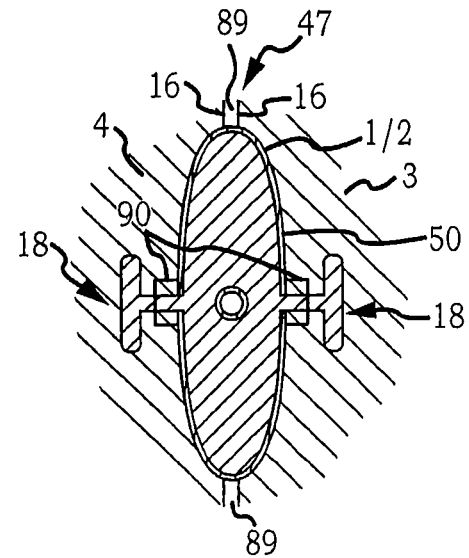
FIG. 42C is a cross section 42C-42C shown in FIG. 42B showing placement of a particular embodiment of the sacroiliac joint implant between the articular surfaces of the sacroiliac joint or within an implant receiving space established between the articular surfaces of the sacroiliac joint.
Figure 43:
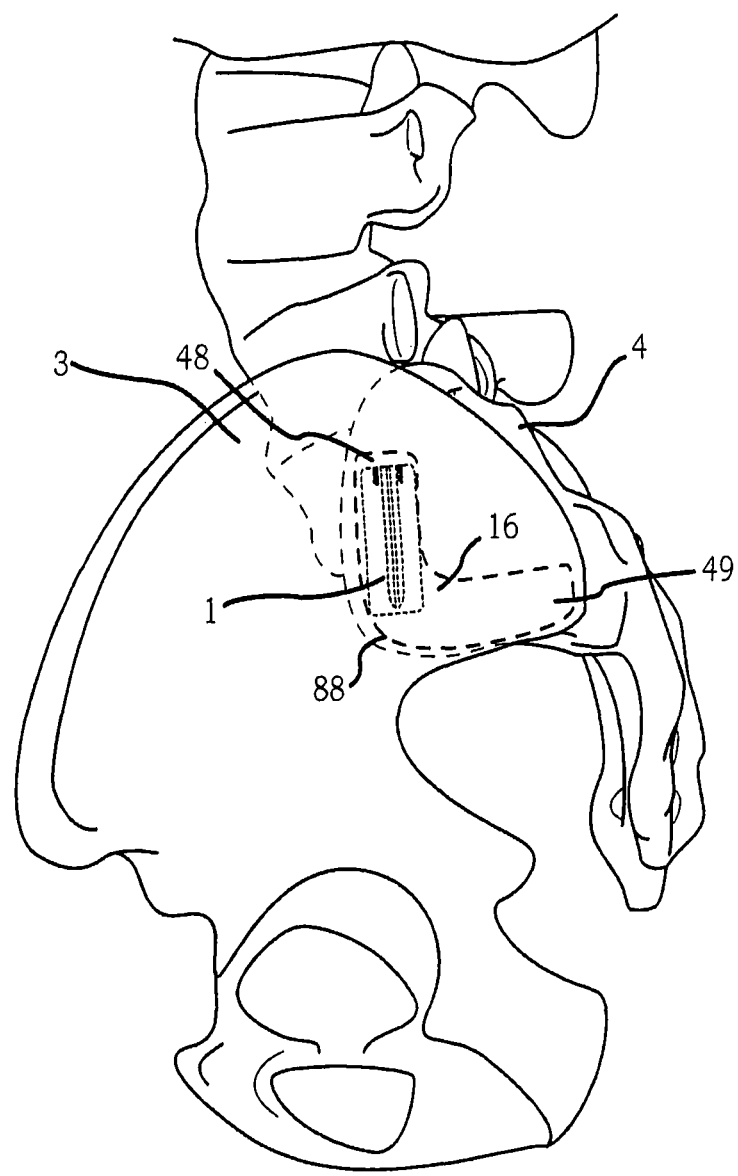
FIG. 43 is a side view of the ilium with the articular region shown bounded by broken line showing placement of an embodiment of the sacroiliac joint implant in the cranial portion of the articular region between the articular surfaces of the sacroiliac joint.
Figure 44:
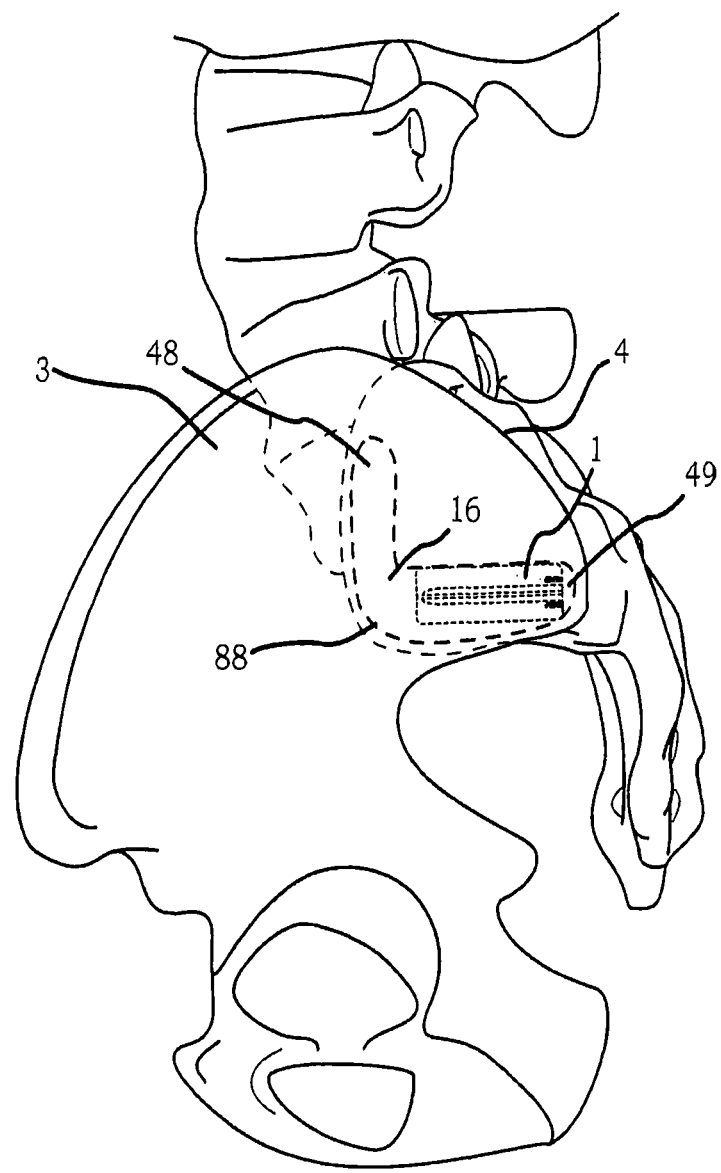
FIG. 44 is a side view of the ilium with the articular region shown bounded by broken line showing placement of an embodiment of the sacroiliac joint implant in the caudal portion of the articular region between the articular surfaces of the sacroiliac joint.
Figure 45:
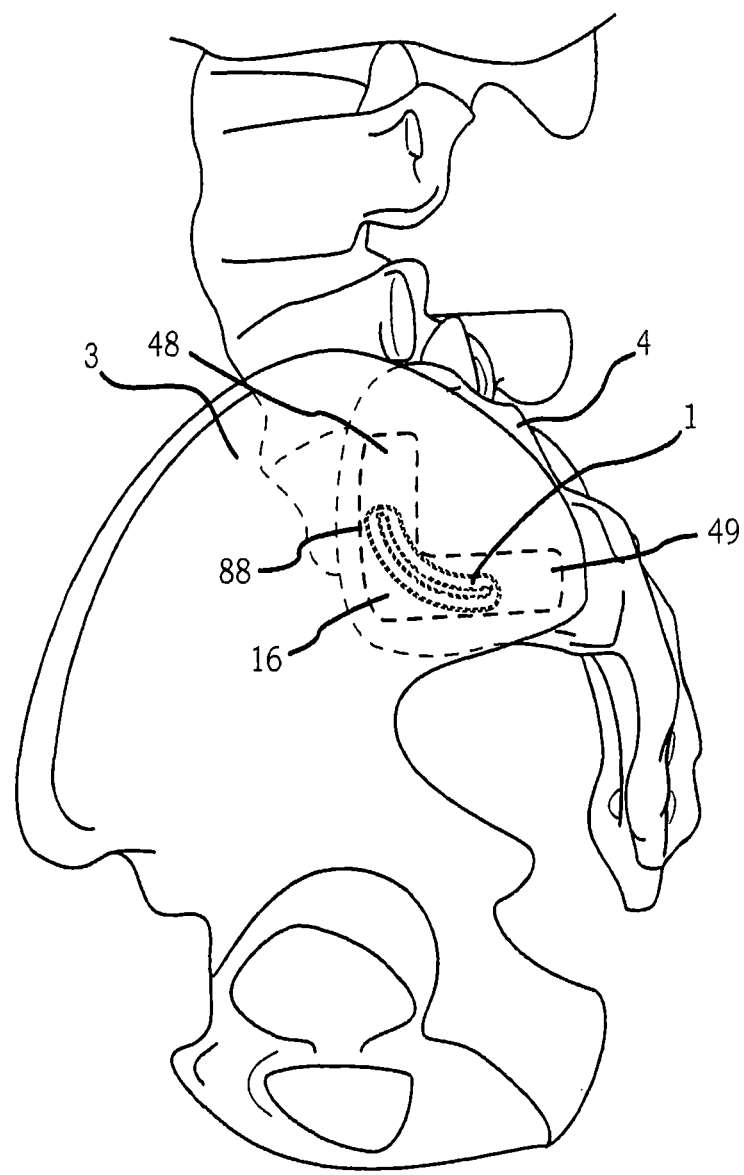
FIG. 45 is a side view of the ilium with the articular region shown bounded by broken line showing placement of an embodiment of the sacroiliac joint implant in both the cranial portion and caudal portions of the articular region between the articular surfaces of the sacroiliac joint.
Figure 46:
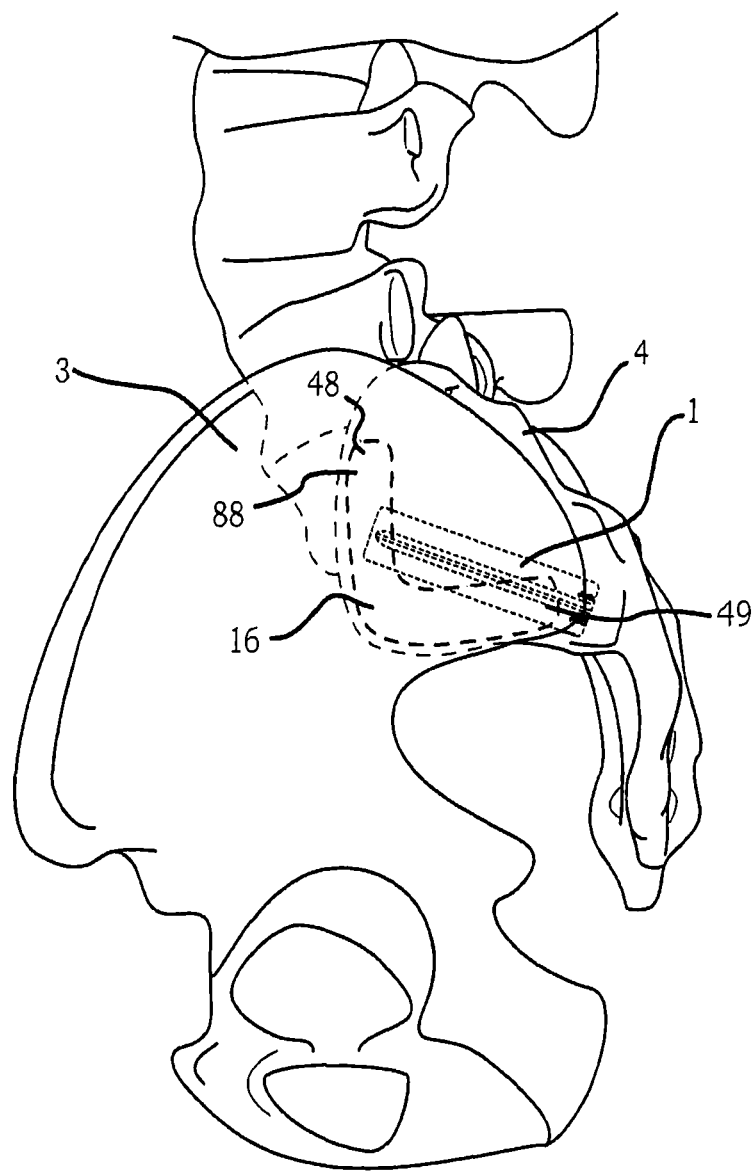
FIG. 46 is a side view of the ilium with the articular region shown bounded by broken line showing placement of an embodiment of the sacroiliac joint implant both within and without the articular region and engaging both the articular surfaces and the extra-articular surfaces of the sacroiliac joint.
Figure 47:
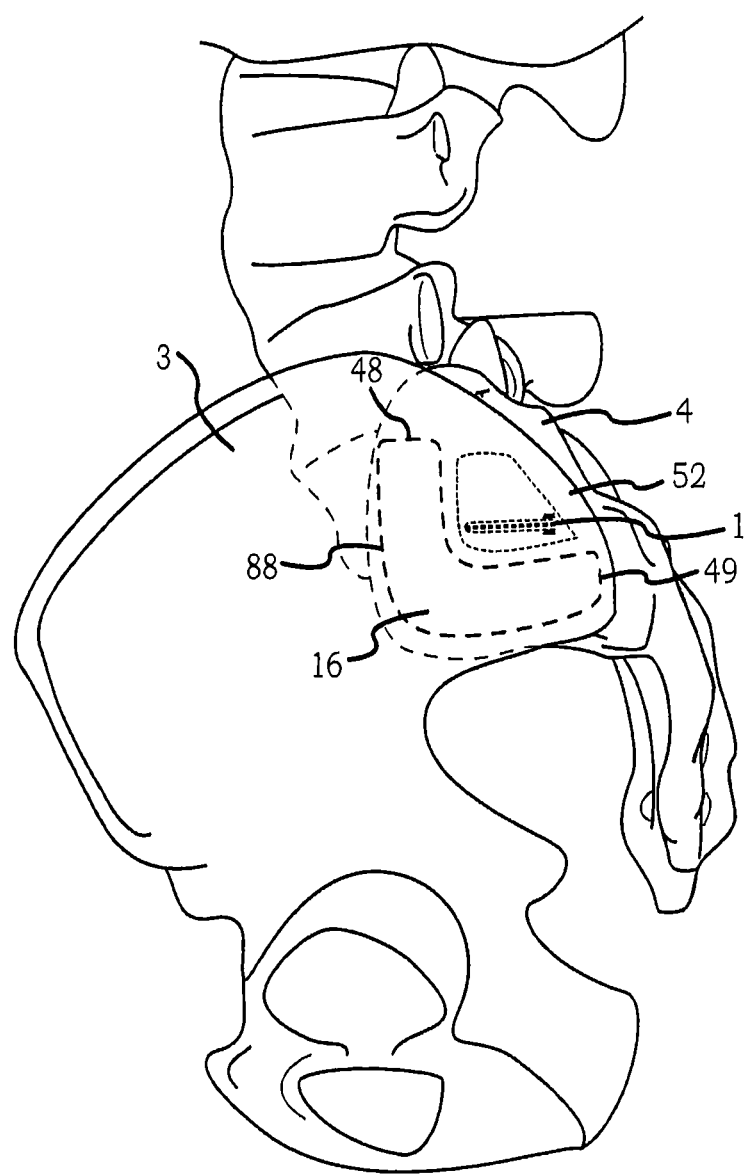
FIG. 47 is a side view of the ilium with the articular region shown bounded by broken line showing placement of an embodiment of the sacroiliac joint implant outside of the articular region and engaging only the extra-articular surfaces of the sacroiliac joint.

Now referring primarily to FIGS. 42A-42C, the implant receiving space (50) and the sacroiliac joint implant (1) can be configured having related dimension relations such that placement of the sacroiliac joint implant (1) within the implant receiving space (50) disposes the sacrum (4) and the ilium (3) in substantially immobilized relation or allows the sacrum (4) and the ilium (3) a limited amount of movement corresponding to the movement afforded between the sacral member interface (57) and the iliac member interface (58) of the implant (1) without substantial alteration or avoids alteration of the positional relation of the sacrum (4) and the ilium (3) from the normal condition, or avoids driving together or driving apart the sacrum (4) from the ilium (3) outside of or substantially outside of the normal positional relation. An intention in selecting configurations of the sacroiliac joint implant (1) and the implant receiving space (50) being immobilization or allowing limited movement of the sacrum (4) in relation to the ilium (3) while maintaining the sacroiliac joint (47) in substantially normal or substantially normal positional relation, or returning the sacroiliac joint (47) to a substantially normal positional relation to correct a degenerative condition of the sacroiliac joint (47).

Any of the above-described implant embodiments may be configured for delivery into the sacroiliac joint via any of the delivery tools described in U.S. patent application Ser. No. 13/475,695 ("the '695 application") (filed May 18, 2012) or U.S. patent application Ser. No. 13/236,411 ("the 411 application") (filed Sep. 19, 2011). The disclosures of these two applications are hereby incorporated by reference in their entireties.

In one embodiment, as indicated in FIGS. 48A-49, a system for treating a sacroiliac joint 100 may include a delivery tool 120 for implanting any of the above-described implants 1, wherein the implants 1 have been adapted for use with the delivery tool. An implant assembly 150 includes an implant 1 and, and in some embodiments, one or more anchor elements 130 (e.g., bone screws, nails or other elongated bodies) that may be used to secure the sacrum member of the implant 1 to the sacrum and the ilium member of the implant 1 to the ilium, the sacrum member and ilium member being at least partially moveable relative each other once implanted, as described above in detail.

During the implantation of the implant assembly 150 at the sacroiliac joint, the implant 1 is supported by a distal end 135 of the delivery tool 120, as illustrated in FIG. 48A. As discussed in detail in the '695 application and '411 application, in some embodiments of the tool 120, the tool may be configured to deliver an anchor element 130 to secure the implant 1 in place within the sacroiliac joint. Specifically, a portion of the tool 120, or via separate other tools, an anchor element 130 may be delivered to extend into the sacrum and sacrum member of the implant 1 to fix the sacrum element of the implant to the sacrum. Similarly, a portion of the tool 120, or via separate other tools, an anchor element 130 may be delivered to extend into the ilium and ilium member of the implant 1 to fix the ilium element of the implant to the sacrum. The sacrum member of the implant 1 and the ilium member of the implant 1 may interact with each via any of the above-described arrangements so as to allow at least some movement between the sacrum member and ilium member once implanted in the sacroiliac joint space.

In some embodiments of the implant 1 as described above, the sacrum and ilium members of the implant are simply respectively secured to the sacrum and ilium via features of the respective sacrum and ilium members and, as a result, do not require the use of anchor elements 130.

As can be understood from FIGS. 48A-49, in one embodiment, the distal end 135 of the delivery tool 120 may be fixed or non-removable from the rest of the delivery tool 120. In other embodiments, the distal end 135 of the delivery tool 120 may be removable so as to allow interchanging of different sized or shaped distal ends 135 to allow matching to particular implant embodiments without requiring the use of a different delivery tool 120. The delivery tool 120 is used to deliver the implant 1 into the sacroiliac joint space. The delivery tool 120 is then decoupled from the implanted implant assembly 150, as can be understood from FIG. 48B.

As shown in FIG. 48A, the delivery tool 120 includes a distal end 135 and a proximal end 180. The distal end 135 supports the implant 1 of the implant assembly 150, and the proximal end 180 is configured to be grasped and manipulated to facilitate the implantation of the implant 1 in the sacroiliac joint.

As illustrated in FIG. 49, the delivery tool 120 further includes a shaft 185, a handle 190, an implant retainer actuation rod 195, and an implant retainer 200. As can be understood from FIGS. 48A-49, the handle 190 is coupled on a proximal end of the shaft 185. A lumen extends through the tubular shaft 185, and the implant retainer 195 extends through the lumen and includes a handle equipped proximal end and a distal end 215 configured to mechanically engage a proximal end 220 of a drive shaft 225 of the implant retainer 200. The implant retainer 200 is positioned within a distal end of the shaft 185. When the actuation rod 195 is rotated within, and relative to, the shaft 185, the rotation of the actuation rod 195 causes the drive shaft 225 of the implant retainer 200 to rotate on account of the drive shaft proximal end 220 being mechanically coupled to the actuation rod distal end 215.

As illustrated in FIG. 50-53, the implant retainer 200 includes the drive shaft 225, implant member engagement shafts 230, 232, and a frame 235. The implant member engagement shafts 230, 232 are rotatably supported in the frame 235 and include geared proximal ends 240, 242 and threaded distal ends 245, 247. The drive shaft 225 is rotatably supported in the frame 235 and includes a geared portion 250 that is engaged via a geared relationship with the geared proximal ends 240, 242 of the implant member engagement shafts 230, 232 such that rotation of the drive shaft 225 causes rotation of the shafts 230, 232. Rotation of the drive shaft 225 causes rotation of the shafts 230, 232 in first directions that allows the respective threaded ends 245, 247 to rotate so as to be threadably received in threaded bores 255, 257 of respective sacrum and ilium members 53, 55, thereby causing the members 53, 55 to be secured to the implant retainer 200 and the distal end 135 of the delivery tool 120. Opposite rotation of the drive shaft 225 causes the respective threaded ends 245, 247 to threadably exit the respective threaded bores 255, 257, thereby allowing the delivery tool distal end 135 to uncouple from the implant members 53, 55 once implanted in the sacroiliac joint space. Rotation arrows near the drive shaft proximal end and the proximal and distal ends of the respective shafts 230, 232 illustrate the rotational relationships between the shafts 225, 230, 232.

Figure 50:
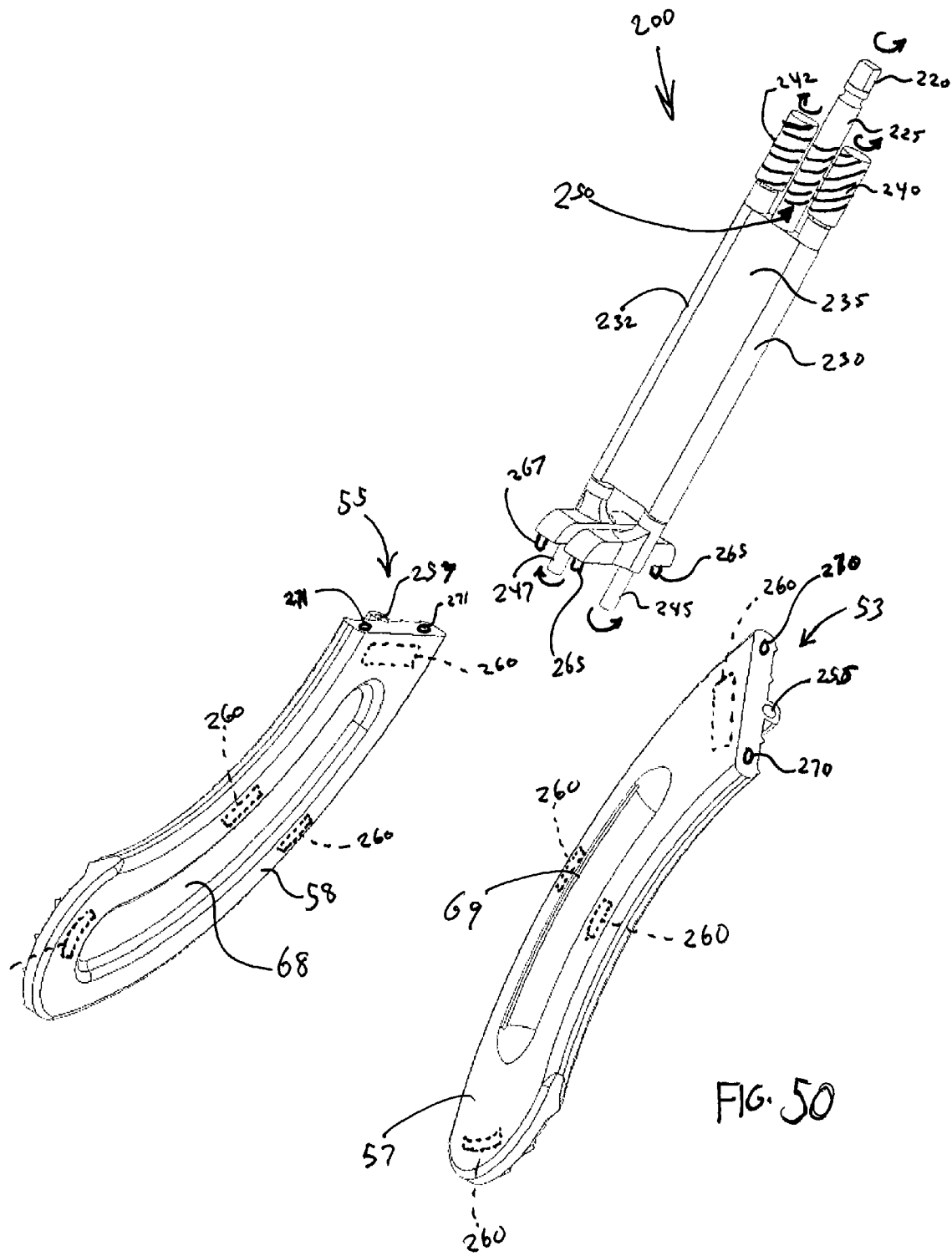
FIG. 50 is an exploded isometric view of the implant retainer and implant indicated in FIG. 49.

The implant 1 of FIGS. 50-53 has features similar to those described above with respect to FIGS. 24 and 25, including, for example, arcuate or curved bodies of the members 53, 55, a guide element 69 and a complementarily shaped channel element 68, and fixation members 86. Additionally and as indicated in FIG. 50, in one embodiment, magnets 260, 262 may be supported in each member 53, 55 near the interface surfaces 57, 58 of the respective members 53, 55. The magnets 260, 262 may be arranged in opposed paired fashion on the respective interface surfaces 57, 58 in such a manner to cause the opposed paired magnets 260, 262 to draw the opposed interface surfaces 57, 58 towards each other or to cause the opposed interface surfaces 57, 58 to repel each other. In such an embodiment, the repelling magnets may act to reduce abrasion or wear of the opposing interface surfaces.

In one embodiment, the implant members 53, 55 may be constrained. For example, the implant members 53, 55 may be connected to each other by structural elements extending between or around the surfaces of each implant member 53, 55. Such structural elements may include any of the constraining, linking or connecting structures discussed above with respect to FIGS. 9 and 10 or FIGS. 17-41, for example. Alternatively or additionally, the constraining, linking or connecting structures may include fibers (e.g., woven) that extend between and/or about (e.g., circumferentially) the surfaces of the members 53, 55, those surfaces including the interface surfaces and/or the exterior side and back surfaces of the implant members.

As can be understood from FIGS. 50-53, the distal end of the implant retainer 200 that interfaces with the proximal end of the implant 1 may have protruding tabs 265, 267 that are respectively received in bores 270, 271 defined in the proximal end of the implant 1. Such tabs 265, 267 prevent the implant portions 53, 55 from rotating relative to the implant retainer 200 when the shafts 230, 232 are being rotated to cause their distal ends 245, 247 to be received in threaded engagement within the bores 255, 257.

In the embodiment of the delivery tool 120 depicted in FIGS. 48A-52, an implant engagement arrangement exists wherein rotation of the retainer 195 relative to the rest of the delivery tool 120 results in the shafts 230, 232 rotating appropriate to allow their respective threaded distal ends 245, 247 to theadably couple to the threaded bores 255, 257 of the implant 1. In another embodiment of the delivery tool 120 as will now be discussed with respect to FIGS. 54A-

54E, the shafts 230, 232 may be simply be caused to rotate via direct rotating action of the physicians fingers against the shafts 230, 232.

Figure 54A:
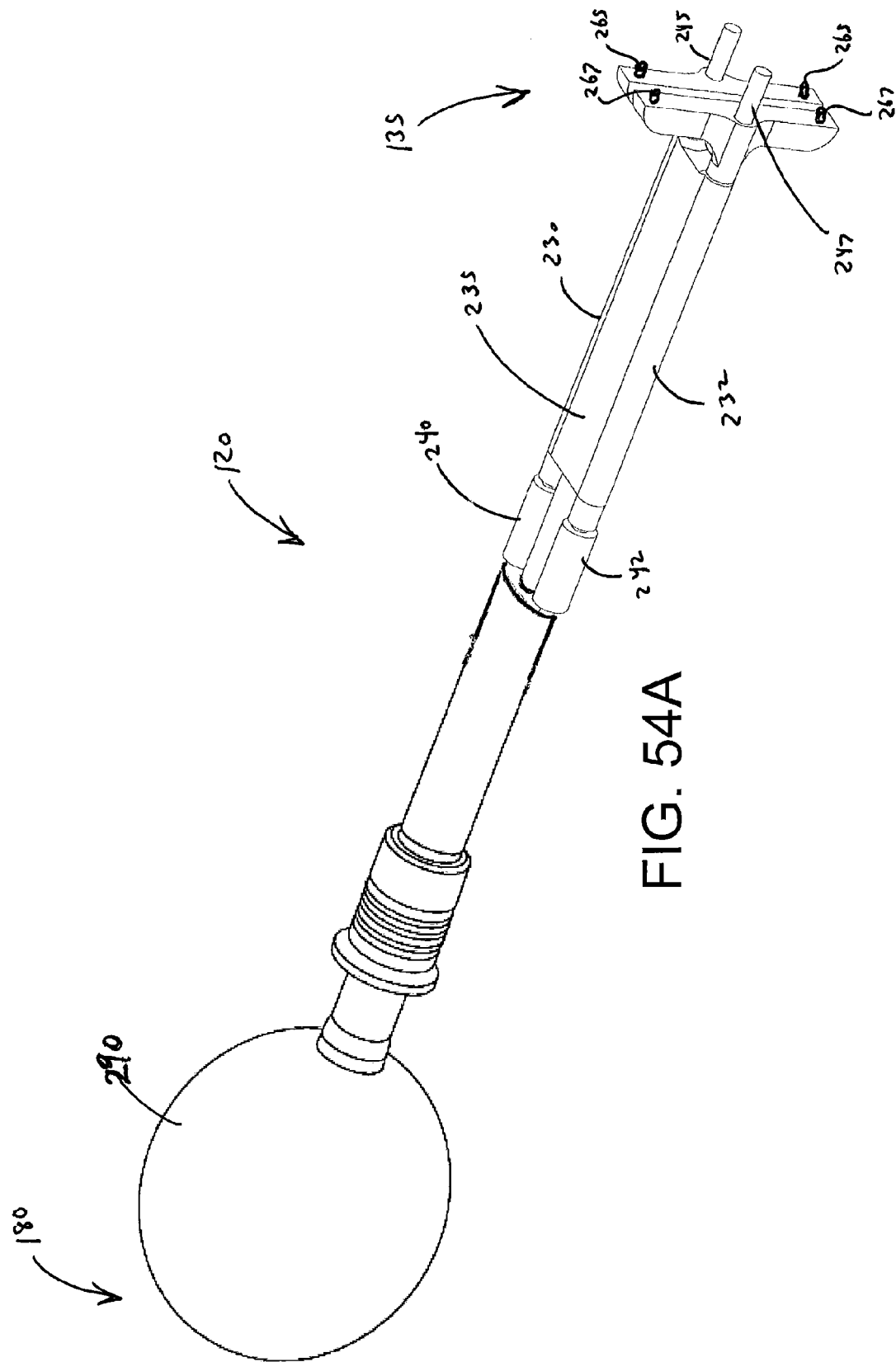
FIG. 54A is an isometric view of the delivery tool.
Figure 54B:
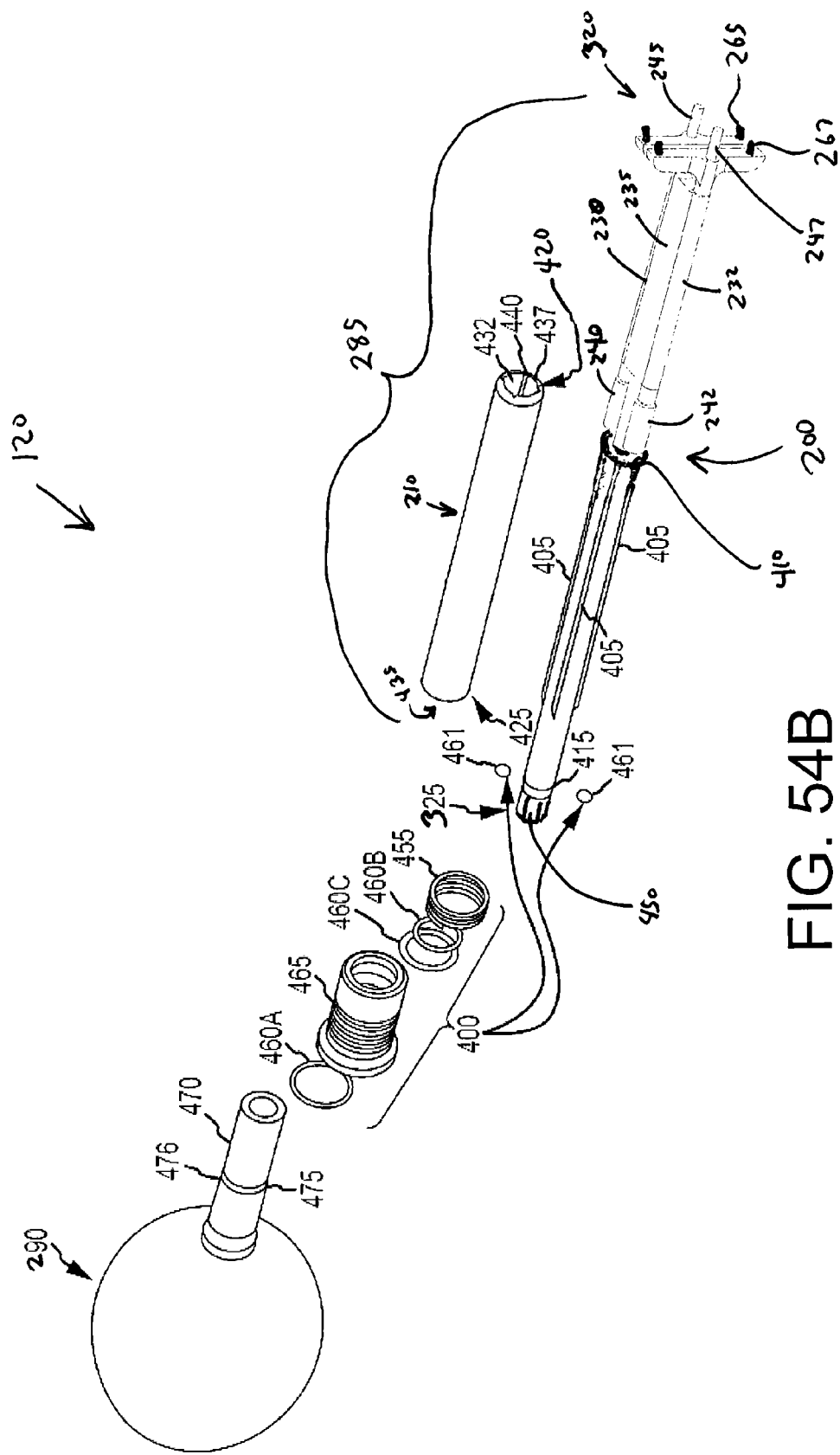
FIG. 54B is an isometric view of the delivery tool in an exploded state.

As shown in FIG. 54A, the delivery tool 120 includes a distal end 135 and a proximal end 180. As shown in FIG. 54B, the tool 120 further includes an arm assembly 285 and a handle 290.

As can be understood from FIGS. 54A-54B, the arm assembly 285 includes a sheath or shell 210 and an implant retainer 200 that resides within the shell 210 when the tool 120 is assembled. The retainer 200 includes a distal end 320 and a proximal end 325. Longitudinally extending raised ribs 405 are radially distributed about the outer circumferential surface of retainer 200. The longitudinal ribs 405 distally terminate by intersecting a raised circumferential ring 410 on the outer circumferential surface of the retainer 200. A groove 415 circumferentially extends about the outer circumference of the retainer 200. The proximal end 325 of the retainer 200 may include a squared, pentagonal or hexagonal outer surface configuration 450 that facilitates a mechanical engagement arrangement with the handle 90 such as the mechanical arrangement that exists between a wrench and nut.

As illustrated in FIG. 54B, the sheath 210 includes a distal end 420, a proximal end 425, a proximal cylindrical opening 435 of a cylindrical bore 432, and a distal cylindrical opening 437 of the bore 432. The cylindrical bore 432 extends the full length of the sheath 210 between the proximal opening 435 and the distal opening 437. Longitudinally extending grooves 440 are radially distributed about the inner circumferential surface of the bore 432 in an arrangement that matches the longitudinal raised ribs 405 of the retainer 200 such that the ribs 405 are received in the grooves 440 in a mated arrangement when the retainer 200 is received in the bore 432 of the sheath 210.

As illustrated in FIG. 54B, the collar assembly 400 includes a helical spring 455, rings 460A and 460B, washer 460C, retainer balls 461, and a retaining collar 465. As shown in FIG. 54C, which is an isometric view of the handle 290, a cylindrical neck portion 470 of the handle 290 includes a shoulder 476 which slopes down to a circumferential groove 475 and a pair of holes 480 defined in the outer circumferential surface of the neck 470.

As indicated in FIG. 54D, which is an exploded isometric view of the retaining collar 465 and handle 290 shown in longitudinal cross section, the holes 480 extend through the cylindrical wall 485 that defines the neck 470 and a cylindrical void 487 within the neck. A squared, pentagonal or hexagonal inner surface configuration 490 is defined in the handle 290 distal the cylindrical void 487 to receive in a mating arrangement the complementarily shaped outer configuration 450 of the proximal end of the retainer 200. A lumen 495 extends from a proximal end of the handle to open into the squared, pentagonal or hexagonal inner surface configuration 490.

As shown in FIG. 54D, the retaining collar 465 includes a proximal end 500, a distal end 505, an outer circumferential surface 510 and an inner circumferential surface 515 that defines the hollow interior of the collar 517. The outer circumferential surface 510 extends radially outward to form a rim 520 near the proximal end 500. The inner circumferential surface 515 has a stepped and ramped configuration. Specifically, working distal to proximal, the inner circumferential surface 515 includes a proximal inner ring 525 separated from an intermediate inner ring 530 by a proximal large diameter region 535 separated from a small diameter region 540 by a ramped surface 545. Proximal the intermediate inner ring 530 is another large diameter region 550 bordered on its proximal boundary by a groove 555.

Figure 54E:
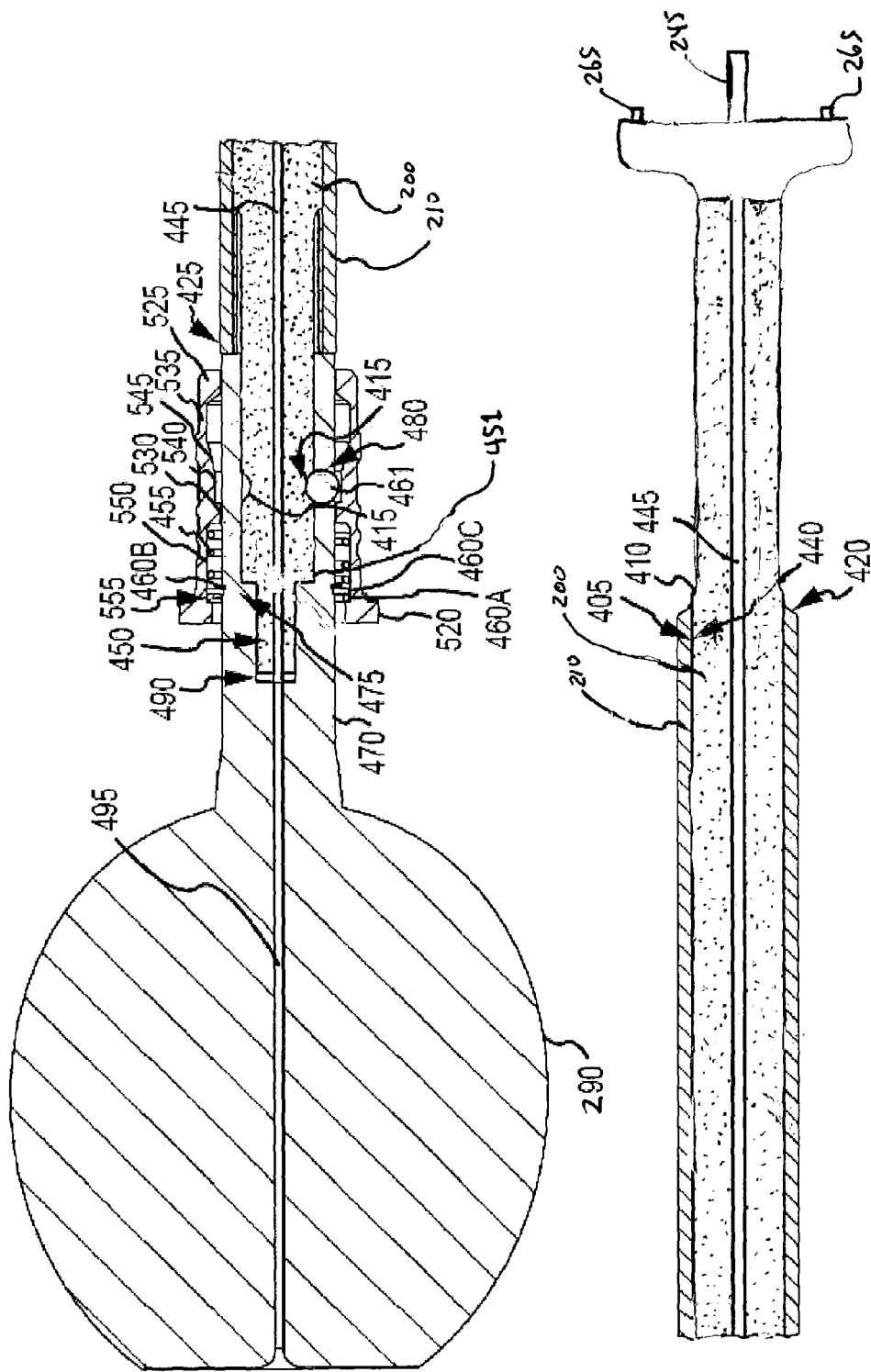
FIG. 54E is a longitudinal cross section of the delivery tool when assembled as shown in FIG. 54A.

As can be understood from FIG. 54E, which is a longitudinal cross section of the delivery tool 120 when assembled as shown in FIG. 54A, the implant retainer 200 is received in the sleeve 210 such that the ribs 405 are matingly received in the corresponding slots 440 and the ring 410 abuts against the distal end 420 of the sleeve 210. The implant retainer 200 extends through the sleeve 210 such that the distal end of the implant retainer distally extends from the distal end of the sleeve 210. The proximal end of the retainer 200 is received in the volume 487 (see FIG. 54D) of the neck 470, the squared, pentagonal, or hexagonal portion 450 of the retainer 200 matingly received in the complementarily shaped volume 490 of the neck such that a lip 451 abuts against the step in the neck between the volume 490 of the neck and the rest of the volume of the neck distal thereto. The distal end of the neck 470 abuts against the proximal end 425 of the sleeve 210.

As illustrated in FIG. 54E, a first lock ring 460A is received in the groove 555 in the collar 465. A second lock ring 460B is received in the circumferential groove 475. A washer 460C is received on the neck 470 and abuts shoulder 476, which prevents washer 460C from advancing proximally beyond shoulder 476, and washer 460C is held in place distally by second lock ring 460B. Helical spring 455 circumferentially extends about the neck 470 between the washer 460C and the intermediate inner ring 530 of the collar 465. Thus, the spring biases the collar 465 distally on the neck 470. First lock ring 460A prevents collar 465 from distal disengagement from neck 470; the ring 460A, due to the forces exerted by a compressed spring 455 abuts washer 460C under normal conditions until manipulation by a medical person acting to move collar 465 proximally which in turn moves first lock ring 460A proximally thereby creating a further distance between first lock ring 460A and washer 460C.

As depicted in FIG. 54E, neck holes 480 can be configured to have a sufficient diameter to allow the retaining balls 461 to enter from the opening nearest the outer circumferential surface of the neck 470 and to be seated within holes 480, the configuration further allowing a portion of the retaining balls 461 to extend into the cylindrical void 487 such to allow sufficient engagement with groove 415 as further described below. The neck holes 480 can be further configured, as depicted in FIG. 54E, to have a slight reduction in their diameter, the reduction of diameter occupying a small portion of the holes 480 nearest the cylindrical void 487, thereby allowing for a configuration between neck 470, neck holes 480 and retaining balls 461 such that the retaining balls 461 are resistant to completely entering cylindrical void 487 after the removal of inner portion of the implant retainer 95 and implant retainer 200. The balls 461 are each held in their respective holes 480 in the neck 470 by the balls 461 being trapped between the neck holes 480 and inner circumferential surface of the collar 465. Therefore, when the collar 465 is biased distally on the neck, the balls 461 are inwardly forced by the reduced diameter region 540 to lock into the groove 415 of the retainer 200, retaining the proximal end of the retainer 200 in the handle/collar assembly. When the collar 465 is pulled proximally by a medical person using the tool 120, the balls 461 are exposed to the large diameter region 535, allowing the balls 461 sufficient play to radially outwardly move in the holes 480 to allow the balls to escape the groove 415, thereby allowing the proximal end of the retainer 200 to be removed from the handle/collar assembly.

As shown in FIG. 54E, the lumens 495 and 445 are aligned to make one continuous lumen through the assembled tool 120. Thus, the tool 120 can be fed over a guidewire, stylet, needle or etc., or such implements can be fed through the lumen. Also, a bone paste, in situ curable biocompatible material, or similar material can be fed through the lumen to an implant 1 positioned in the joint via the tool.

As can be understood from FIGS. 54A-54E, the collar assembly 400 retains the proximal end of the arm assembly 285 in the neck of the handle 290. The collar assembly 400 can be displaced proximally on the neck of the handle 290 to allow the proximal end of arm 285 to be removed from the neck of the handle. When the implant arm 285 is coupled to the handle 290, the portions 200, 210 of the implant arm 285 are locked together and prevented from displacing relative to each other. The handle and rest of the tool can be caused to rotate or otherwise displaced as a unit.

In the embodiment of the delivery tool 120 depicted in FIGS. 54A-54E, the implant engagement arrangement is such that the shafts 230, 232 may be simply be caused to rotate via direct rotating action of the physicians fingers against the shafts 230, 232 and, more specifically, the proximal heads 240, 242 of the shafts 230, 232. Reversing the rotation of the shafts will allow the shaft distal ends 245, 247 to unthread from the confines of the implant threaded bores 270, 271.

In one embodiment, as can be understood from U.S. patent application Ser. No. 13/475,695, which was filed May 18, 2012 and is hereby incorporated by reference in its entirety, the sleeve 210 may be used to support an anchor delivery arm for delivering one or more anchors into and/or about the implant 1 once implanted in the sacroiliac joint space.

FIGS. 55A-55E illustrate yet another embodiment of a sacroiliac joint implant 1 for implantation in a sacroiliac joint space defined between an ilium and a sacrum. As indicated in FIGS. 55A-55E, the implant 1 includes an iliac member 700 and a sacrum member 702, wherein the iliac member and a sacrum member are configured for overlapping, interlocking attachment with each other.

Figure 55A:
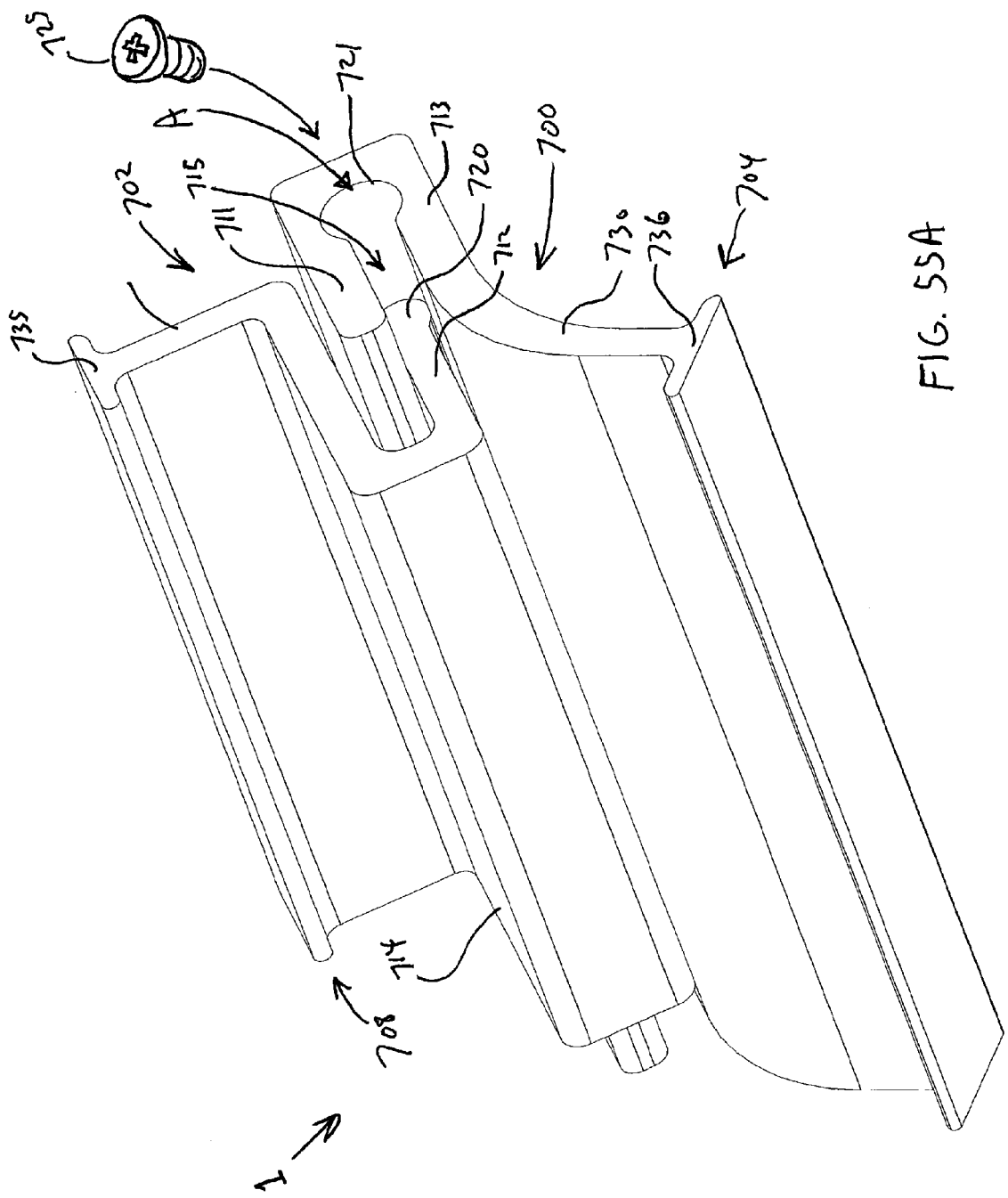
FIGS. 55A and 55B are isometric views of an embodiment of the implant wherein the implant includes an iliac member and a sacrum member configured for overlapping, interlocking attachment with each other.
Figure 55B:
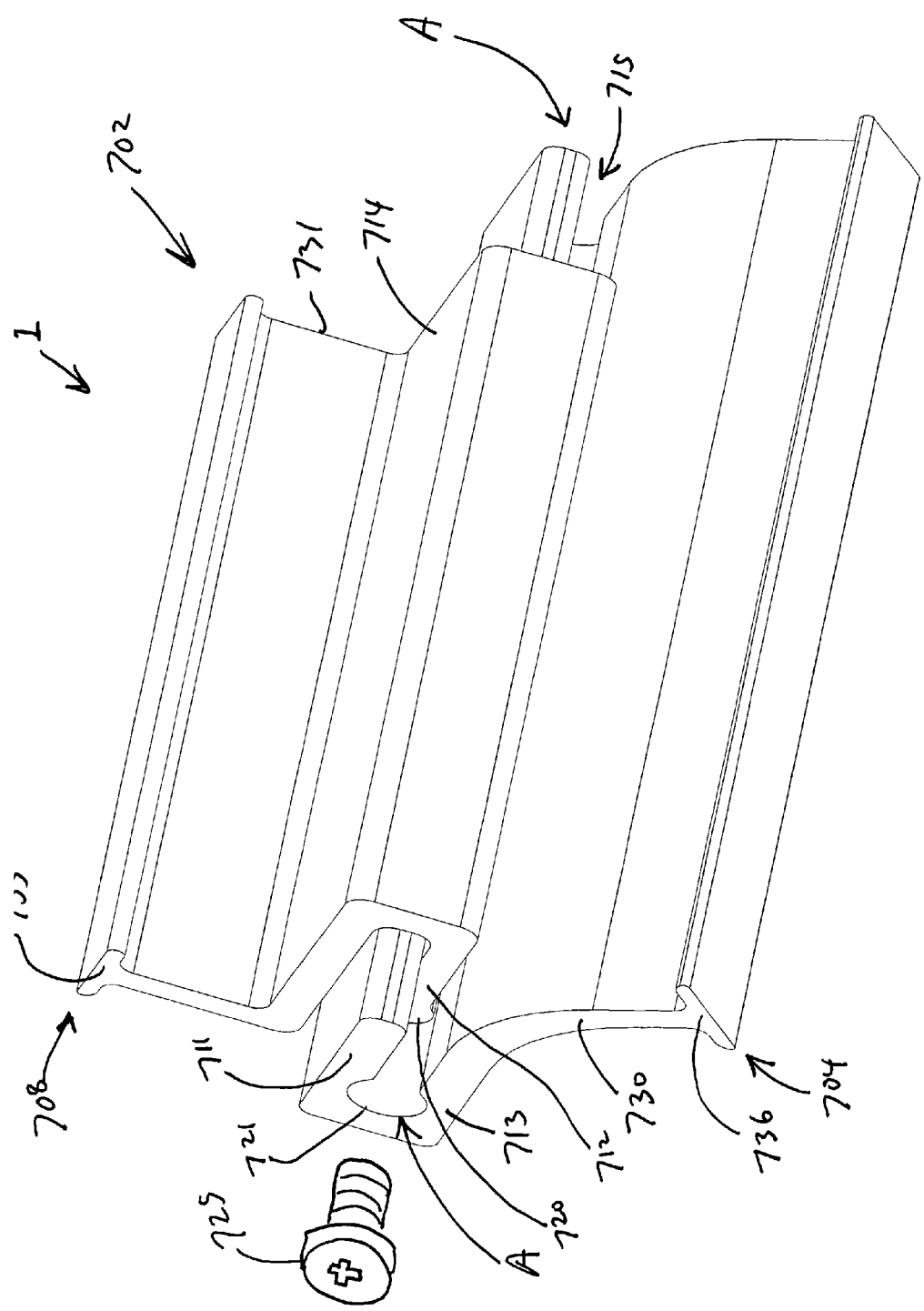
Figure 55C:
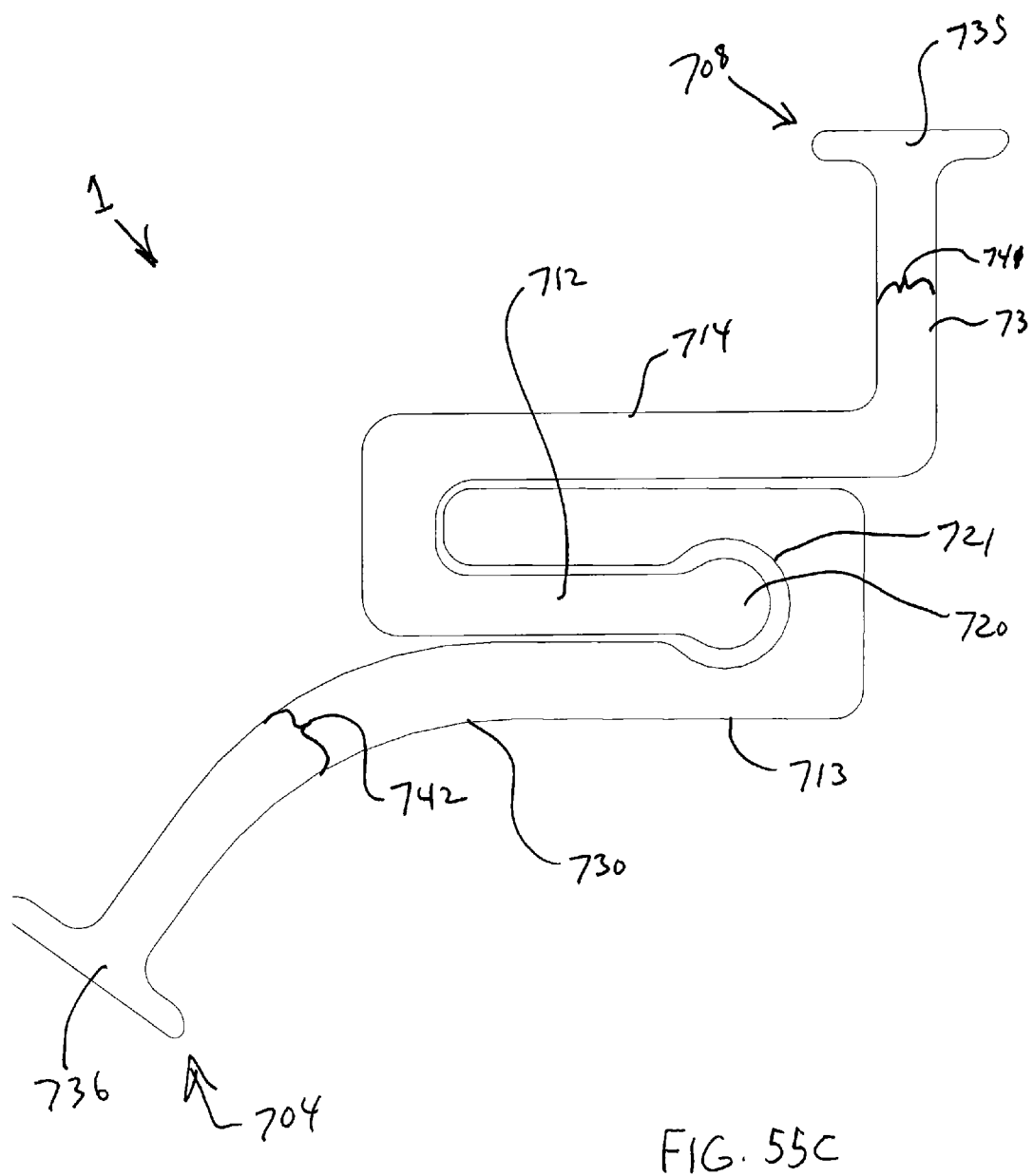
FIG. 55C is a distal end view of the implant of FIGS. 55A and 55B.
Figure 55D:
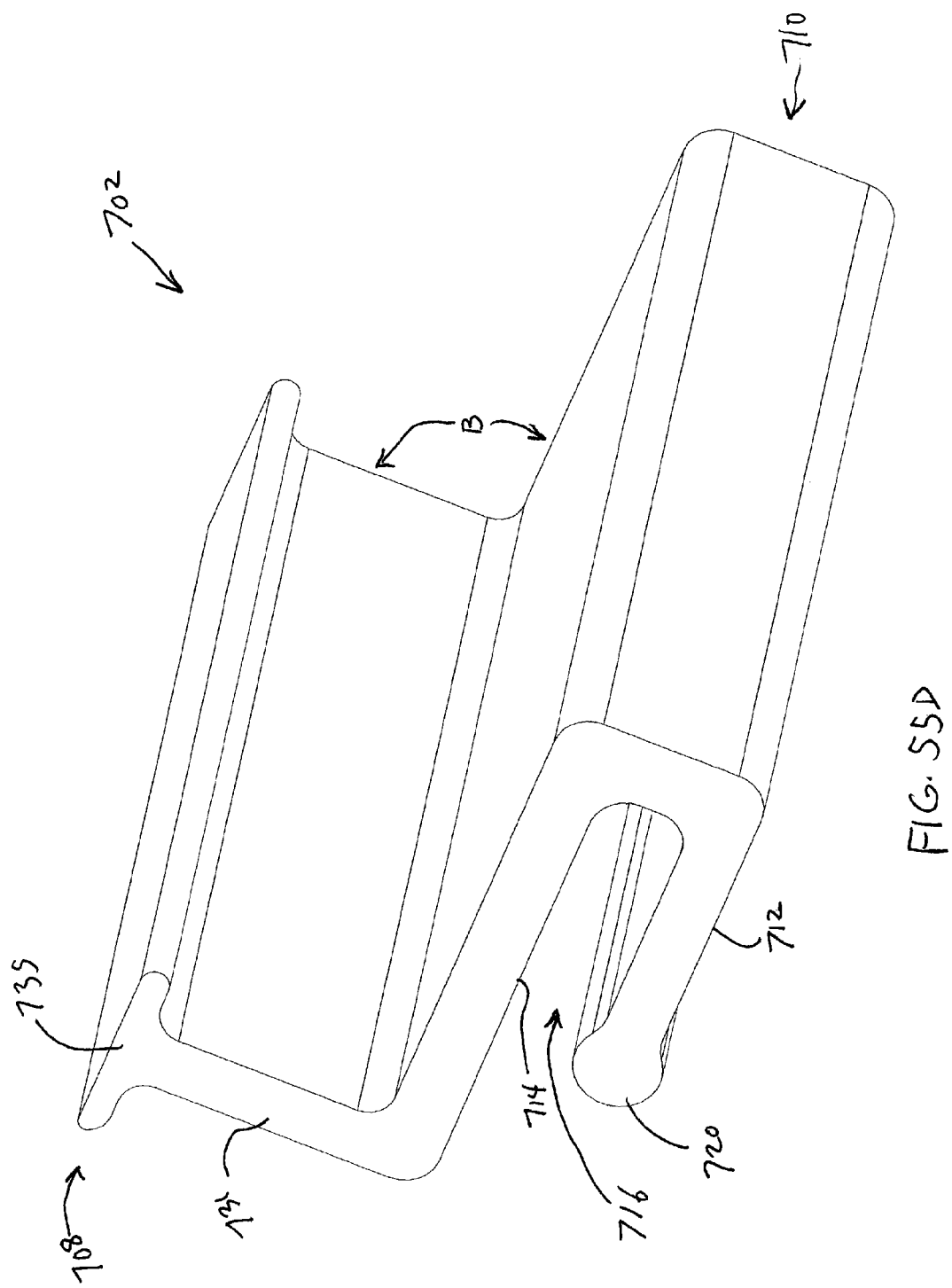
FIG. 55D is an isometric view of the sacrum member of the implant of FIGS. 55A and 55B.
Figure 55E:
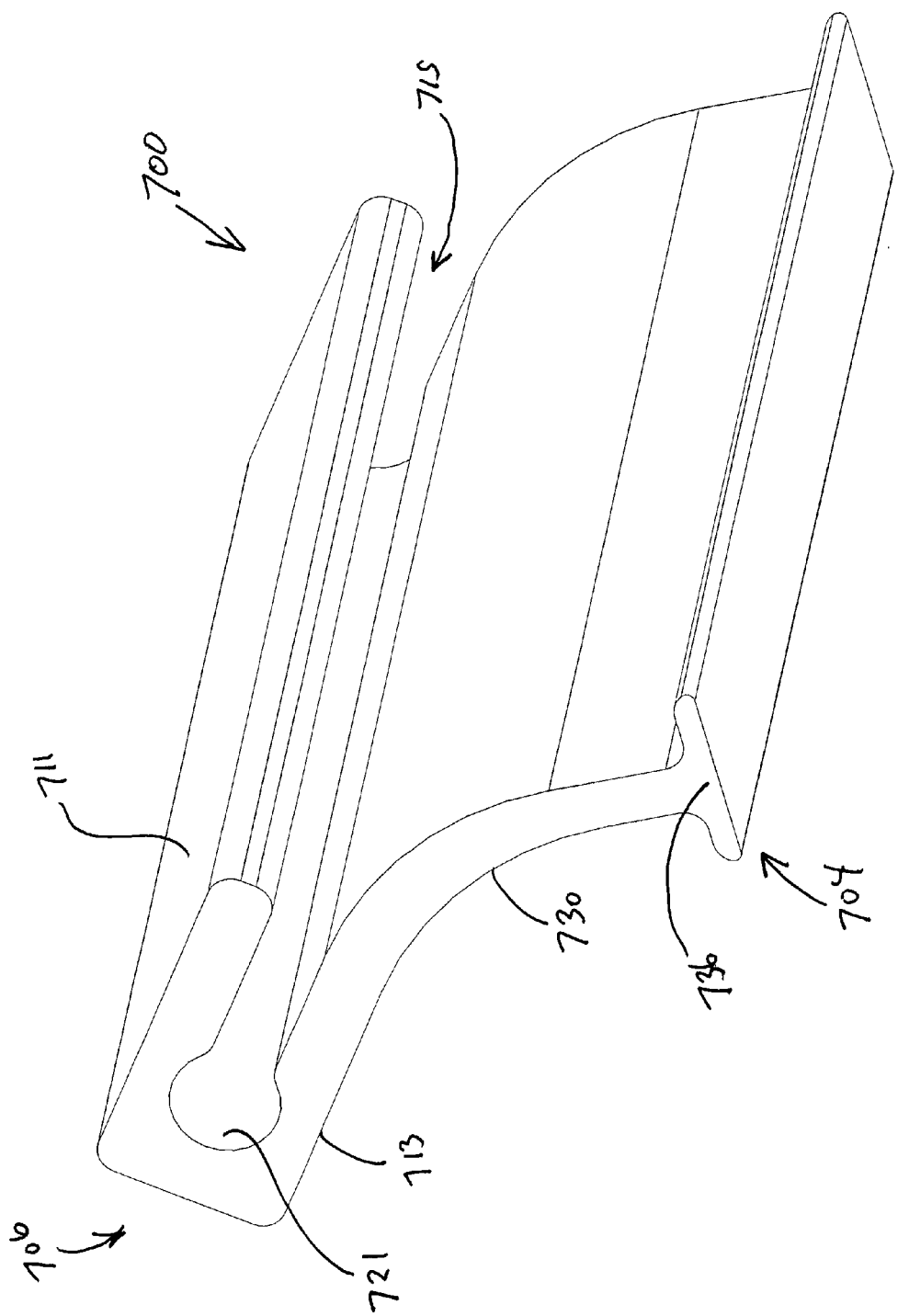
FIG. 55E is an isometric view of the ilium member of the implant of FIGS. 55A and 55B.

As shown in FIG. 55E, the ilium member 700 includes a ilium engaging end 704 and a sacrum member engaging end 706 generally opposite the ilium member from the ilium engaging end. As illustrated in FIG. 55D, the sacrum member 702 includes a sacrum engaging end and a ilium member engaging end 710 generally opposite the sacrum member from the sacrum engaging end. As can be understood from FIGS. 55A-55C, the sacrum member engaging end and the ilium member engaging end are configured for overlapping, interlocking attachment with each other. This type of attachment is at least in part made possible, for example, by the sacrum member engaging end and the ilium member engaging end each have a folded configuration. Each folded configuration includes a free end portion 711, 712 extending into an intermediate portion 713, 714 that is generally parallel to the free end portion and offset from the free end portion so as to define a gap 715, 716 between the free end portion and the intermediate portion.

As illustrated in FIGS. 55A-55C, when the sacrum member engaging end 706 and the ilium member engaging end 710 are in overlapping, interlocking attachment with each other, the free end portion 712 of the sacrum member engaging end is located in the gap 715 of the ilium member engaging end, and the free end portion 711 of the ilium member engaging end is located in the gap 716 of the sacrum member engaging end.

As shown in FIG. 55D, the free end portion 712 of the sacrum member includes a cylindrical extreme edge 720. As indicated in FIG. 55E, the ilium member includes a cylindrical groove 721 defined in the gap of the ilium member at a junction between the free end and intermediate portions of the ilium member. Thus, as illustrated in FIGS. 55A-55E, when the sacrum member engaging end and the ilium member engaging end are in overlapping, interlocking attachment with each other, the cylindrical extreme edge is matingly received in the cylindrical groove. In some embodiments, the overlapping, interlocking attachment may be such that the members 700, 702 are held generally rigid relative to each other. In other embodiments, there may be some play between the members 700, 702 when in the overlapping, interlocking attachment with each other. For example, the when the cylindrical extreme end is matingly received in the cylindrical groove, the cylindrical extreme end may be slid along the cylindrical groove. Alternatively or additionally, when the cylindrical extreme end is matingly received in the cylindrical groove, the ilium member and sacrum member may be displaced relative to each other transverse to a length of the cylindrical groove. Depending on the embodiment and the desires of the physician implanting the implant 1, displacement between the members when interlocked may be limited to a greater or lesser extent by the placement of one or more end caps 725 threaded into or otherwise mechanically secured in one or more extreme ends of the cylindrical groove at points A, as indicated in FIGS. 55A-55B. In one embodiment, a spring or resilient member may be positioned between an end cap 725 and the respective edge of the sacrum member to allow some movement of the sacrum member within the groove 721 yet bias the sacrum member to a neutral position within the groove 721.

As shown in FIG. 55E, the ilium member 700 further includes an extension portion 730 extending from its intermediate portion 713 and terminating in the ilium engaging end 704. The extension portion of the ilium member curves as it extends from the intermediate portion of the ilium member to terminate in the ilium engaging end.

As indicated in FIG. 55D, the sacrum member 702 further includes an extension portion 731 extending from its intermediate portion 714 and terminating in the sacrum engaging end 708. The extension portion of the sacrum member is generally straight as it extends at an angle B from the intermediate portion of the sacrum member to terminate in the sacrum engaging end. The angle B may be approximately 90 degrees or, in some embodiments, between approximately 45 degrees and approximately 135 degrees.

In some embodiments, the ilium engaging end 704 and sacrum engaging end 708 may terminate in a feature 735, 736 adapted to facilitating anchoring to the respective bones. For example, one or both of the respective features 735, 736 may have T-flange configuration termination, as shown in FIGS. 55A-55E.

As can be understood from FIGS. 55A-55E, the various portions 711, 713, 730 of the iluim member 700 are formed of a generally continuous wall structure 740 having a length extent and a width that are both significantly greater than a thickness of the wall structure. Similarly, the various portions 712, 714, 731 of the sacrum member 702 are formed of a generally continuous wall structure 741 having a length extent and a width that are both significantly greater than a thickness of the wall structure. While the members 700, 702 may have a generally rectangular shape, in other embodiments, the members 700, 702 may curve similar to the implant members 53, 56 depicted in FIG. 36 discussed above.

In one embodiment, the iliac member 700 may be implanted first by inserting the iliac member 700 into the sacroiliac joint with the T-flange 736 extending into the ilium bone material and the sacrum member engaging portion 406 located in the space of the sacroiliac joint. In inserting the iliac member into the joint space, one edge of the wall structure 742 at one end of the cylindrical groove 721 and T-flange 736 may serve as the distal or leading edge of the iliac member 700, and the opposite end may serve as the proximal or trailing edge of the member 700 and be configured for coupling with any of the delivery tools 120 discussed above. Once the ilium member 700 is implanted as desired, as similar process can be followed to implant the sacrum member 702, with the T-flange extending into the sacrum bone material and the ilium member engaging portion 710 located n the space of the sacroiliac joint, the portion 712 sliding into the groove 715 to create the overlapping, interlocking attachment of the two members 700, 702. In some embodiments, to facilitate easy insertion, the wall structure of the members 700, 702 may be bullet shaped at their respective distal end edges instead of having the distal blunt edges depicted in FIGS. 55A-55E. Also, in some embodiments, instead of being inserted iliac member first, the order could be reversed or both members could be coupled together and then inserted together.

FIGS. 56A-56F illustrate yet another embodiment of a sacroiliac joint implant 1, wherein the implant 1 is configured for transverse implantation across a sacroiliac joint. As indicated in FIGS. 56A-56F, the implant 1 includes an iliac member 800 and a sacrum member 802. The iliac member 800 includes a first bore 805 defined in the iliac member. The iliac member may any shape, including, for example, the boxed-triangular shape illustrated. The sacrum member 802 includes a second bore 806 defined in the sacrum member. The sacrum member may be any shape, including, for example, the boxed-triangular shape illustrated. The bores 805, 806 may extend through the longitudinal length of each respective member 800, 802.

The implant 1 also includes a connecting member 810 having a first end 811 and a second end 812 opposite the first end. The first end 811 is received in the first bore 805 and the second end 812 received in the second bore 806. The connecting member connects the iliac member to the sacrum member.

Figure 56A:
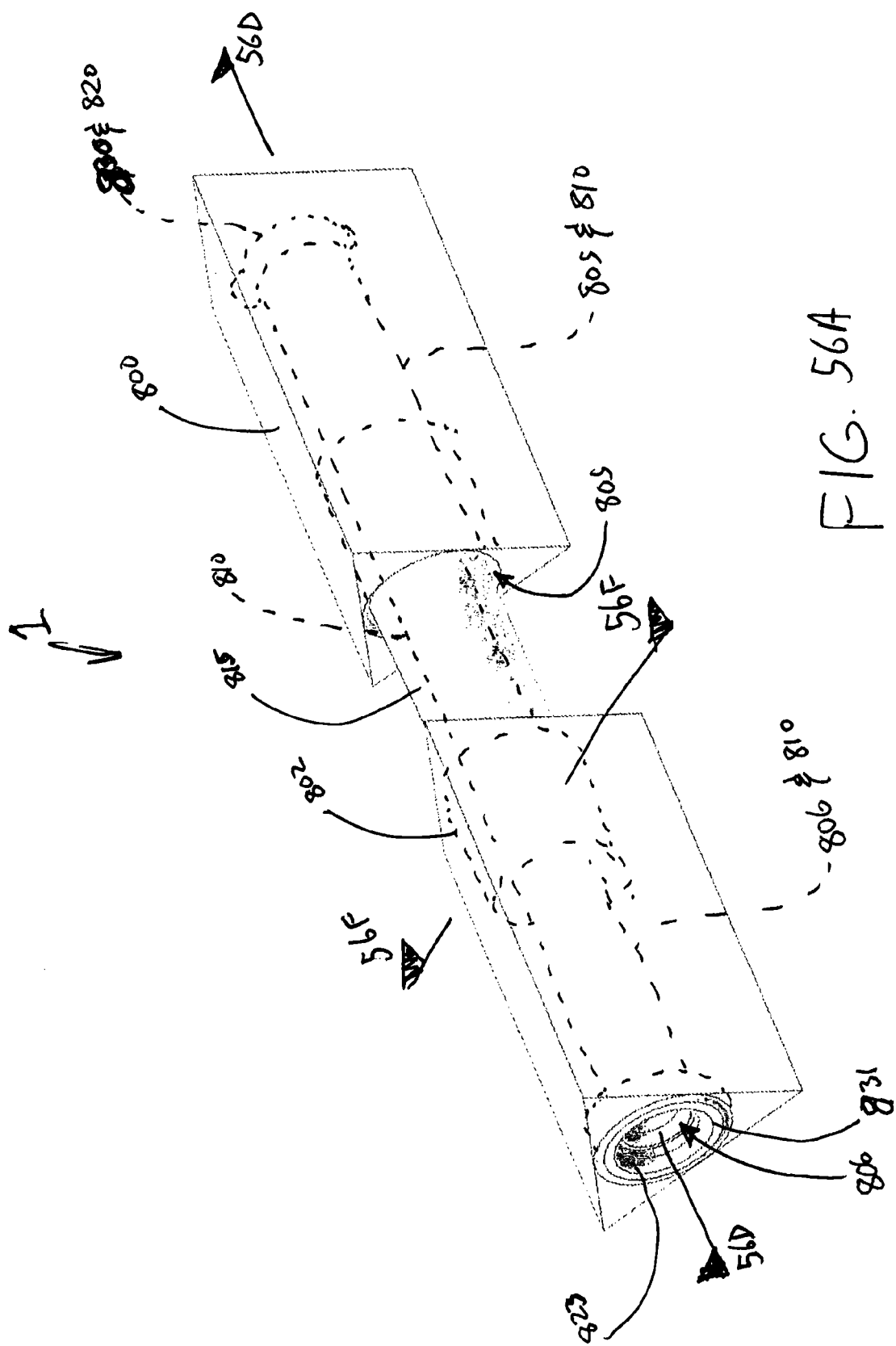
FIG. 56A is an isometric view of an implant configured for transverse implantation across a sacroiliac joint.
Figure 56B:
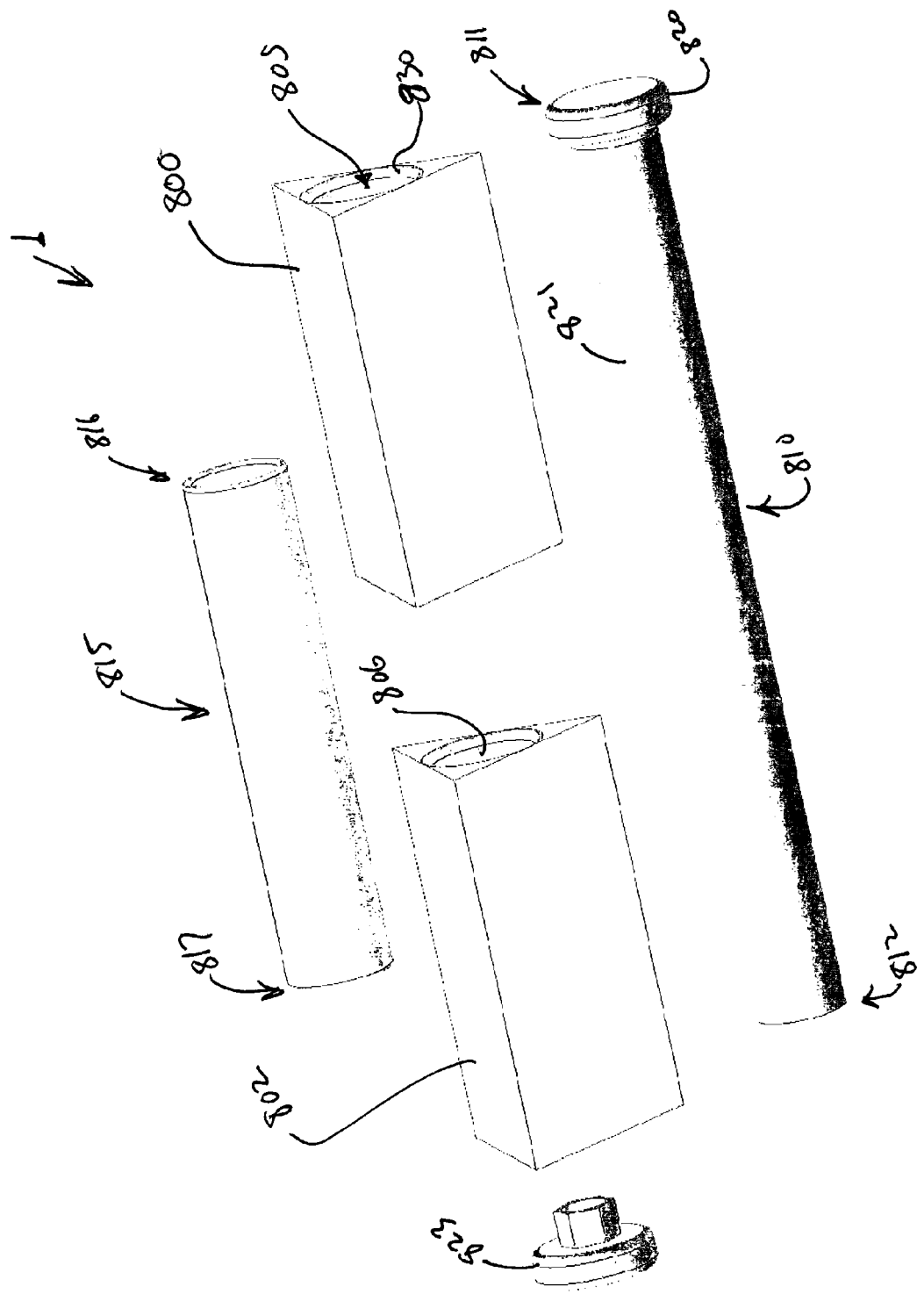

The implant 1 also includes a spacing member 815 extending about the connecting member 810 and having a third end 816 and a fourth end 817 opposite the third end. The third end 816 contacts the iliac member 800 and the fourth end 817 contacts the sacrum member 802. As shown in FIGS. 56A and 56D, the spacing member maintains the iliac member and sacrum member spaced apart from each other.

As indicated in FIG. 56D, the first bore 805 extends a longitudinal length of the iliac member 800. Similarly, the second bore 806 extends a longitudinal length of the sacrum member 802.

As illustrated in FIGS. 56A-56D, the first end 811 includes a head 820 having a diameter greater than a diameter of a shaft portion 821 of the connecting member 810. Similarly, the second end 812 includes a head 823 having a diameter greater than the diameter of the shaft portion 821 of the connecting member 810. In one embodiment, the at least one of the heads (e.g., the second head 823) is removably coupled to the shaft portion 821. As indicated in FIGS. 56D and 56E, this may coupling may be accomplished via a setscrew 825 extending through the second head 823 and into the second end 812 of the connecting member 810.

As can be understood from FIGS. 56A-56E, the end openings 730, 731 of the respective bores 805, 806 of the respective members 800, 802 may have a stepped, recessed configuration and be configured to matingly receive the respective heads 820, 823 in a recessed manner. In a similar fashion, each opposite opening 835, 836 of the respective bores 805, 806 of the respective members 800, 802 may have a stepped, recessed configuration and be configured to receive in a recessed fashion the respective ends 816, 817 of the spacing member 815.

The connecting member 810 may be a cylindrical body and the spacing member 815 may be a cylindrical sleeve. The cylindrical body and cylindrical sleeve may be in coaxially arranged. The connecting member and spacing member may have sufficient rigidity to maintain the members 800, 802 in a fixed spaced apart relationship once implanted such that the members 800, 802 do not migrate towards or away from each other. However, in some embodiments, the connecting member 810 and spacing member 815 may have sufficient flexibility so as to allow the members 800, 802 to deflect relative to each other a sufficient amount to mimic the natural flexion of a healthy sacroiliac joint while providing sufficient rigidity along the implant 1 so as to securely couple the sacrum and ilium together in a manner that generally replicates a natural connection between these two bones.

Figure 56F:
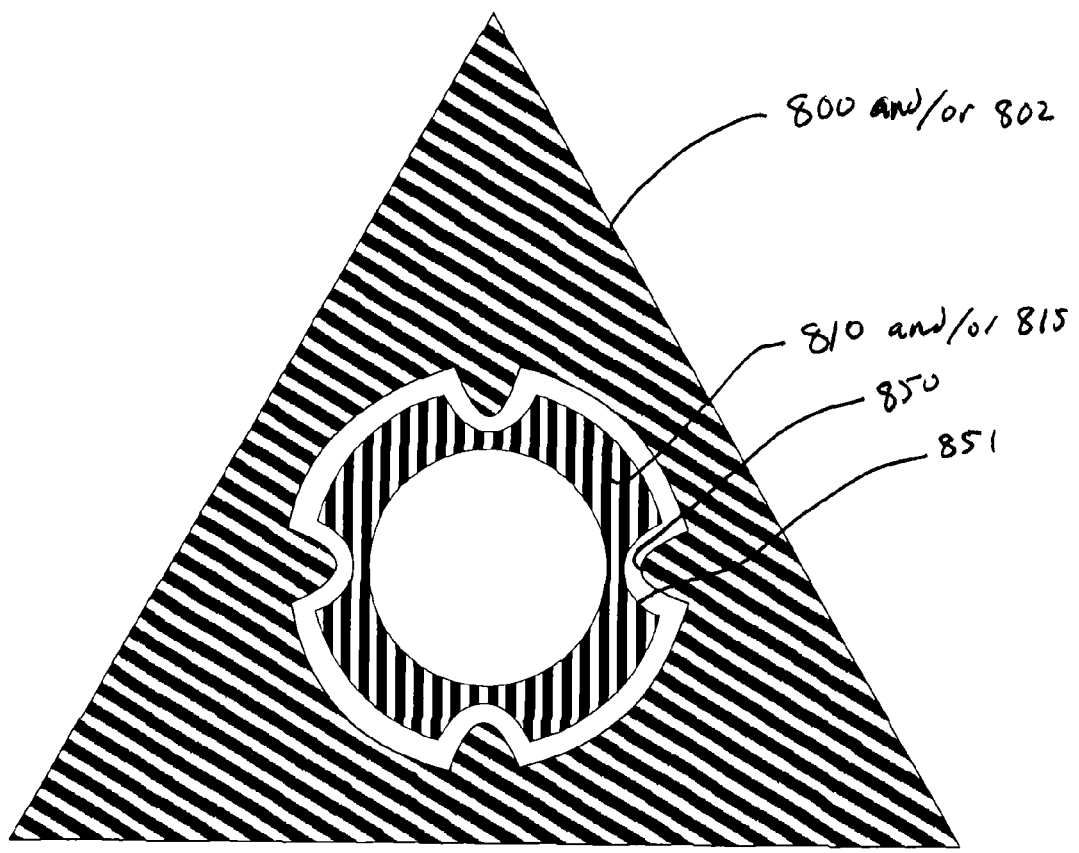
FIG. 56F is a transverse cross sectional elevation of the implant as taken along section line 56F-56F in FIG. 56A.

As illustrated in FIG. 56F, in one embodiment, the interior of one or more of the respective bores 805, 806 may have radially inward projecting features 850 that engage with radially recesses 851 defined in the outer circumferential surface of the connecting member 810 and/or the spacing member 815. Such features 850 and recesses 851 may act to prevent rotation between the members 800, 802 and the members 810, 815.

In one embodiment, the implant 1 of FIGS. 56A-56E can be implanted via the following example method: drill a hole generally lateral-medial through a sacrum, across the sacroiliac joint space and into a ilium; provide an iliac member 800 including a first bore 805 defined in the iliac member; provide a sacrum member 802 including a second bore 806 defined in the sacrum member; provide a connecting member 810 having a first end 811 and a second end 812 opposite the first end; couple the first end to the first bore 805 and insert the iliac member into the hole; position the iliac member 800 in a portion of the hole existing in the ilium, the connecting member 810 extending along the hole; extend a spacing member 815 over the connecting member, the spacing member having a third end 816 and a fourth end 817 opposite the third end, the third end contacting the ilium member 800; and position the sacrum member 802 in a portion of the hole existing in the sacrum and coupling the second end 812 to the second bore 806, the fourth end 817 contacting the sacrum member.

As can be easily understood from the foregoing, the basic concepts of the present invention including the best mode may be embodied in a variety of ways. The invention involves numerous and varied embodiments of a sacroiliac joint implant (1).

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of "an implant" should be understood to encompass disclosure of the act of "implanting"—whether explicitly discussed or not—and, conversely, were there effectively disclosure of the act of "implanting", such a disclosure should be understood to encompass disclosure of "implanting" and even a "means for implanting." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

Moreover, for the purposes of the present invention, the term "a" or "an" entity refers to one or more of that entity. As such, the terms "a" or "an", "one or more" and "at least one" can be used interchangeably herein.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment.

Thus, the applicant(s) should be understood to claim at least: i) each of the devices herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. A method of treating a sacroiliac joint via implantation of an implant into a sacroiliac joint space defining a plane between a sacrum and an ilium and comprising a cranial portion and a caudal portion, the method comprising:
   delivering an iliac member into the sacroiliac joint space, the iliac member including a first arcuate body including a distal end, a proximal end opposite the distal end, a concave superior surface, a convex inferior surface opposite the concave superior surface, an interface surface and a fixation surface generally opposite the interface surface, the iliac member delivered into the sacroiliac joint space such that: the concave superior surface faces an extra-articular region and the convex inferior surface faces away from the extra-articular region; the fixation surface of the iliac member engages the ilium; and the interface surface of the iliac member faces in a direction of the sacrum; and
   delivering a sacrum member into the sacroiliac joint space, the sacrum member including a second arcuate body including a distal end, a proximal end opposite the distal end, a concave superior surface, a convex inferior surface opposite the concave superior surface, an interface surface and a fixation surface generally opposite the interface surface, the sacrum member delivered into the sacroiliac joint space such that: the concave superior surface faces the extra-articular region and the convex inferior surface faces away from the extra-articular region; the fixation surface of the sacrum member engages the sacrum and the interface surface of the sacrum member faces in a direction of the ilium, wherein the interface surface of the iliac member engages the interface surface of the sacrum member such that movement relative to one another is restricted when both the iliac member and the sacrum member are implanted in the plane of the sacroiliac joint space.

2. The method of claim 1, further comprising sandwiching a core element between the interface surface of the iliac member and the interface surface of the sacrum member, such a sandwiched arrangement being a mechanism for engaging the interface surface of the iliac member with the interface surface of the sacrum member.

3. The method of claim 2, wherein the interface surface of the iliac member is maintained in a spaced-apart arrangement from the interface surface of the sacrum member when the core element is sandwiched between the interface surfaces and the interface surfaces are engaged with each other.

4. The method of claim 2, wherein the sandwiched arrangement is established before the iliac member and sacrum member are delivered into the sacroiliac joint space.

5. The method of claim 2, wherein the sandwiched arrangement is established after the iliac member and sacrum member are delivered into the sacroiliac joint space.

6. The method of claim 1, wherein, in engaging the interface surface of the iliac member with the interface surface of the sacrum member, the interface surfaces make direct physical contact and a feature of one of the interface surfaces is received in a feature of the other of the interface surfaces.

7. The method of claim 1, wherein the engagement of the interface surface of the iliac member and the interface surface of the sacrum member results in a sliding mating contact.

8. The method of claim 7, wherein the interface surface of the iliac member includes a first feature and the interface surface of the sacrum member includes a second feature that engages the first feature to partially limit sliding of the sliding mating contact.

9. The method of claim 1, wherein the interface surface of the iliac member includes a first feature and the interface surface of the sacrum member includes a second feature that engages the first feature so as to limit movement between the iliac member and the sacrum member.

10. The method as in any of claim 8 or 9, in which the first feature includes a protrusion and the second feature includes a recess in which the protrusion is received, or the second feature includes a protrusion and the first feature includes a recess in which the protrusion is received.

11. The method of claim 10, wherein the protrusion includes a cylindrical element and the recess includes a channel element.

12. The method of claim 10, wherein the protrusion includes a guide element generally in the form of an elongated ridge and the recess includes an elongated channel element.

13. The method of claim 10, wherein the protrusion includes a convex surface and the recess includes a concave feature.

14. The method of claim 10, wherein the protrusion includes a generally T-shaped cross section transverse to a length of the protrusion, and the recess includes a generally T-shaped cross section transverse to a length of the recess.

15. The method of claim 10, wherein at least one of the fixation surface of the iliac member or the fixation surface of the sacrum member includes an outwardly projecting fixation member.

16. The method of claim 15, wherein the fixation member includes at least one of a longitudinally extending rib or a longitudinally extending member having a T-shaped transverse cross section.

17. The method of claim 10, wherein the engagement of the interface surface of the iliac member with the interface surface of the sacrum member is established before the iliac member and sacrum member are delivered into the sacroiliac joint space.

18. The method of claim 10, wherein the engagement of the interface surface of the iliac member with the interface surface of the sacrum member is established after the iliac member and sacrum member are delivered into the sacroiliac joint space.

19. The method of claim 9, wherein the restricted movement between the iliac member and the sacrum member allows for at least one of a rocking or sliding between the iliac member and the sacrum member.

20. The method of claim 1, wherein at least one of the protrusion or recess extend along the first arcuate body of the iliac member, and at least one of the protrusion or recess extend along the second arcuate body of the sacrum member.

21. The method of claim 1, wherein the iliac member and the sacrum member are delivered non-transversely into the sacroiliac joint space.

22. The method of claim 1, wherein the iliac member and the sacrum member each comprise a curved longitudinal axis extending between the distal end and the proximal end.

23. The method of claim 1, wherein the iliac member and the sacrum member are delivered into the sacroiliac joint space simultaneously with each other.

24. The method as in any of claim 1 or 23, in which delivery of the iliac member and the sacrum member into the sacroiliac joint space is via a delivery tool releasably coupled at a distal end with the iliac member and the sacrum member.

25. The method of claim 24, further comprising decoupling the iliac member and the sacrum member from the distal end of the delivery tool.

26. The method of claim 1, wherein at least one of the fixation surface of the iliac member or the fixation surface of the sacrum member includes an outwardly projecting fixation member.

27. The method of claim 26, wherein the fixation member includes at least one of a longitudinally extending rib or a longitudinally extending member having a T-shaped transverse cross section.

28. The method of claim 26, wherein a curved length of the iliac member and the sacrum member defines a radius of about 20 mm to about 60 mm.

29. The method of claim 28, wherein the outwardly projecting fixation member extends along at least a portion of the curved length of the iliac member or the sacrum member.

30. The method of claim 29, wherein the outwardly projecting fixation member is curved along another radius that matches the radius.

31. The method of claim 1, wherein a curved length of the iliac member and the sacrum member defines a radius of about 20 mm to about 60 mm.

32. The method of claim 1, further comprising:
removing cartilage or bone from the sacroiliac joint space, the sacrum, or the ilium prior to delivery of the implant.

33. The method of claim 32, further comprising:
forming a sacral channel in the sacrum, and forming an iliac channel in the ilium.

34. The method of claim 1, wherein, upon delivery of the iliac member and the sacrum member into the sacroiliac joint space, the distal ends of the first arcuate body and the second arcuate body are positioned in the cranial portion of the sacroiliac joint space, and the proximal ends of the first arcuate body and the second arcuate body are positioned in the caudal portion of the sacroiliac joint space.

35. The method of claim 34, wherein a curved length of the iliac member and the sacrum member defines a radius of about 20 mm to about 60 mm.

\* \* \* \* \*

UNITED STATES PATENT AND TRADEMARK OFFICE
CERTIFICATE OF CORRECTION

PATENT NO. : 9,788,961 B2
APPLICATION NO. : 14/127119
DATED : October 17, 2017
INVENTOR(S) : Donner et al.

Page 1 of 1

It is certified that error appears in the above-identified patent and that said Letters Patent is hereby corrected as shown below:

In the Claims

Claim 10, Column 37, Line 49, delete "claim" and replace with -- claims --.

Claim 24, Column 38, Line 36, delete "claim" and replace with -- claims --.

Signed and Sealed this
Thirty-first Day of July, 2018

Andrei Iancu
*Director of the United States Patent and Trademark Office*